(12) United States Patent
Buck et al.

(10) Patent No.: US 11,735,293 B2
(45) Date of Patent: Aug. 22, 2023

(54) METHODS FOR DETERMINING TRANSITION METAL COMPOUND CONCENTRATIONS IN MULTICOMPONENT LIQUID SYSTEMS

(71) Applicant: Chevron Phillips Chemical Company LP, The Woodlands, TX (US)

(72) Inventors: Richard M. Buck, Bartlesville, OK (US); Qing Yang, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 68 days.

(21) Appl. No.: 17/460,400

(22) Filed: Aug. 30, 2021

(65) Prior Publication Data

US 2021/0391034 A1 Dec. 16, 2021

Related U.S. Application Data

(60) Division of application No. 16/808,492, filed on Mar. 4, 2020, now Pat. No. 11,170,874, which is a
(Continued)

(51) Int. Cl.
*G16C 20/10* (2019.01)
*G16C 20/20* (2019.01)
(Continued)

(52) U.S. Cl.
CPC .......... *G16C 20/10* (2019.02); *B01J 19/0006* (2013.01); *B01J 19/0033* (2013.01);
(Continued)

(58) Field of Classification Search
CPC ...... G16C 20/10; G16C 20/20; C08F 4/65916
See application file for complete search history.

(56) References Cited

U.S. PATENT DOCUMENTS 2,964,514 A 12/1960 Fawcett
3,242,099 A 3/1966 Manyik
(Continued)

FOREIGN PATENT DOCUMENTS

CA 2759535 C 3/2020
CN 105102115 B 2/2020
(Continued)

OTHER PUBLICATIONS

Anubhav Diwan, et al., "An Introduction to Classical Least Squares (CLS) and Multivariate Curve Resolution (MCR) as Applied to UV-VIS, FTIR, and ToF-SIMS," Vacuum Technology & Coating, Jan. 1, 2015, pp. 1-9, XP055831486, Retrieved from the Internet: URL:https://www.academia.edu/download/44356398/An_Introduction_to_Classical_Least_Squar20160403-21106-f2w2qa.pdf [retrieved on Aug. 11, 2021].
(Continued)

*Primary Examiner* — Caixia Lu
(74) *Attorney, Agent, or Firm* — Merchant & Gould P.C.

(57) ABSTRACT

Methods for simultaneously determining the concentrations of transition metal compounds in solutions containing two or more transition metal compounds are described. Polymerization reactor systems providing real-time monitoring and control of the concentrations of the transition metal components of a multicomponent catalyst system are disclosed, as well as methods for operating such polymerization reactor systems, and for improving methods of preparing the multicomponent catalyst system.

20 Claims, 20 Drawing Sheets

Related U.S. Application Data continuation of application No. 16/006,899, filed on Jun. 13, 2018, now Pat. No. 10,679,734, which is a continuation-in-part of application No. 15/939,446, filed on Mar. 29, 2018, now Pat. No. 10,507,445.

(51) Int. Cl.

| | |
|---|---|
| *C08F 4/6592* | (2006.01) |
| *B01J 31/22* | (2006.01) |
| *G01N 21/31* | (2006.01) |
| *G06F 17/17* | (2006.01) |
| *C08F 2/01* | (2006.01) |
| *C08F 2/00* | (2006.01) |
| *G05B 13/04* | (2006.01) |
| *B01J 19/24* | (2006.01) |
| *B01J 19/18* | (2006.01) |
| *B01J 19/00* | (2006.01) |
| *C08F 4/659* | (2006.01) |
| *C08F 10/02* | (2006.01) |
| *G01N 21/33* | (2006.01) |
| *C08F 6/02* | (2006.01) |

(52) U.S. Cl.
CPC ....... *B01J 19/1837* (2013.01); *B01J 19/2435* (2013.01); *B01J 31/2295* (2013.01); *C08F 2/00* (2013.01); *C08F 2/01* (2013.01); *C08F 4/65912* (2013.01); *C08F 4/65916* (2013.01); *G01N 21/31* (2013.01); *G01N 21/314* (2013.01); *G05B 13/042* (2013.01); *G06F 17/17* (2013.01); *G16C 20/20* (2019.02); *B01J 2219/00164* (2013.01); *B01J 2219/00186* (2013.01); *B01J 2219/00198* (2013.01); *B01J 2219/00213* (2013.01); *B01J 2219/00218* (2013.01); *B01J 2219/00231* (2013.01); *C08F 6/02* (2013.01); *C08F 10/02* (2013.01); *G01N 21/33* (2013.01); *G01N 2021/3129* (2013.01); *G01N 2021/3155* (2013.01); *G01N 2201/129* (2013.01)

(56) References Cited

U.S. PATENT DOCUMENTS

| | | | |
|---|---|---|---|
| 3,248,179 | A | 4/1966 | Norwood |
| 4,501,885 | A | 2/1985 | Sherk |
| 4,588,790 | A | 5/1986 | Jenkins, III |
| 4,794,096 | A | 12/1988 | Ewen |
| 4,808,561 | A | 2/1989 | Welborn, Jr. |
| 5,352,749 | A | 10/1994 | DeChellis |
| 5,405,431 | A | 4/1995 | Eastman |
| 5,416,579 | A | 5/1995 | Barshad |
| 5,436,304 | A | 7/1995 | Griffin |
| 5,565,175 | A | 10/1996 | Hottovy |
| 5,575,979 | A | 11/1996 | Hanson |
| 5,576,259 | A | 11/1996 | Hasegawa |
| 5,807,938 | A | 9/1998 | Kaneko |
| 5,919,983 | A | 7/1999 | Rosen |
| 5,998,664 | A | 12/1999 | Hsu |
| 6,107,230 | A | 8/2000 | McDaniel |
| 6,165,929 | A | 12/2000 | McDaniel |
| 6,239,235 | B1 | 5/2001 | Hottovy |
| 6,262,191 | B1 | 7/2001 | Hottovy |
| 6,294,494 | B1 | 9/2001 | McDaniel |
| 6,300,271 | B1 | 10/2001 | McDaniel |
| 6,316,553 | B1 | 11/2001 | McDaniel |
| 6,355,594 | B1 | 3/2002 | McDaniel |
| 6,376,415 | B1 | 4/2002 | McDaniel |
| 6,388,017 | B1 | 5/2002 | McDaniel |
| 6,391,816 | B1 | 5/2002 | McDaniel |
| 6,395,666 | B1 | 5/2002 | McDaniel |
| 6,524,987 | B1 | 2/2003 | Collins |
| 6,548,441 | B1 | 4/2003 | McDaniel |
| 6,548,442 | B1 | 4/2003 | McDaniel |
| 6,576,583 | B1 | 6/2003 | McDaniel |
| 6,613,712 | B1 | 9/2003 | McDaniel |
| 6,632,894 | B1 | 10/2003 | McDaniel |
| 6,667,274 | B1 | 12/2003 | Hawley |
| 6,723,804 | B1 | 4/2004 | Battiste |
| 6,750,302 | B1 | 6/2004 | McDaniel |
| 6,833,415 | B2 | 12/2004 | Kendrick |
| 6,916,892 | B2 | 7/2005 | Tharappel |
| 7,026,494 | B1 | 4/2006 | Qing |
| 7,041,617 | B2 | 5/2006 | Jensen |
| 7,199,073 | B2 | 4/2007 | Martin |
| 7,226,886 | B2 | 6/2007 | Jayaratne |
| 7,294,599 | B2 | 11/2007 | Jensen |
| 7,312,283 | B2 | 12/2007 | Martin |
| 7,433,761 | B2 | 10/2008 | Battiste |
| 7,517,939 | B2 | 4/2009 | Yang |
| 7,531,606 | B2 | 5/2009 | Hendrickson |
| 7,598,327 | B2 | 10/2009 | Shaw |
| 7,601,665 | B2 | 10/2009 | McDaniel |
| 7,615,596 | B2 | 11/2009 | Burns |
| 7,619,047 | B2 | 11/2009 | Yang |
| 7,629,284 | B2 | 12/2009 | Jensen |
| 7,884,163 | B2 | 2/2011 | McDaniel |
| 7,906,597 | B2 | 3/2011 | Fouarge |
| 7,919,639 | B2 | 4/2011 | Murray |
| 8,077,309 | B2 | 12/2011 | Brown |
| 8,080,681 | B2 | 12/2011 | Murray |
| 8,088,871 | B2 | 1/2012 | Muruganandam |
| 8,114,946 | B2 | 2/2012 | Yang |
| 8,119,553 | B2 | 2/2012 | Yang |
| 8,242,221 | B2 | 8/2012 | McDaniel |
| 8,288,487 | B2 | 10/2012 | Yang |
| 8,309,485 | B2 | 11/2012 | Yang |
| 8,329,834 | B2 | 12/2012 | Masino |
| 8,536,391 | B2 | 9/2013 | Small |
| 8,623,973 | B1 | 1/2014 | McDaniel |
| 8,629,292 | B2 | 1/2014 | Buck |
| 8,680,218 | B1 | 3/2014 | Yang |
| 8,703,886 | B1 | 4/2014 | Yang |
| 8,821,800 | B2 | 9/2014 | Benham |
| 8,822,608 | B1 | 9/2014 | Bhandarkar |
| 9,040,642 | B2 | 5/2015 | Buck |
| 9,540,457 | B1 | 1/2017 | Ding |
| 10,030,086 | B1* | 7/2018 | Yang ..................... G01N 21/31 |
| 10,507,445 | B2 | 12/2019 | Buck |
| 2002/0156205 | A1 | 10/2002 | Long |
| 2004/0002420 | A1 | 1/2004 | Wu |
| 2005/0272891 | A1 | 12/2005 | Fouarge |
| 2010/0029877 | A1 | 2/2010 | Funaya |
| 2010/0317904 | A1 | 12/2010 | Small |
| 2014/0336345 | A1 | 11/2014 | Benham |
| 2015/0197582 | A1 | 7/2015 | McDaniel |
| 2016/0325252 | A1 | 11/2016 | Benham |
| 2016/0347887 | A1 | 12/2016 | Ege |
| 2019/0025200 | A1* | 1/2019 | Yang ................... B01J 19/0033 |

FOREIGN PATENT DOCUMENTS

| | | |
|---|---|---|
| EP | 0564948 A1 | 10/1993 |
| EP | 1316566 B1 | 3/2005 |
| EP | 1713840 B1 | 4/2019 |
| WO | 2004026455 A2 | 4/2004 |
| WO | 2006026493 A1 | 3/2006 |
| WO | 2014062643 A1 | 4/2014 |

OTHER PUBLICATIONS

Cotton, F. Albert, et al., "Advanced Inorganic Chemistry," Sixth Edition, cover page, title page, pp. ix-x, and book description, Mar. 30, 1999, John Wiley & Sons, Inc.

Hawley's Condensed Chemical Dictionary, Eleventh Edition, cover page, contents p. pp. 862-863, Van Nostrand Reinhold Company.

International Search Report and Written Opinion issued in corresponding application No. PCT/US2018/041430 dated Oct. 25, 2018, 19 pages.

(56) References Cited

OTHER PUBLICATIONS

International Search Report and Written Opinion issued in corresponding application No. PCT/US2019/023419 dated Jul. 15, 2019, 25 pages.
IUPAC Compendium of Chemical Terminology, 2nd Ed. 1997, pp. 1-1670.

* cited by examiner

US 11,735,293 B2

METHODS FOR DETERMINING TRANSITION METAL COMPOUND CONCENTRATIONS IN MULTICOMPONENT LIQUID SYSTEMS

REFERENCE TO RELATED APPLICATION

This application is a divisional application of U.S. patent application Ser. No. 16/808,492, filed on Mar. 4, 2020, now U.S. Pat. No. 11,170,874, which is a continuation application of U.S. patent application Ser. No. 16/006,899, filed on Jun. 13, 2018, now U.S. Pat. No. 10,679,734, which is a continuation-in-part application of U.S. patent application Ser. No. 15/939,446, filed on Mar. 29, 2018, now U.S. Pat. No. 10,507,445, the disclosures of which are incorporated herein by reference in their entirety.

FIELD OF THE INVENTION

The present disclosure concerns methods for determining the concentrations of transition metal compounds in solutions containing more than one transition metal compound, and more particularly relates to the use of UV-Vis (ultraviolet-visible) spectroscopy for simultaneously determining the respective concentrations of individual transition metal compounds.

BACKGROUND OF THE INVENTION

Polyolefins such as high density polyethylene (HDPE) homopolymer and linear low density polyethylene (LLDPE) copolymer can be produced using various combinations of catalyst systems and polymerization processes. In many olefin polymerization processes, a catalyst system containing more than one transition metal compound is utilized. Precise determination of the relative and absolute concentrations of each transition metal compound allows for better control of the polymerization processes and the resulting polymer products. It would be beneficial if real-time monitoring or measurement of the respective amount of each transition metal compound present in catalyst feed streams, catalyst systems, and polymerization reactor systems could be performed in order to improve the control of the polymerization process. Additionally, it would be beneficial to determine the respective concentrations of a first transition metal compound and a second transition metal compound in solutions where the UV-Vis spectrums of the first transition metal compound and the second transition metal compound overlap, and/or where the second transition metal compound is in large excess relative to the first transition metal compound. Accordingly, it is to these ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Methods for determining a first concentration of a first transition metal compound and a second concentration of a second transition metal compound in a solution containing the first transition metal compound and the second transition metal compound are disclosed herein. In accordance with an aspect of the present invention, one such method can comprise (i) providing a first reference absorbance profile ($F_1$) of the first transition metal compound in a first reference solution at a first known concentration, and a second reference absorbance profile ($F_2$) of the second transition metal compound in a second reference solution at a second known concentration, (ii) submitting a sample of the solution to a sample chamber, (iii) irradiating the sample in the chamber with a light beam at a wavelength in the UV-visible spectrum, (iv) generating a sample absorbance profile of the sample, and calculating a curve having the formula $\beta_1 F_1 + \beta_2 F_2$ to fit the sample absorbance profile to a least-squares regression fit value ($R^2$) of at least 0.9, wherein $\beta_1$ is a first weighting coefficient, $F_1$ is the first reference absorbance profile of the first transition metal compound in the first reference solution at the first known concentration, $\beta_2$ is a second weighting coefficient, and $F_2$ is the second reference absorbance profile of the second transition metal compound in the second reference solution at the second known concentration, and (v) multiplying the first known concentration with $\beta_1$ to determine the first concentration of the first transition metal compound in the solution, and multiplying the second known concentration with $\beta_2$ to determine the second concentration of the second transition metal compound in the solution.

In another aspect, a process for operating a polymerization reactor system is disclosed, and in this aspect, the process can comprise (I) contacting a catalyst system comprising a first transition metal compound, a second transition metal compound, an activator, and an optional co-catalyst, with an olefin monomer and an optional olefin comonomer in a reactor within the polymerization reactor system under polymerization reaction conditions to produce an olefin polymer, (II) determining a first concentration of the first transition metal compound and a second concentration of the second transition metal compound in a solution comprising the first transition metal compound and the second transition metal compound, and (III) adjusting a first flow rate of the first transition metal compound and/or a second flow rate of second transition metal compound into the reactor when the first concentration and/or the second concentration has reached a predetermined level (or adjusting the first flow rate of the first transition metal compound based on the first determined concentration and/or adjusting the second flow rate of the second transition metal compound based on the second determined concentration). In yet another aspect, a process for preparing a catalyst composition is disclosed, and in this aspect, the process can comprise (I) contacting a first transition metal compound, a second transition metal compound, a solid activator, and an optional co-catalyst (e.g., in a catalyst preparation vessel) to form the catalyst composition, (II) determining a first concentration of the first transition metal compound and a second concentration of the second transition metal compound in a solution containing the first transition metal compound and the second transition metal compound, the solution separated from (or obtained from) the catalyst composition, and (III) adjusting a relative amount of at least one component of the catalyst composition based on the first concentration and/or the second concentration (or based on the determined concentrations). In these and other aspects, the first concentration and the second concentration can be determined by any methodology disclosed herein.

Additionally, various polymerization reactor systems are disclosed herein. One such polymerization reactor system can comprise (A) a reactor configured to contact a catalyst system with an olefin monomer and an optional olefin comonomer under polymerization reaction conditions to produce an olefin polymer, (B) a catalyst preparation vessel configured to contact a first transition metal compound, a second transition metal compound, an activator, and an optional co-catalyst to form the catalyst system, and (C) an analytical system configured to determine a first concentration of the first transition metal compound and a second concentration of the second transition metal compound in a solution comprising the first transition metal compound and the second transition metal compound present within the polymerization reactor system. Consistent with particular aspects of this invention, the analytical system can comprise an ultraviolet-visible spectrometer.

Catalyst preparation systems also are disclosed herein. One such catalyst preparation system can comprise (a) a catalyst preparation vessel configured to contact a first transition metal compound, a second transition metal compound, and a solid activator (and a co-catalyst, if used) to form a catalyst composition, (b) an activator feed stream configured to introduce the solid activator into the catalyst preparation vessel, (c) a first transition metal compound feed stream configured to introduce the first transition metal compound into the catalyst preparation vessel, (d) a second transition metal compound feed stream configured to introduce the second transition metal compound into the catalyst preparation vessel, (e) a catalyst system feed stream configured to withdraw the catalyst composition from the catalyst preparation vessel (e.g., and to introduce the catalyst composition to a reactor), and (f) an analytical system configured to determine a first concentration of the first transition metal compound and a second concentration of the second transition metal compound in a solution comprising the first transition metal compound and the second transition metal compound, the solution separated from (or obtained from) the catalyst composition. If a co-catalyst is a component of the catalyst composition, the catalyst preparation system can further include a co-catalyst feed stream configured to introduce the co-catalyst into the catalyst preparation vessel. Moreover, the catalyst preparation system can further comprise (g) a controller that is configured to control a flow rate of the activator feed stream, a flow rate of the co-catalyst fees stream, a flow rate of the first transition metal compound feed stream, and/or a flow rate of the second transition metal compound feed stream into the catalyst preparation vessel based on, or according to, the first concentration and/or the second concentration determined by the analytical system.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The following figures form part of the present specification and are included to further demonstrate certain aspects of the present invention. The invention can be better understood by reference to one or more of these figures in combination with the detailed description of specific aspects presented herein.

DEFINITIONS

Figure 1:
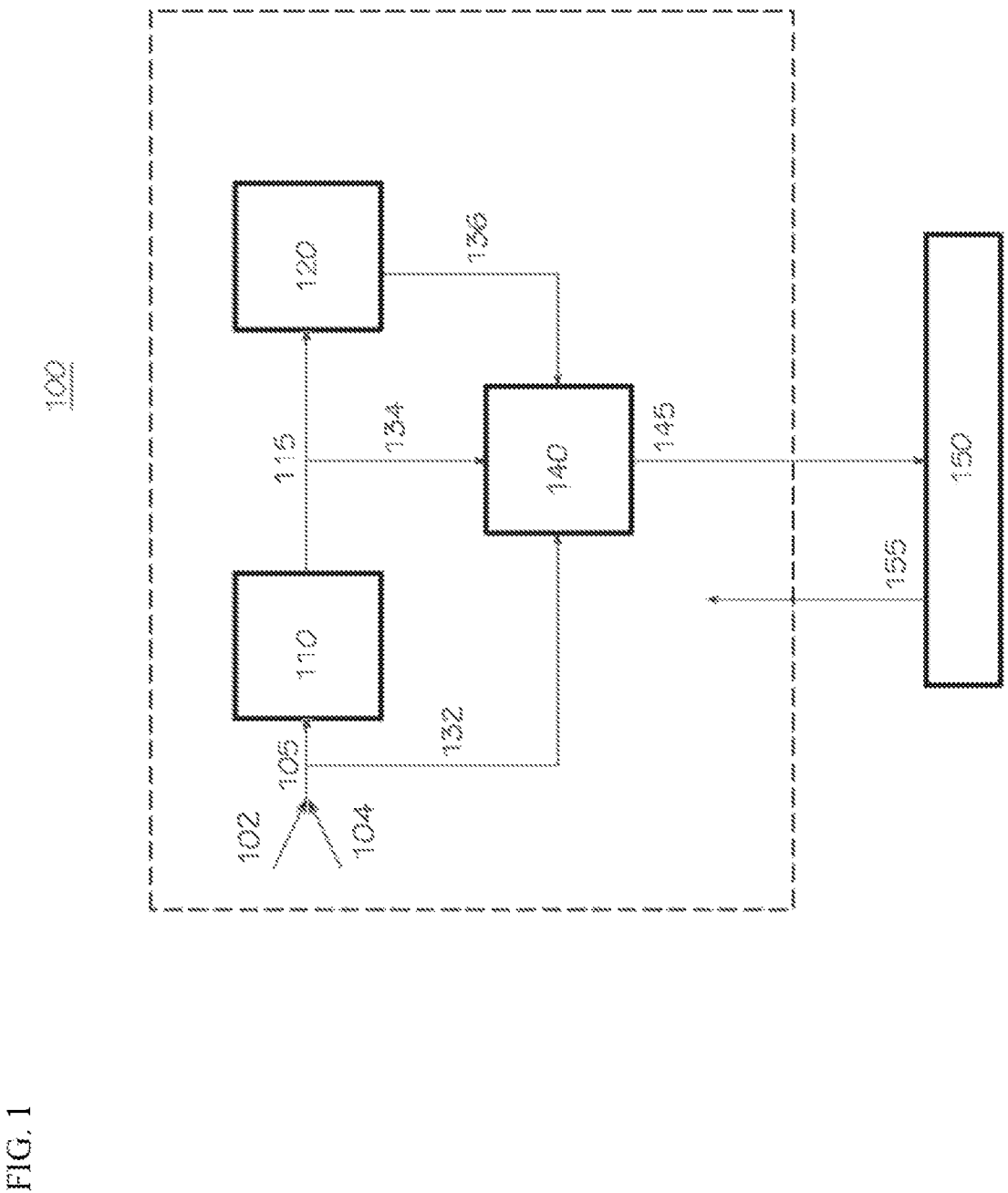
FIG. 1 illustrates a schematic block diagram of a polymerization reactor system consistent with aspects of this invention.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and/or feature disclosed herein, all combinations that do not detrimentally affect the systems, compositions, processes, and/or methods described herein are contemplated with or without explicit description of the particular combination. Additionally, unless explicitly recited otherwise, any aspect and/or feature disclosed herein can be combined to describe inventive features consistent with the present disclosure.

Unless explicitly stated otherwise in defined circumstances, all percentages, parts, ratios, and like amounts used herein are defined by weight.

In this disclosure, while systems, processes, and methods are often described in terms of "comprising" various components, devices, or steps, the systems, processes, and methods can also "consist essentially of" or "consist of" the various components, devices, or steps, unless stated otherwise.

The terms "a," "an," and "the" are intended to include plural alternatives, e.g., at least one. For instance, the disclosure of "a polymerization reactor," "a transition metal compound," or "a wavelength," is meant to encompass one, or mixtures or combinations of more than one, polymerization reactor, transition metal compound, or wavelength, unless otherwise specified.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

The term "about" means that amounts, sizes, formulations, parameters, and other quantities and characteristics are not and need not be exact, but can be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

Various numerical ranges are disclosed herein. When a range of any type is disclosed or claimed, the intent is to disclose or claim individually each possible number that such a range could reasonably encompass, including end points of the range as well as any sub-ranges and combinations of sub-ranges encompassed therein, unless otherwise specified. As a representative example, the present disclosure recites that the polymerization reaction conditions can comprise a polymerization reaction temperature in a range from about 60° C. to about 115° C. in certain aspects. By a disclosure that the temperature can be in a range from about 60° C. to about 115° C., the intent is to recite that the temperature can be any temperature within the range and, for example, can be equal to about 60° C., about 65° C., about 70° C., about 75° C., about 80° C., about 85° C., about 90° C., about 95° C., about 100° C., about 105° C., about 110° C., or about 115° C. Additionally, the temperature can be within any range from about 60° C. to about 115° C. (for example, the temperature can be in a range from about 70° C. to about 110° C.), and this also includes any combination of ranges between about 60° C. and about 115° C. Likewise, all other ranges disclosed herein should be interpreted in a manner similar to this example.

The term "polymer" is used herein generically to include olefin homopolymers, copolymers, terpolymers, and the like, as well as alloys and blends thereof. The term "polymer" also includes impact, block, graft, random, and alternating copolymers. A copolymer can be derived from an olefin monomer and one olefin comonomer, while a terpolymer can be derived from an olefin monomer and two olefin comonomers. Accordingly, "polymer" encompasses copolymers and terpolymers. Similarly, the scope of the term "polymerization" includes homopolymerization, copolymerization, and terpolymerization. Therefore, an ethylene polymer would include ethylene homopolymers, ethylene copolymers (e.g., ethylene/α-olefin copolymers), ethylene terpolymers, and the like, as well as blends or mixtures thereof. Thus, an ethylene polymer encompasses polymers often referred to in the art as LLDPE (linear low density polyethylene) and HDPE (high density polyethylene). As an example, an ethylene copolymer can be derived from ethylene and a comonomer, such as 1-butene, 1-hexene, or 1-octene. If the monomer and comonomer were ethylene and 1-hexene, respectively, the resulting polymer can be categorized as an ethylene/1-hexene copolymer. The term "polymer" also includes all possible geometrical configurations, if present and unless stated otherwise, and such configurations can include isotactic, syndiotactic, and random symmetries. The term "polymer" also is meant to include all molecular weight polymers, and is inclusive of lower molecular weight polymers or oligomers. The intent is for the term "polymer" to encompass oligomers (including dimers and trimers) derived from any olefin monomer disclosed herein (as well from an olefin monomer and one olefin comonomer, an olefin monomer and two olefin comonomers, and so forth).

The term "contacting" is used herein to describe systems, compositions, processes, and methods in which the components are contacted or combined together in any order, in any manner, and for any length of time, unless otherwise specified. For example, the components can be combined by blending or mixing, using any suitable technique.

A "solution" is meant to indicate that there is no visual precipitate at the conditions (e.g., temperature and pressure) of interest. For instance, typical laboratory testing conditions can include a temperature in the 20-25° C. range and a pressure of approximately 1 atm. Alternatively, the solution of two of more transition metal compounds can be tested at elevated temperature and pressure, such as at temperatures and pressures typical of solution polymerization processes, slurry polymerization processes, and the like.

The term "spectrometer" is used herein generically to include devices that may be referred to in the art as a spectrometer or a spectrophotometer, and the like.

As used herein, the term "near real-time" refers to a delay that is introduced by automated data processing between the occurrence of an event and the use of the processed data. For example, classifying an event as a near real-time event refers to the real-time event occurrence, minus the processing time, as nearly the time of the live event. That is, the time interval between when data is received for analysis and analysis is performed and displayed (e.g., on a computer screen or alternate device) or an activity is undertaken (e.g., adjusting a flow rate of the first and/or second transition metal compound), which is within 1 minute to within 10 minutes, for example, a time interval as short as 3 seconds to 3 minutes.

As used herein, the term "real-time" or "actual real-time" can refer to the instant capture of a measured item at the time of capture occurrence, e.g., the instantaneous or nearly instantaneous streaming or transmission of data or information. The real-time data can be UV-Vis analysis data or sensor reading data that can be provided instantly, such as within 2 seconds, to a computer system, to computer readable medium, or to a controller, and the like, as soon as the UV-Vis reading is obtained.

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are methods for determining the respective concentrations of a first transition metal compound and a second transition metal compound in solutions containing the first transition metal compound and the second transition metal compound, and related processes for operating polymerization reactor systems. Also disclosed herein are polymerization reactor systems comprising analytical systems for determining the respective concentrations of a first transition metal compound and a second transition metal compound in solutions containing the first transition metal compound and the second transition metal compound, and processes for operating such reactor systems. While not wishing to be bound by theory, it is believed that such reactor systems (and related methods) can offer improved control and/or real-time monitoring or measurement of the amount of the transition metal compounds present in catalyst component feed streams, catalyst systems, and polymerization reactor systems, ultimately resulting in improved quality control and consistency of the polymerization process. Beneficially, the reactor systems (and related methods) disclosed herein allow for determining the respective concentrations of the first transition metal compound and the second transition metal compound with a single test and with exceptional precision, even where the absorbance profiles of the first transition metal compound and the second transition metal compound overlap significantly, and/or where one of the first and second transition metal compounds is in large excess relative to the other. Advantageously, the reactor systems (and related methods) disclosed herein can be applied in circumstances where the respective absorbance profiles of the transition metal compounds cannot be deconvoluted or determined independently. Accordingly, since precise information on the respective concentrations of the first and second transition metal compounds can be determined, the polymerization reactor systems (and related methods) disclosed herein can permit real-time monitoring, control, adjustment, and/or fine tuning of the respective concentrations of the first and second transition metal compounds within a production run of an individual grade of polymer resin.

Methods for Determining the Concentrations of Transition Metal Compounds

Aspects of this invention are directed to methods for determining a first concentration of a first transition metal compound and a second concentration of a second transition metal compound in a solution comprising the first transition metal compound and the second transition metal compound. Such methods can comprise (or consist essentially of, or consist of) (i) providing a first reference absorbance profile ($F_1$) of the first transition metal compound in a first reference solution at a first known concentration, and a second reference absorbance profile ($F_2$) of the second transition metal compound in a second reference solution at a second known concentration, (ii) submitting a sample of the solution to a sample chamber, (iii) irradiating the sample in the chamber with a light beam at a wavelength (one or more than one) in the UV-visible spectrum, (iv) generating (e.g., collecting or outputting) a sample absorbance profile of the sample, and calculating a curve having the formula $\beta_1 F_1 + \beta_2 F_2$ to fit the sample absorbance profile to a least-squares regression fit value ($R^2$) of at least 0.9, wherein $\beta_1$ is a first weighting coefficient, $F_1$ is the first reference absorbance profile of the first transition metal compound in the first reference solution at the first known concentration, $\beta_2$ is a second weighting coefficient, and $F_2$ is the second reference absorbance profile of the second transition metal compound in the second reference solution at the second known concentration, and (v) multiplying the first known concentration with $\beta_1$ to determine the first concentration of the first transition metal compound in the solution, and multiplying the second known concentration with $\beta_2$ to determine the second concentration of the second transition metal compound in the solution.

Generally, the features of the methods disclosed herein (e.g., the transition metal compounds, the solution, the wavelength(s) of the light beam, the absorbance profiles, and the curve, among others) are independently described herein, and these features can be combined in any combination to further describe the disclosed methods. Moreover, other process steps can be conducted before, during, and/or after any of the steps listed in the disclosed methods, unless stated otherwise.

In step (i), a first reference absorbance profile ($F_1$) of the first transition metal compound in a first reference solution at a first known concentration, and a second reference absorbance profile ($F_2$) of the second transition metal compound in a second reference solution at a second known concentration are provided. The first reference solution and the second reference solution can contain the first transition metal compound and the second transition metal compound, respectively, at any suitable concentration, and can contain any suitable solvent. Likewise, the solution is not limited to the respective concentrations of the first transition metal compound and the second transition metal compound in the solution, and is not limited to any particular solvent.

Generally, the solution comprises the first transition metal compound, the second transition metal compound, and a hydrocarbon solvent, although the methods disclosed herein can be employed for other solvent types, such as chlorinated hydrocarbons, ethers, alcohols, and so forth. Typical hydrocarbon solvents can include, but are not limited to, propane, cyclohexane, cyclohexene, isobutane, n-butane, n-pentane, isopentane, neopentane, n-hexane, 1-hexene, toluene, and the like, as well as combinations thereof. Other suitable hydrocarbon solvents can include the ISOPAR® family of mixed aliphatic hydrocarbon solvents, such as, for example, ISOPAR® C, ISOPAR® E, ISOPAR® G, ISOPAR® H, ISOPAR® L, ISOPAR® M, and the like, as well as mixtures thereof. While not wishing to be bound by theory, it is believed that the type of transition metal compounds and the type of solvent present in the solution can impact the wavelength or wavelengths to be utilized in the systems and methods/processes disclosed herein. In particular aspects of this invention, the systems and methods/processes disclosed herein are well suited for determining the respective concentrations of the first transition metal compound and the second transition metal compound in a solution containing the first transition metal compound, a second transition metal compound, and a hydrocarbon solvent. The hydrocarbon solvent can comprise, for instance, 1-hexene, isobutane, toluene, or cyclohexene, and the like, as well as mixtures or combinations thereof.

In one aspect, the solution (containing the first transition metal compound and the second transition metal compound), the first reference solution, and the second reference solution can comprise the same solvent (e.g., the same hydrocarbon solvent), while in another aspect, at least two of the solution (containing the first transition metal compound and the second transition metal compound), the first reference solution, and the second reference solution can comprise a different solvent (e.g., a different hydrocarbon solvent).

The selection of the solvent can affect the absorbance profiles of certain transition metal compounds. Thus, it can be beneficial for the first reference solution and the second reference solution to contain the same solvent as that of the solution (containing the first transition metal compound and the second transition metal compound). In such aspects, any solvent effects can be minimized, leading to improved accuracy in determining the respective concentrations of the first transition metal compound and the second transition metal compound.

Any of the absorbance profiles described herein (e.g., the sample absorbance profile, the first reference absorbance profile ($F_1$), and the second reference absorbance profile ($F_2$)) can comprise an absorbance peak at a single wavelength in some aspects of this invention. Alternatively, any absorbance profiles described herein can comprise an absorbance curve (peaks and/or areas under curves as a function of wavelength) over a range of wavelengths, such as from 200 nm to 750 nm, or from 300 nm to 600 nm, and so forth. Thus, data from the respective absorbance curves over a range of wavelengths can be used for determining the respective concentrations of the first transition metal compound and the second transition metal compound in the solution. Additionally or alternatively, any absorbance profiles described herein can comprise an absorbance curve (peaks and/or areas under curves as a function of wavelength) over a subset of wavelengths spanning less than 350 nm, less than 300 nm, less than 250 nm, less than 200 nm, or less than 150 nm. Thus, data from the respective absorbance curves over a specific subset of wavelengths ranges can be used for determining the respective concentrations of the first transition metal compound and the second transition metal compound in the solution. Other suitable absorbance profile options are readily apparent from this disclosure.

Generally, the path lengths used for the first reference absorbance profile ($F_1$), the second reference absorbance profile ($F_2$), and the sample absorbance profile often can be the same, although this is not a requirement In step (ii), a sample of the solution containing the first and second transition metal compounds (at least two transition metal compounds) is submitted to a sample chamber. The sample chamber can be a flow cell, although any suitable design and configuration of the sample chamber can be used. In further aspects, the solution can contain more than two different transition metal compounds. Accordingly, the solution containing the transition metal compounds can contain two different transition metal compounds, or more than two different transition metal compounds. As a non-limiting example, the solution can contain two metallocene compounds: one bridged metallocene compound and one unbridged metallocene compound, two different bridged metallocene compounds, or two different unbridged metallocene compounds.

The sample in the sample chamber can be irradiated with a light beam at a wavelength in the UV-visible spectrum in step (iii). Such can be accomplished, for instance, by a UV-Vis spectrometer, discussed hereinbelow. The wavelength of the light beam can be a single wavelength, or more than one wavelength, such as a range of wavelengths (e.g., a 200 nm wavelength range or a 300 nm wavelength range). In one aspect, the wavelength of the light beam can comprise wavelengths in the visible spectrum (from 380 nm to 780 nm). In another aspect, the wavelength of the light beam can comprise wavelengths in the 200 nm to 750 nm range. Yet, in another aspect, the wavelength of the light beam can comprise wavelengths in the 300 nm to 600 nm range. Thus, any suitable wavelength range can be employed depending upon, for instance, the specific transition metal compounds or the specific hydrocarbon solvent. Often, step (iii) can be performed in the 300-600 nm wavelength range. Moreover, if desired, the UV-Vis light/radiation can be filtered in some aspects of this invention.

In step (iv), a sample absorbance profile of the sample, which contains a solution of the first and second transition metal compounds, is generated. Then, a curve having the formula $\beta_1 F_1 + \beta_2 F_2$ can be calculated to fit the sample absorbance profile to a least-squares regression fit value ($R^2$) of at least 0.9. In the curve having the formula $\beta_1 F_1 + \beta_2 F_2$, $\beta_1$ is a first weighting coefficient, $F_1$ is the first reference absorbance profile of the first transition metal compound in the first reference solution at the first known concentration, $\beta_2$ is a second weighting coefficient, and $F_2$ is the second reference absorbance profile of the second transition metal compound in the second reference solution at the second known concentration.

While not limited thereto, the curve having the formula $\beta_1 F_1 + \beta_2 F_2$ can be determined (and, thus, the first weighting coefficient ($\beta_1$) and the second weighting coefficient ($\beta_2$) can be determined) over any suitable range of wavelengths to fit the sample absorbance profile. For instance, the range of wavelengths can be from 200 nm to 750 nm; alternatively, from 300 nm to 600 nm; alternatively, from 350 nm to 600 nm; or alternatively, from 350 nm to 550 nm. Additionally or alternatively, the curve having the formula $\beta_1 F_1 + \beta_2 F_2$ can be determined (and, thus, the first weighting coefficient ($\beta_1$)

and the second weighting coefficient ($\beta_2$) can be determined) over any suitable subset of wavelengths to fit the sample absorbance profile. For instance, the subset of wavelengths can span less than 350 nm, less than 300 nm, less than 250 nm, less than 200 nm, or less than 100 nm. Hence, in particular aspects of this invention, the curve having the formula $\beta_1 F_1 + \beta_2 F_2$ can be determined (and, thus, the first weighting coefficient ($\beta_1$) and the second weighting coefficient ($\beta_2$) can be determined) over a subset of wavelengths spanning less than 350 nm, less than 300 nm, less than 250 nm, less than 200 nm, or less than 100 nm, in the 200 nm to 750 nm wavelength range, or in the 300 nm to 600 nm wavelength range, to fit the sample absorbance profile. Other wavelength options are readily apparent from this disclosure.

While not being limited thereto, in some aspects of this invention, the generating and calculating operations in step (iv), independently, can be conducted over a broad spectrum of wavelengths, such as in the 300-600 nm range, and the first reference and second reference absorbance profiles, independently, can be conducted over the same or a different spectrum of wavelengths, such as in the 300-600 nm range, but not limited thereto.

Using the techniques disclosed herein can result in the curve having the formula $\beta_1 F_1 + \beta_2 F_2$ providing an excellent fit to the sample absorbance profile, with a least-squares regression fit value ($R^2$) of at least 0.9, and more often, at least 0.95, or at least 0.98. In many instances, the curve and the sample absorbance profile overlap so completely that the plots cannot be distinguished. Thus, least-squares regression fit values ($R^2$) of at least 0.99, of at least 0.999, or of at least 0.9995, can be readily achieved.

In step (v), the first known concentration and $\beta_1$ are multiplied to determine the first concentration of the first transition metal compound in the solution, and the second known concentration and $\beta_2$ are multiplied to determine the second concentration of the second transition metal compound in the solution.

In some instances, actual absorbance profiles (sample, first reference, second reference) can be generated, which can be collected or outputted, such as in the form of a plot of the absorbance as a function of the wavelength, which can be viewed on a monitor or computer screen, or printed in hard copy form. In other instances, the absorbance profiles are generated, but not collected or outputted into a viewable form. For example, data from the sample absorbance profile, the first reference absorbance profile, and the second absorbance profile—e.g., absorbance as a function of the wavelength—can be used to directly determine the first weighting coefficient ($\beta_1$) and the second weighting coefficient ($\beta_2$), for subsequent conversion to the respective concentrations of the first and second transition metal concentrations.

The step of calculating the curve having the formula $\beta_1 F_1 + \beta_2 F_2$ can comprise any suitable method or technique that fits the sample absorbance profile—whether from a narrow subset of wavelength ranges or from a broad spectrum of wavelengths—and determines the first weighting coefficient (PO and the second weighting coefficient ($\beta_2$), for subsequent conversion to the respective concentrations of the first and second transition metal concentrations. These steps can be performed manually, or can be configured to automatically determine the respective concentrations of the first and second transition metal compounds once the sample absorbance profile has been generated. Thus, steps (iv) and (v) can be performed sequentially or simultaneously, and can be performed manually or can be computerized (e.g., for automatic determination of the respective concentrations of the first and second transition metal compounds in the solution).

Generally, the respective concentrations of the first and second transition metal compounds in the first and second reference solutions are not limited to any particular range. However, in certain aspects, the first known concentration of the first transition metal compound in the first reference solution can be such that the absorbance peak at a single wavelength in the first reference absorbance profile (for instance, the absorbance peak at 380 nm) can be less than 2, less than 1, or less than 0.5. In particular aspects, the first known concentration of the first transition metal compound in the first reference solution can be such that the absorbance peak at a single wavelength in the first reference absorbance profile can be in a range from about 0.1 to about 2, from about 0.1 to about 1, from about 0.3 to about 1, or from about 0.5 to about 1. These same concentration and absorbance ranges can apply to second transition metal compound in the second reference solution.

Likewise, the respective concentrations of the first and second transition metal compound in the solution are not limited to any particular range. For instance, the concentration of the first transition metal compound in the solution and the concentration of the second transition metal compound in the solution, independently, can be less than about 5 wt. %, less than about 2 wt. %, less than about 1 wt. %, less than about 0.8 wt. %, less than about 0.5 wt. %, less than about 0.2 wt. %, less than about 0.1 wt. %, less than about 0.05 wt. %, or less than about 0.01 wt. %. Illustrative and non-limiting ranges for the concentration of the first transition metal compound in the solution and the concentration of the second transition metal compound in the solution, independently, can include from about 0.01 wt. % to about 5 wt. %, from about 0.01 wt. % to about 1 wt. %, from about 0.01 wt. % to about 0.5 wt. %, from about 0.05 to about 0.2 wt. %, from about 0.01 wt. % to about 0.1 wt. %, or from about 0.1 wt. % to about 0.3 wt. %.

Alternatively, or in addition to, determining the absolute concentration of the first transition metal compound and the second transition metal compound, the methods described herein can be used to determine the relative concentrations (or relative amounts) of the first and second transition metal compounds. In certain aspects, the weight ratio of the first transition metal compound to the second transition metal compound (first:second) in the solution can be less than about 1:1, less than about 1:4, less than about 1:10, or less than about 1:20. In other aspects, the weight ratio of the first transition metal compound to the second transition metal compound in the solution can be in a range from about 50:1 to about 1:50, from about 10:1 to about 1:10, from about 2:1 to about 1:2, from about 1:20 to about 1:1, from about 1:100 to about 1:2, from about 1:50 to about 1:5, from about 1:50 to about 1:10, or from about 1:20 to about 1:10.

The methods disclosed herein are applicable to a wide variety of circumstances where the concentrations of transition metal compounds in a solution (or a mixture, from which a solution can be derived) may be of interest. In one aspect, the solution comprising the first and second transition metal compounds can be a feed stream to a catalyst preparation vessel. The catalyst preparation vessel can be any vessel or apparatus that is capable of contacting (e.g., mixing or blending) two or more components of a catalyst system to form a catalyst system. Any two or more components can be precontacted for a suitable period of time period prior to contacting with the remaining components to form the finished catalyst system, which can then be transferred from the catalyst preparation vessel to the reactor, as needed. Often, in the catalyst preparation vessel, the transition metal compounds (two or more) and an activator (one or more) are contacted, or alternatively, the transition metal compounds (two or more), an activator (one or more), and a co-catalyst are contacted, to form the catalyst system.

In another aspect, the solution comprising the first and second transition metal compounds can be a liquid (or homogeneous) catalyst system comprising the transition metal compounds. The catalyst system can contain, in addition to the transition metal compounds, components including a liquid activator (or a solution of a liquid activator), such as MAO, as well as a liquid co-catalyst (or a solution of a co-catalyst), if desired in the catalyst system.

In yet another aspect, the solution comprising the first and second transition metal compounds can be a solution from a polymerization reactor (e.g., a solution reactor or slurry reactor) in which the solids or particulates from a sample stream (of a mixture from the reactor) have been removed, such as via sieving, filtering, centrifuging, and the like, and including combinations or two or more of these techniques, as well as any other suitable technique for removing solids or particulates from a mixture to result in a solution. Therefore, in this aspect, the solution comprising the first transition metal compound and the second transition metal compound can be a solution prepared from a sample mixture from a polymerization reactor.

In still another aspect, the solution comprising the first and second transition metal compounds can be a solution from a heterogeneous or supported catalyst system stream, in which the solids or particulates from a sample stream (of the catalyst system mixture) have been removed by any suitable technique, or any technique disclosed herein. Therefore, in this aspect, the solution comprising the first transition metal compound and the second transition metal compound can be a solution prepared from a sample mixture of a heterogeneous catalyst system, such as from a catalyst preparation vessel.

Polymerization Reactor Systems

Various polymerization reactor systems and processes for operating or controlling such systems are disclosed and described herein. For instance, in one aspect, a process for operating a polymerization reactor system can comprise (I) contacting a catalyst system comprising a first transition metal compound, a second transition metal compound, an activator, and an optional co-catalyst, with an olefin monomer and an optional olefin comonomer in a reactor within the polymerization reactor system under polymerization reaction conditions to produce an olefin polymer, (II) determining a first concentration of the first transition metal compound and a second concentration of the second transition metal compound in a solution comprising the first transition metal compound and the second transition metal compound, the first concentration and the second concentration determined via the methods described herein, and (III) adjusting a first flow rate of the first transition metal compound and/or a second flow rate of second transition metal compound into the reactor when the first concentration and/or the second concentration has reached a predetermined level. Hence, the first flow rate (or feed rate) of the first transition metal compound can be adjusted, manually and/or automatically, based on the first determined concentration, and/or the second flow rate (or feed rate) of the second transition metal compound can be adjusted, manually and/or automatically, based on the second determined concentration. Generally, the features of the processes for operating polymerization reactor systems disclosed herein (e.g., the transition metal compounds, the catalyst system, the olefin monomer, the olefin comonomer, the reactor, the method of determining the respective concentrations of the first and second transition metal compounds, and the flow rate control of the first and second transition metal compounds, among others) are independently described herein, and can be combined in any combination to further describe the disclosed processes. Moreover, other steps can be conducted before, during, and/or after any of the steps listed in the disclosed processes, unless stated otherwise.

Step (II) is directed to determining a first concentration of the first transition metal compound and a second concentration of the second transition metal compound in a solution comprising the first transition metal compound and the second transition metal compound. Step (II) can comprise the steps of (i) providing a first reference absorbance profile ($F_1$) of the first transition metal compound in a first reference solution at a first known concentration, and a second reference absorbance profile ($F_2$) of the second transition metal compound in a second reference solution at a second known concentration, (ii) submitting a sample of the solution to a sample chamber, (iii) irradiating the sample in the chamber with a light beam at a wavelength (one or more than one) in the UV-visible spectrum, (iv) generating (e.g., collecting or outputting) a sample absorbance profile of the sample, and calculating a curve having the formula $\beta_1 F_1 + \beta_2 F_2$ to fit the sample absorbance profile to a least-squares regression fit value ($R^2$) of at least 0.9, wherein $\beta_1$ is a first weighting coefficient, $F_1$ is the first reference absorbance profile of the first transition metal compound in the first reference solution at the first known concentration, $\beta_2$ is a second weighting coefficient, and $F_2$ is the second reference absorbance profile of the second transition metal compound in the second reference solution at the second known concentration, and (v) multiplying the first known concentration with $\beta_1$ to determine the first concentration of the first transition metal compound in the solution, and multiplying the second known concentration with $\beta_2$ to determine the second concentration of the second transition metal compound in the solution. Accordingly, the specific features relating to step (II) can be the same as those disclosed and described herein as it pertains to methods for determining the respective concentrations of the first and second transition metal compounds in a solution containing the first and second transition metal compounds.

The processes disclosed herein are applicable to a wide variety of circumstances where the concentration of a transition metal compound in a solution (or a mixture, from which a solution can be obtained) may be of interest. In one aspect, the solution comprising the first transition metal compound and the second transition metal compounds can be a feed stream to a catalyst preparation vessel. In this aspect, the first flow rate and/or the second flow rate into the reactor can be controlled by adjusting a flow rate of a feed stream to the catalyst preparation vessel, and/or by adjusting a relative flow rate (ratio of the flow rate of the first transition metal compound to the flow rate of the second transition metal compound—first:second transition metal compound) to the catalyst preparation vessel, and/or by adjusting a total flow rate of the catalyst system exiting the catalyst preparation vessel and entering the reactor.

As an example, if the concentration of the first transition metal compound is below a target concentration, the first flow rate of the first transition metal compound into the reactor can be increased by increasing a relative flow rate (ratio of the flow rate of the first transition metal compound to the flow rate of the second transition metal compound) to the catalyst preparation vessel. This can be accomplished, for instance, by increasing the feed rate of the first transition metal compound to the catalyst preparation vessel, while keeping constant the feed rate of the second transition metal compound to the catalyst preparation vessel.

As another example, if the concentration of the first transition metal compound is below a target concentration, the first flow rate of the first transition metal compound into the reactor can be increased by increasing a relative flow rate (ratio of the flow rate of the first transition metal compound to the flow rate of the second transition metal compound) to the reactor. This can be accomplished, for instance, by increasing the first flow rate of the first transition metal compound to the reactor, while keeping constant the second flow rate of the second transition metal compound to the reactor.

In another aspect, the catalyst system can be a liquid (or homogeneous) catalyst system, and the solution comprising the first transition metal compound and the second transition metal compound can be a sample of the liquid catalyst system. In this aspect, the first flow rate and/or the second flow rate can be controlled by adjusting a relative flow rate (ratio of the first flow rate of the first transition metal compound to the second flow rate of the second transition metal compound) to the reactor, and/or by adjusting a total flow rate of the liquid catalyst system entering the reactor.

In yet another aspect, the polymerization reactor system comprises a polymerization reactor (e.g., a solution polymerization reactor or a slurry polymerization reactor), and the solution comprising the first transition metal compound and the second transition metal compound can be a solution prepared from a sample of the mixture from the polymerization reactor. In this aspect, the first flow rate and/or the second flow rate can be controlled by adjusting a relative flow rate (ratio of the first flow rate of the first transition metal compound to the second flow rate of the second transition metal compound) to the reactor, and/or by adjusting a total flow rate of the catalyst system entering the polymerization reactor. The solids or particulates from the sample of the mixture from the polymerization reactor can be removed by any suitable technique. Optionally, cooling the sample of the mixture can be beneficial. This process can be useful for determining the respective amounts of the first and second transition metal compounds that are not impregnated in, on, or associated with any solid catalyst components and/or polymer particulates, e.g., to determine the respective amounts (or percentages) of the first and second transition metal compounds that are present in solution.

In still another aspect, the catalyst system can be a heterogeneous or supported catalyst system, and the solution comprising the first transition metal compound and the second transition metal compound can be a solution obtained from a sample stream of the heterogeneous or supported catalyst system. In this aspect, the first flow rate and/or the second flow rate can be controlled by adjusting a relative flow rate (ratio of the first flow rate of the first transition metal compound to the second flow rate of the second transition metal compound) to the reactor, and/or by adjusting a total flow rate of the catalyst system entering the polymerization reactor. As above, this process can be useful in determining the respective amounts of the first and second transition metal compounds that are not impregnated in, on, or associated with the solid catalyst components of the catalyst system, e.g., to determine the respective amounts (or percentages) of the first and second transition metal compounds that are present in solution.

Consistent with aspects disclosed herein, in step (III), when the first concentration and/or the second concentration in the solution has reached a predetermined level, the first flow rate of the first transition metal compound and/or the second flow rate of second transition metal compound into the reactor can be adjusted. The predetermined level can be readily ascertained by one of skill in the art depending upon, for instance, the historic and the prevailing conditions in the polymerization reactor system. As non-limiting examples, a predetermined level can be a decrease of a certain percentage of the first concentration of the first transition metal compound (e.g., beyond that which is deemed allowable during normal on-prime production), or the increase of a certain percentage of the first concentration of the first transition metal compound in the solution (e.g., beyond which is deemed allowable during normal on-prime production). For instance, the target concentration of the first transition metal compound in the solution can be 0.1 wt. %, and the predetermined lower and upper control limits can be 0.09 wt. % and 0.11 wt. %, respectively, for normal on-prime production. If the measured first concentration of the first transition metal compound in the solution was 0.08 wt. %, then the feed rate of the first transition metal compound to the catalyst preparation vessel (and in turn, the first flow rate to the polymerization reactor) can be increased to bring the concentration of the first transition metal compound to an acceptable level within the predetermined limits of 0.09-0.11 wt. %. Conversely, if the concentration of the first transition metal in the solution was too high (e.g., 0.12+ wt. %), then the first flow rate of the first transition metal compound can be decreased to bring the concentration to an acceptable level within the predetermined limits. In like manner, if the second concentration of the second transition metal compound in the solution has reached a predetermined level, similar adjustments can be made to the second flow rate of second transition metal compound into the reactor as needed.

In another aspect of this invention, a polymerization reactor system is provided, and in this aspect, the polymerization reactor system can comprise (A) a reactor configured to contact a catalyst system with an olefin monomer and an optional olefin comonomer under polymerization reaction conditions to produce an olefin polymer, (B) a catalyst preparation vessel configured to contact a first transition metal compound, a second transition metal compound, an activator, and an optional co-catalyst to form the catalyst system, and (C) an analytical system configured to determine a first concentration of the first transition metal compound and a second concentration of the second transition metal compound in a solution comprising the first transition metal compound and the second transition metal compound present within the polymerization reactor system. Generally, the features of any of the polymerization reactor systems disclosed herein (e.g., the polymerization reactor, the catalyst system, the olefin monomer (and olefin comonomer, if any), the polymerization conditions, the olefin polymer, the catalyst preparation vessel, the analytical system, among others) are independently described herein, and these features can be combined in any combination to further describe the disclosed polymerization reactor systems. Moreover, other devices or reactor system components in addition to the reactor, the catalyst preparation vessel, and the analytical system, can be present in the disclosed polymerization reactor systems, unless stated otherwise. Additionally, the catalyst system can be contacted with an olefin monomer and an olefin comonomer (e.g., contacted with ethylene and an α-olefin comonomer, such as 1-hexene) in the polymerization reactor in certain aspects contemplated herein.

The analytical system (C) can include any analytical system or device that is capable of determining a first concentration of the first transition metal compound and a second concentration of the second transition metal compound in a solution that contains both the first transition metal compound and the second transition metal compound. For instance, the analytical system can include an ultraviolet-visible (UV-Vis) spectrometer (e.g., alone or in combination with another analytical device/method, such as a fluorescence spectroscopy method; a UV-Vis-NIR system; and so forth). In one aspect of this invention, the analytical system can include an ultraviolet-visible spectrometer with an integrated computer system, such that the spectrometer and integrated computer system are capable of measuring (or configured to measure) a sample absorbance profile of the solution; capable of calculating (or configured to calculate) a curve having the formula $\beta_1 F_1 + \beta_2 F_2$ to fit the sample absorbance profile to a least-squares regression fit value ($R^2$) of at least 0.9, wherein $\beta_1$ is a first weighting coefficient, $F_1$ is a first reference absorbance profile of the first transition metal compound in a first reference solution at a first known concentration, $\beta_2$ is a second weighting coefficient, and $F_2$ is a second reference absorbance profile of the second transition metal compound in a second reference solution at a second known concentration; and capable of multiplying (or configured to multiply) the first known concentration with $\beta_1$ to determine the first concentration of the first transition metal compound in the solution, and multiplying the second known concentration with $\beta_2$ to determine the second concentration of the second transition metal compound in the solution. In this aspect, the UV-Vis spectrometer has a "built-in" computer system, performing the absorbance measurements and subsequent calculations to convert the absorbance data into the respective concentrations of the first and second transition metal compounds. In further aspects, the UV-Vis spectrometer and integrated computer can be capable of storing reference absorbance profiles, such as $F_1$ (the first reference absorbance profile of the first transition metal compound in a first reference solution at a first known concentration) and $F_2$ (the second reference absorbance profile of the second transition metal compound in a second reference solution at a second known concentration).

In another aspect of this invention, the analytical system can include an ultraviolet-visible spectrometer and an external computer system, such that the ultraviolet-visible spectrometer is capable of measuring (or configured to measure) a sample absorbance profile of the solution, and the external computer system is capable of calculating (or configured to calculate) a curve having the formula $\beta_1 F_1 + \beta_2 F_2$ to fit the sample absorbance profile to a least-squares regression fit value ($R^2$) of at least 0.9, and capable of multiplying (or configured to multiply) the first known concentration with $\beta_1$ to determine the first concentration of the first transition metal compound in the solution, and multiplying the second known concentration with $\beta_2$ to determine the second concentration of the second transition metal compound in the solution. In this aspect, the UV-Vis can perform the absorbance measurement of the solution and generate the absorbance data and profile, but an external computer system can take the output from the UV-Vis and determine the respective concentrations of the first and second transition metal compounds.

If desired, the analytical system can further comprise a filter assembly designed to filter the sample of the solution containing the first and second transition metal compounds before analysis by the UV-Vis spectrometer.

As described herein, the absorbance profiles (e.g., the sample absorbance profile, the first reference absorbance profile, and the second reference absorbance profile) independently can comprise an absorbance peak at a single wavelength in some aspects of this invention. Additionally or alternatively, the absorbance profiles independently can comprise an absorbance curve (peaks and/or areas under curves, as a function of wavelength) over a range of wavelengths, such as from 200 nm to 750 nm, or from 300 nm to 600 nm, and so forth. Thus, data from an absorbance curve over the range of wavelengths can be used for determining the respective concentrations of the first and second transition metal compounds in the solution. Additionally or alternatively, the absorbance profiles independently can comprise an absorbance curve (peaks and/or areas under curves, as a function of wavelength) over a subset of wavelengths spanning less than 350 nm, less than 300 nm, less than 250 nm, less than 200 nm, or less than 150 nm. Thus, data from the absorbance curves over a specific subset of wavelengths ranges can be used for determining the respective concentrations of the first and second transition metal compounds in the solution. Other suitable absorbance profile options and combinations are readily apparent from this disclosure.

For example, and while not being limited thereto, the sample absorbance profile can be generated and the curve having the formula $\beta_1 F_1 + \beta_2 F_2$ to fit the sample absorbance profile can be generated, independently, over any suitable wavelength range, such as in the 300-600 nm range or a subset thereof, and the first reference and second reference absorbance profiles, independently, can be conducted over the same or a different spectrum of wavelengths, such as in the 300-600 nm range or a subset thereof, but not limited thereto.

The analytical system and techniques disclosed herein can result in the curve having the formula $\beta_1 F_1 + \beta_2 F_2$ providing an excellent fit to the sample absorbance profile, with a least-squares regression fit value ($R^2$) of at least 0.9, and more often, at least 0.95, or at least 0.98. In many instances, the curve and the sample absorbance profile overlap so completely that the plots cannot be distinguished. Thus, least-squares regression fit values ($R^2$) of at least 0.99, of at least 0.999, or of at least 0.9995, can be readily achieved.

The catalyst preparation vessel (B) in the polymerization reactor system can include any vessel or apparatus that is capable of contacting (e.g., mixing or blending) two or more components of a catalyst system to form the catalyst system. The catalyst preparation vessel can be a mixing tank or other suitable stirred tank or vessel. The catalyst system can be delivered from the catalyst preparation vessel to the reactor, as needed. Often, in the catalyst preparation vessel, the transition metal compounds (two or more) and an activator (one or more) are contacted, or alternatively, the transition metal compounds (two or more), an activator (one or more), and a co-catalyst are contacted, to form the catalyst system. Multicomponent catalyst preparation vessels and methods are disclosed in, for instance, U.S. Pat. No. 7,615,596 (e.g., a pre-contactor), which is incorporated herein by reference in its entirety.

Optionally, the polymerization reactor system can further comprise a controller (D) that is capable of controlling (or configured to control) a first flow rate of the first transition metal compound and/or a second flow rate of second transition metal compound into the reactor based on, or according to, the first concentration and/or the second concentration determined by the analytical system. Thus, the polymerization reactor system can comprise a reactor, a catalyst preparation vessel, an analytical system, and a controller. The controller, which can comprise any suitable processing unit or computer system, can be used to analyze the data regarding the respective concentrations of the first and second transition metal compounds in the solution, and adjust the first flow rate and/or second flow rate into the reactor based on the determined concentrations. In another aspect, the controller can be programmed with an algorithm to control the first flow rate and/or the second flow rate into the reactor based on the concentrations determined by the analytical system. As an example, if the second concentration determined by the analytical system is too low, the second flow rate of the second transition metal compound into the reactor can be increased by the controller. In yet another aspect, the controller operative to control the first flow rate and/or the second flow rate can comprise a controller operative to receive information on the respective concentrations of the first and second transition metal compounds, to identify new target first and/or transition metal compound concentrations (e.g., increase or decrease the first flow rate and/or second flow to achieve a desired impact on the first or second transition metal compound concentration), and to provide a control signal to adjust the first flow rate and/or second flow rate into the reactor system accordingly.

The controller can be operated on an as-needed basis, at set time intervals, or continuously, depending upon the requirements of the reactor system. Thus, it is contemplated that the respective concentrations of the first and second transition metal compounds can be monitored and/or adjusted and/or controlled continuously. Accordingly, in particular aspects consistent with this invention, the polymerization reactor system and the controller can operate in real-time or near real-time, such that the respective concentrations of the first and second transition metal compounds can be determined, and that determined concentrations can be used, instantaneously or nearly instantaneously, to adjust the first flow rate of the first transition metal compound and/or the second flow rate of the second transition metal compound into the reactor.

The controller or computing device can be implemented using a personal computer, a network computer, a server, a mainframe, or other similar microcomputer-based workstation. The controller or computing device can comprise any computer operating environment, such as hand-held devices, multiprocessor systems, microprocessor-based or programmable sender electronic devices, minicomputers, mainframe computers, and the like. The controller or computing device also can be practiced in distributed computing environments where tasks are performed by remote processing devices. Furthermore, the controller or computing device can comprise a mobile terminal, such as a smart phone, a cellular telephone, a cellular telephone utilizing wireless application protocol (WAP), personal digital assistant (PDA), intelligent pager, portable computer, a hand held computer, a conventional telephone, a wireless fidelity (Wi-Fi) access point, or a facsimile machine. The aforementioned systems and devices are examples, and the controller or computing device can comprise other systems or devices. Controller or computing device also can be implemented via a system-on-a-chip (SOC) where each and/or many of the components illustrated above can be integrated onto a single integrated circuit. Such an SOC device can include one or more processing units, graphics units, communications units, system virtualization units and various application functionalities, all of which can be integrated (or "burned") onto the chip substrate as a single integrated circuit. Other controller methodologies and devices are readily apparent to one of skill in the art in view of this disclosure.

Controllers of the systems disclosed herein can control the first flow rate and/or the second flow rate of the first and second transition metal compound, respectively, into or within the polymerization reactor system by any method that affords precise and near instantaneous control of the respective concentrations of the first and second transition metal compounds.

The systems disclosed herein are applicable to a wide variety of circumstances where the respective concentrations of first and second transition metal compounds in a solution (or a mixture, from which a solution can be obtained), which contains the first transition metal compound and a second transition metal compound, may be of interest. In one aspect, the solution comprising the first transition metal compound and a second transition metal compound can be a feed stream to the catalyst preparation vessel. In this aspect, the controller can control the first flow rate and/or the second flow rate into the reactor by adjusting a flow rate of the feed stream to the catalyst preparation vessel, and/or by adjusting a relative flow rate of the first and second transition metal compounds rate (ratio of first:second transition metal compound) to the catalyst preparation vessel, and/or by adjusting a flow rate of the catalyst system exiting the catalyst preparation vessel and entering the reactor.

In another aspect, the catalyst system can be a liquid (or homogeneous) catalyst system, and the solution comprising the first and second transition metal compounds can be a sample of the liquid catalyst system. In this aspect, the controller can control the first flow rate and/or the second flow rate into the reactor by adjusting a relative flow rate of the first and second transition metal compounds to the reactor, and/or by adjusting a flow rate of the liquid catalyst system entering the reactor.

In yet another aspect, the polymerization reactor system can comprise a polymerization reactor (e.g., a solution reactor or a slurry reactor) containing a reaction mixture, and the solution comprising the first and second transition metal compounds can be a solution prepared or separated from a sample stream from the polymerization reactor. In this aspect, the controller can control the first flow rate and/or the second flow rate into the reactor by adjusting a relative flow rate of the first and second transition metal compounds to the reactor, and/or by adjusting a flow rate of the catalyst system entering the reactor. As described herein, the solids or particulates from the sample stream (reaction mixture) can be removed by any suitable technique. Optionally, cooling the sample stream can be beneficial. This process can be useful in determining the respective amounts of the first and second transition metal compounds that are not impregnated in, on, or associated with the solid catalyst components and/or polymer particulates, e.g., to determine the respective amounts of the first and second transition metal compounds (or the fractions thereof) that are present in solution.

In still another aspect, the solution comprising the first and second transition metal compounds can be a solution obtained or separated from a sample stream of a heterogeneous or supported catalyst system feed stream. In this aspect, the first flow rate and/or the second flow rate into the reactor can be controlled by adjusting a relative flow rate to the reactor, and/or by adjusting a flow rate of the catalyst system entering the reactor. As above, this process can be useful in determining the respective amounts of the first and second transition metal compounds that are not impregnated in, on, or associated with the solid catalyst components of the catalyst system, e.g., to determine the respective amounts of the first and second transition metal compounds (or fractions thereof) that are present in solution.

A representative polymerization reactor system 100 consistent with aspects of this invention is illustrated in FIG. 1. The polymerization reactor system 100 includes a catalyst preparation vessel 110, a reactor 120, an analytical system 140, and a controller 150. The analytical system 140 can include a UV-Vis spectrometer as described herein. The polymerization reactor system 100 of FIG. 1 includes a first transition metal compound solution feed stream 102 and a second transition metal compound solution feed stream 104 which form a combined transition metal compound solution feed stream 105 to the catalyst preparation vessel (separate feed streams to the catalyst preparation vessel for other catalyst components are not shown). In other aspects not shown in FIG. 1, feed streams 102 and 104 can be independently fed directly to the catalyst preparation vessel 110 and/or to the reactor 120. As shown in FIG. 1, a sample stream 132 from the combined feed stream 105 can be submitted to the analytical system 140 for determination of the respective concentrations of the first and second transition metal compounds in the combined feed stream 105 prior to its entry into the catalyst preparation vessel 110.

The polymerization reactor system 100 includes a catalyst system feed stream 115 from the catalyst preparation vessel 110 to the reactor 120. The catalyst system feed stream 115 can be a liquid (or homogeneous) or a supported (or heterogeneous) catalyst system containing the first and second transition metal compounds. A sample stream 134 from the catalyst system feed stream 115 can be submitted to the analytical system 140 for determination of the respective concentrations of the first and second transition metal compounds in the solution portion of the feed stream (e.g., solids or particulates in the catalyst system feed stream 115 can be removed prior to analysis).

The polymerization reactor system 100 includes a sample stream 136 from the reactor 120. The sample stream 136 from the reactor 120 can be submitted to the analytical system 140 for determination of the respective concentrations of the first and second transition metal compounds in the solution portion of the reactor contents (e.g., solids or particulates in the reactor sample stream 136 can be removed prior to analysis).

Information or data 145 on the concentrations of the first and second transition metal compounds from the analytical system 140 can be provided to controller 150, which can then control or adjust 155 a flow rate of the combined feed stream 105, and/or a flow rate of the catalyst system feed stream 115. Alternatively, or additionally, controller 150 can independently control or adjust 155 a flow rate of the first transition metal compound solution feed stream 102 and/or the second transition metal compound solution feed stream 104 to control or adjust 155 a relative flow rate of feed streams 102 and 104. Thus, the controller 150 controls or adjusts 155 the flow rates of the first and second transition metal compounds into the reactor 120 based on, or according to, the concentrations determined by the analytical system 140. For example, if the concentration determined by the analytical system 140 is too low, the flow rate of one or more feed streams can be increased by the controller 150.

The disclosed polymerization reactor systems and methods of operating same are intended to encompass any olefin polymerization process using any/all types of polymerization reactors and polymerization reaction conditions. As used herein, "polymerization reactor" includes any polymerization reactor capable of polymerizing (inclusive of oligomerizing) olefin monomers and comonomers (one or more than one comonomer, if used) to produce homopolymers, copolymers, terpolymers, and the like. The various types of polymerization reactors include those that can be referred to as a slurry reactor, gas-phase reactor, solution reactor, high pressure reactor, tubular reactor, autoclave reactor, and the like, including combinations thereof. The polymerization conditions for the various reactor types are well known to those of skill in the art. Gas phase reactors can comprise fluidized bed reactors or staged horizontal reactors. Slurry reactors can comprise vertical or horizontal loops. High pressure reactors can comprise autoclave or tubular reactors. These reactor types generally can be operated continuously. Continuous processes can use intermittent or continuous polymer product discharge. Polymerization reactor systems and processes also can include partial or full direct recycle of unreacted monomer, unreacted comonomer, and/or diluent.

Polymerization reactor systems disclosed herein can comprise one type of polymerization reactor or multiple reactors of the same or different type. For instance, the polymerization reactor system can comprise a solution reactor, a gas-phase reactor, a slurry reactor, or a combination of two or more of these reactors. Production of polymers in multiple reactors can include several stages in at least two separate polymerization reactors interconnected by a transfer device making it possible to transfer the polymer resulting from the first polymerization reactor into the second reactor. The polymerization conditions in one of the reactors can be different from the operating conditions of the other reactor(s). Alternatively, polymerization in multiple reactors can include the manual transfer of polymer from one reactor to subsequent reactors for continued polymerization. Multiple reactor systems can include any combination including, but not limited to, multiple loop reactors, multiple gas phase reactors, a combination of loop and gas phase reactors, multiple high pressure reactors, or a combination of high pressure with loop and/or gas phase reactors. The multiple reactors can be operated in series, in parallel, or both.

According to one aspect, the polymerization reactor system can comprise at least one loop slurry reactor, e.g., comprising vertical or horizontal loops. Monomer, diluent, catalyst, and optional comonomer can be continuously fed to a loop reactor where polymerization occurs. Generally, continuous processes can comprise the continuous introduction of monomer/comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer and/or comonomer. Various technologies can be used for this separation step including, but not limited to, flashing that can include any combination of heat addition and pressure reduction, separation by cyclonic action in either a cyclone or hydrocyclone, or separation by centrifugation.

A typical slurry polymerization process (also known as the particle form process) is disclosed, for example, in U.S. Pat. Nos. 3,248,179, 4,501,885, 5,565,175, 5,575,979, 6,239,235, 6,262,191, 6,833,415, and 8,822,608, each of which is incorporated herein by reference in its entirety.

Suitable diluents used in slurry polymerization include, but are not limited to, the monomer being polymerized and hydrocarbons that are liquids under reaction conditions.

Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used, such as can be employed in the bulk polymerization of propylene to form polypropylene homopolymers.

According to yet another aspect, the polymerization reactor system can comprise at least one gas phase reactor (e.g., a fluidized bed reactor). Such reactor systems can employ a continuous recycle stream containing one or more monomers continuously cycled through a fluidized bed in the presence of the catalyst under polymerization conditions. A recycle stream can be withdrawn from the fluidized bed and recycled back into the reactor. Simultaneously, polymer product can be withdrawn from the reactor and new or fresh monomer can be added to replace the polymerized monomer. Such gas phase reactors can comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790, 5,436,304, 7,531,606, and 7,598,327, each of which is incorporated by reference in its entirety herein.

According to still another aspect, the polymerization reactor system can comprise a high pressure polymerization reactor, e.g., can comprise a tubular reactor or an autoclave reactor. Tubular reactors can have several zones where fresh monomer, initiators, or catalysts are added. Monomer can be entrained in an inert gaseous stream and introduced at one zone of the reactor. Initiators, catalysts, and/or catalyst components can be entrained in a gaseous stream and introduced at another zone of the reactor. The gas streams can be intermixed for polymerization. Heat and pressure can be employed appropriately in such high pressure polymerization reactors to obtain optimal polymerization reaction conditions.

According to yet another aspect, the polymerization reactor system can comprise a solution polymerization reactor, wherein the monomer/comonomer can be contacted with the catalyst composition by suitable stirring or other means. A carrier comprising an inert organic diluent or excess monomer can be employed. If desired, the monomer/comonomer can be brought in the vapor phase into contact with the catalytic reaction product, in the presence or absence of liquid material. The polymerization zone can be maintained at temperatures (e.g., up to between 150° C. and 180° C.) and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

In some aspects, the polymerization reactor system can comprise any combination of a raw material feed system, a feed system for catalyst and/or catalyst components, and/or a polymer recovery system, including continuous systems. In other aspects, suitable reactor systems can comprise systems for feedstock purification, catalyst storage and preparation, extrusion, reactor cooling, polymer recovery, fractionation, recycle, storage, loadout, laboratory analysis, and process control.

Polymerization conditions that can be monitored, adjusted, and/or controlled for efficiency and to provide desired polymer properties can include, but are not limited to, reactor temperature, reactor pressure, catalyst system flow rate into the reactor, monomer flow rate (and comonomer, if employed) into the reactor, monomer concentration in the reactor, olefin polymer output rate, recycle rate, hydrogen flow rate (if employed), reactor cooling status, and the like. Polymerization temperature can affect catalyst productivity, polymer molecular weight, and molecular weight distribution. A suitable polymerization temperature can be any temperature below the de-polymerization temperature according to the Gibbs Free energy equation. Typically, this includes from about 60° C. to about 280° C., for example, from about 60° C. to about 185° C., from about 60° C. to about 115° C., or from about 130° C. to about 180° C., depending upon the type of polymerization reactor, the polymer grade, and so forth. In some reactor systems, the polymerization reactor temperature generally can be within a range from about 70° C. to about 110° C., or from about 125° C. to about 175° C.

Suitable pressures will also vary according to the reactor and polymerization type. The pressure for liquid phase polymerizations in a loop reactor typically can be less than 1000 psig (6.9 MPa). The pressure for gas phase polymerization usually can be in the 200 psig to 500 psig range (1.4 MPa to 3.4 MPa). High pressure polymerization in tubular or autoclave reactors generally can be conducted at about 20,000 psig to 75,000 psig (138 MPa to 517 MPa). Polymerization reactors can also be operated in a supercritical region occurring at generally higher temperatures and pressures (for instance, above 92° C. and 700 psig (4.83 MPa)). Operation above the critical point of a pressure/temperature diagram (supercritical phase) can offer advantages to the polymerization reaction process.

The concentration of the reactants entering the polymerization reactor can be controlled to produce resins with certain physical and mechanical properties. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, stereoregularity, crack growth, long chain branching, and rheological measurements.

Aspects contemplated herein also are directed to, and encompass, the polymers (or oligomers) produced by any of the polymerization reactor systems and methods disclosed herein. Articles of manufacture can be formed from, and/or can comprise, the polymers (or oligomers) produced in accordance with the systems and methods described herein.

Catalyst Systems

The methods, processes, and reactor systems disclosed herein are applicable to any catalyst system suitable for the polymerization of an olefin monomer, but are not limited thereto. Herein, a "catalyst system" also can be referred to as a "catalyst composition" or a "catalyst mixture." The first and second transition metal compounds independently can comprise, for example, a transition metal (one or more than one) from Groups 3-12 of the Periodic Table of the Elements (*Chemical and Engineering News,* 63(5), 27, 1985). In one aspect, the first and/or second transition metal compound can comprise a Group 3, 4, 5, or 6 transition metal, or a combination of two or more transition metals. The first and/or second transition metal compound(s) independently can comprise chromium, vanadium, titanium, zirconium, hafnium, or a combination thereof, in some aspects, or can comprise chromium, titanium, zirconium, hafnium, or a combination thereof, in other aspects. Accordingly, the first and/or second transition metal compound(s) independently can comprise chromium, or titanium, or zirconium, or hafnium, either singly or in combination. Moreover, catalyst systems containing more than two transition metal compounds are contemplated herein, and these additional transition metal compounds (e.g., a third transition metal compound) independently can comprise any suitable transition metal, such as chromium, titanium, zirconium, hafnium, vanadium, or a combination thereof.

In certain aspects of this invention, the first and/or second transition metal compound(s), independently, can comprise any suitable non-metallocene compound. Generally, the methods, processes, and reactor systems disclosed herein are most applicable to transition metal compounds, such as non-metallocene compounds, where the absorbance characteristics of the first transition metal compound and the second transition metal compound overlap, and cannot be de-convoluted.

Illustrative and non-limiting examples of suitable transition metal compounds encompassed herein can include the following compounds (R and R'=halide or $C_1$-$C_{18}$ hydrocarbyl group, n=an integer from 0 to 4, Ph=phenyl, tBu=tert-butyl, py=pyridine):

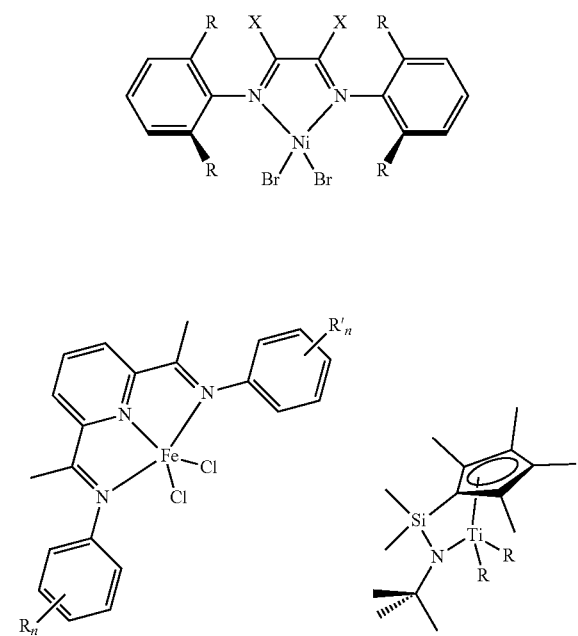

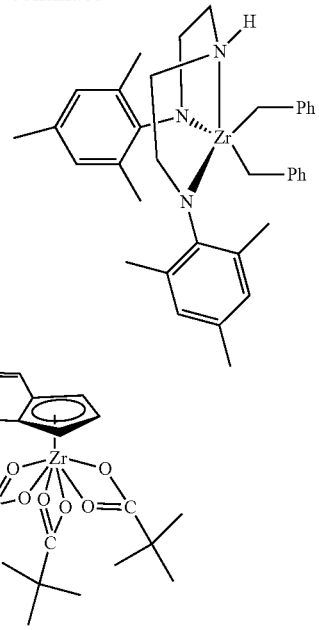

Alternatively or additionally, in certain aspects, the first and/or second transition metal compound(s) independently can comprise a metallocene compound, and the metallocene compound can comprise an unbridged metallocene compound. In one aspect, the metallocene compound can comprise an unbridged zirconium or hafnium based metallocene compound and/or an unbridged zirconium and/or hafnium based dinuclear metallocene compound. In another aspect, the metallocene compound can comprise an unbridged zirconium or hafnium based metallocene compound containing two indenyl groups or a cyclopentadienyl and an indenyl group. In yet another aspect, the metallocene compound can comprise an unbridged zirconium or hafnium based metallocene compound containing two indenyl groups. In still another aspect, the metallocene compound can comprise an unbridged zirconium or hafnium based metallocene compound containing a cyclopentadienyl and an indenyl group.

In an aspect, the metallocene compound can comprise an unbridged zirconium based metallocene compound containing two indenyl groups or a cyclopentadienyl and an indenyl group, while in another aspect, the metallocene compound can comprise a dinuclear unbridged metallocene compound with an alkenyl linking group.

Illustrative and non-limiting examples of unbridged metallocene compounds that are suitable for use as transition metal compounds described herein can include the following compounds (Ph=phenyl, stereochemistry not shown):

(1)

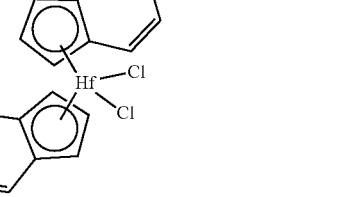

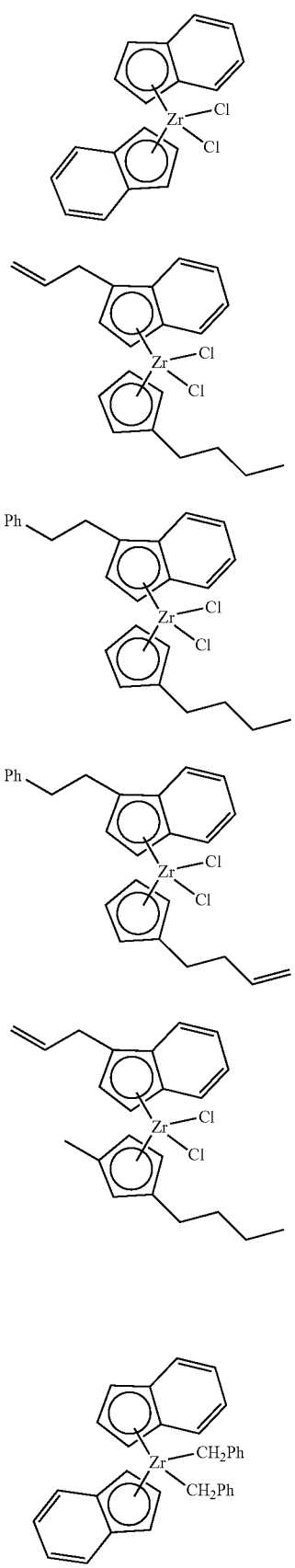

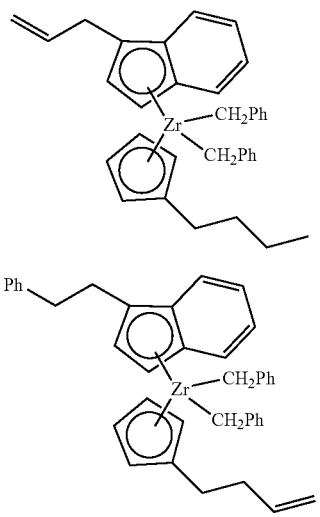

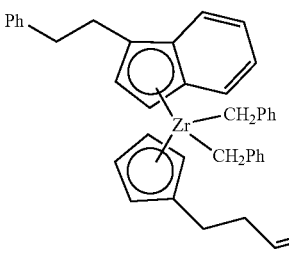

and the like, as well as combinations thereof.

The first and/or second transition metal compound(s) is/are not limited solely to unbridged metallocene compounds such as described above, or to suitable unbridged metallocene compounds disclosed in U.S. Pat. Nos. 7,199,073, 7,226,886, 7,312,283, and 7,619,047, which are incorporated herein by reference in their entirety. For example, the first and/or second transition metal compound(s) can comprise an unbridged dinuclear metallocene compound, such as those described in U.S. Pat. Nos. 7,919,639 and 8,080,681, the disclosures of which are incorporated herein by reference in their entirety. Illustrative and non-limiting examples of dinuclear metallocene compounds suitable for use in the present invention can include the following compounds (stereochemistry not shown):

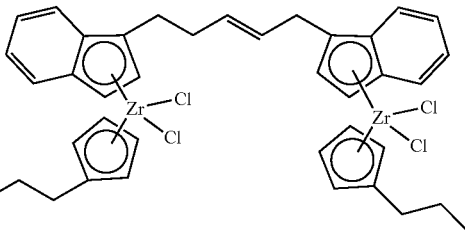

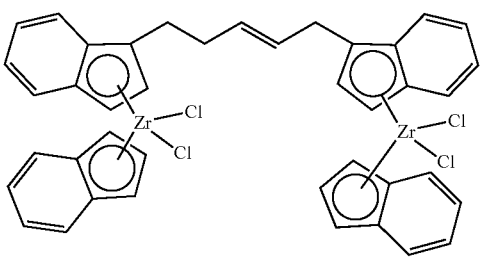

and the like, as well as combinations thereof.

Additionally or alternatively, the first and/or second transition metal compound(s) independently can comprise a bridged metallocene compound. In one aspect, the bridged metallocene compound can comprise a bridged zirconium or hafnium based metallocene compound. In another aspect, the bridged metallocene compound can comprise a bridged zirconium or hafnium based metallocene compound with an alkenyl substituent. In yet another aspect, the bridged metallocene compound can comprise a bridged zirconium or hafnium based metallocene compound with an alkenyl substituent and a fluorenyl group. In still another aspect, the bridged metallocene compound can comprise a bridged zirconium or hafnium based metallocene compound with a cyclopentadienyl group and a fluorenyl group, and with an alkenyl substituent on the bridging group and/or on the cyclopentadienyl group.

In an aspect, the bridged metallocene compound can comprise a single atom bridged metallocene compound with a fluorenyl group. In another aspect, the bridged metallocene compound can comprise a single atom bridged metallocene compound with a fluorenyl group and either a cyclopentadienyl group or an indenyl group. In yet another aspect, the bridged metallocene compound can comprise a single atom bridged metallocene compound with a fluorenyl group and a cyclopentadienyl group. In still another aspect, the bridged metallocene compound can comprise a single atom bridged metallocene compound with a fluorenyl group and an indenyl group.

In these and other aspects, the bridged metallocene compound can contain an aryl substituent (e.g., a phenyl group) on the bridging atom. Additionally or alternatively, the bridged metallocene compound can contain an alkenyl substituent, for example, on the bridging atom, and/or on the fluorenyl group, and/or on the cyclopentadienyl or indenyl group.

Illustrative and non-limiting examples of suitable bridged metallocene compounds encompassed herein can include the following compounds (Me=methyl, Ph=phenyl, t-Bu=tert-butyl, stereochemistry not shown):

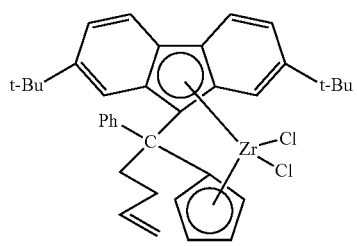
(14)

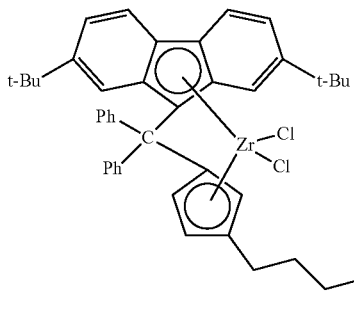
(15)

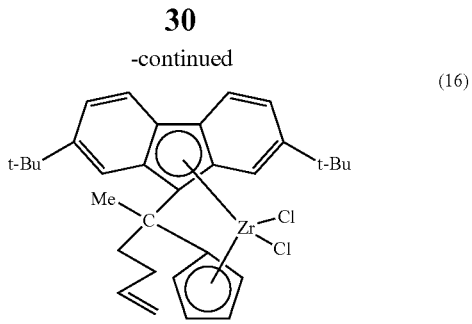
(16)

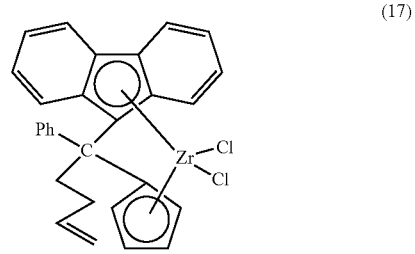
(17)

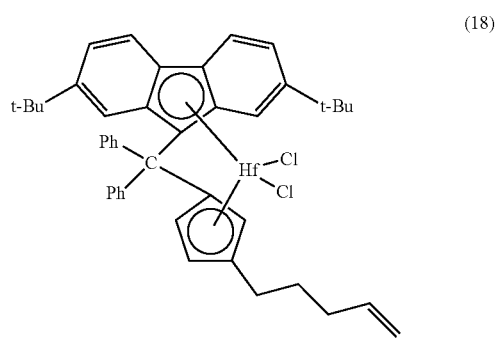
(18)

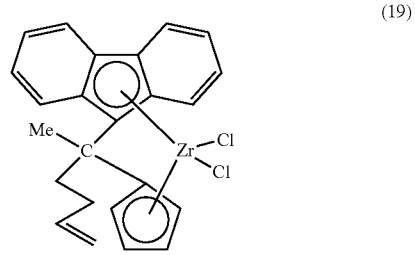
(19)

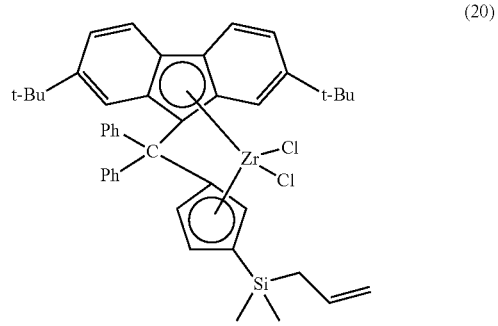
(20)

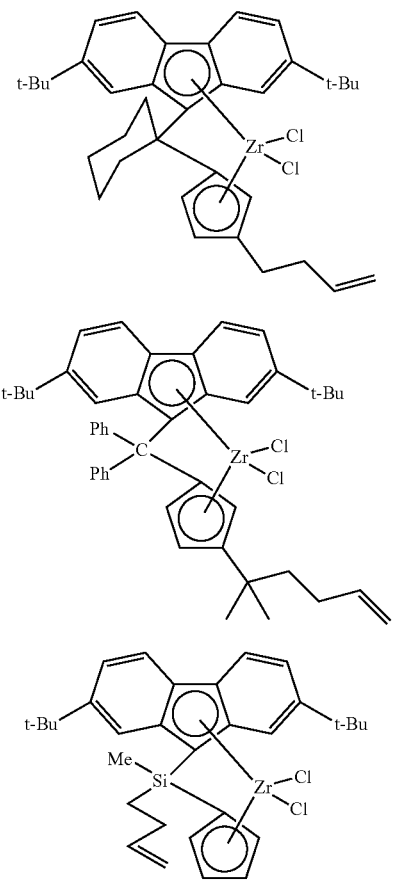
(21)
(22)
(23)
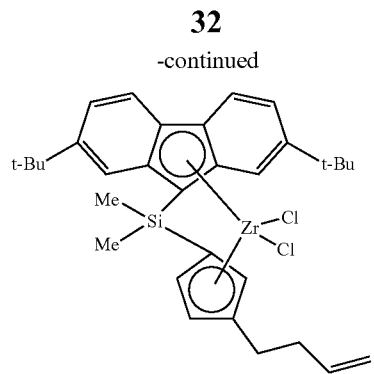
(24)
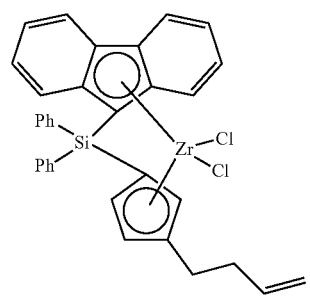
(25)
and the like, as well as combinations thereof.
Further examples of bridged metallocene compounds that are suitable for use as described herein can include, but are not limited to, the following compounds (stereochemistry not shown):
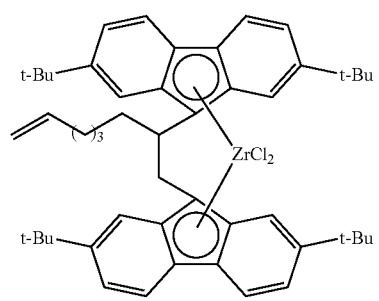
(26)
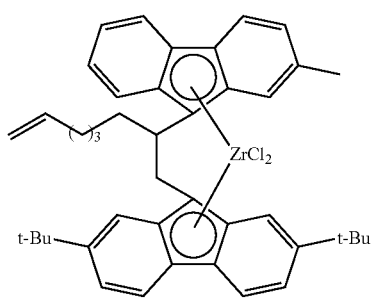
(27)
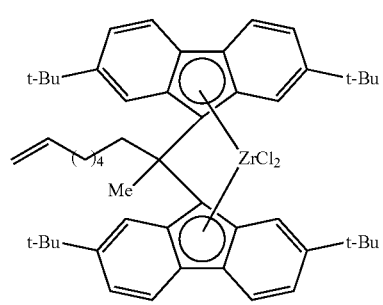
(28)

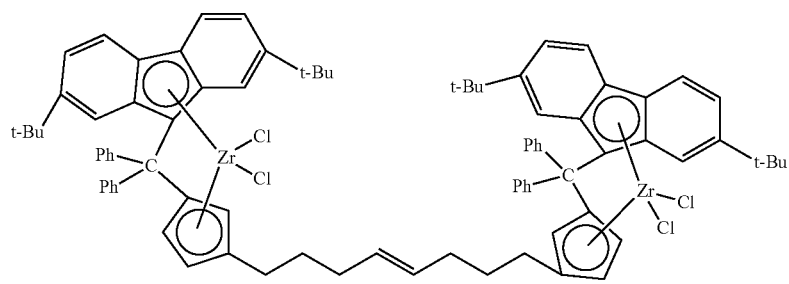

(29)

and the like, as well as combinations thereof.

The first and/or second transition metal compound(s) is/are not limited solely to the bridged metallocene compounds such as described above. Other suitable bridged metallocene compounds are disclosed in U.S. Pat. Nos. 7,026,494, 7,041,617, 7,226,886, 7,312,283, 7,517,939, 7,619,047, 8,288,487, 8,329,834, 8,629,292, and 9,040,642, all of which are incorporated herein by reference in their entirety.

The catalyst system, in addition to the first transition metal compound and the second transition metal compound, can comprise an activator (one or more) and an optional co-catalyst. Illustrative activators can include, but are not limited to, aluminoxane compounds, organoboron or organoborate compounds, ionizing ionic compounds, activator-supports (e.g., a solid oxide treated with an electron-withdrawing anion), and the like, or combinations thereof. Commonly used polymerization co-catalysts can include, but are not limited to, metal alkyl, or organometal, co-catalysts, with the metal encompassing boron, aluminum, and the like. For instance, alkyl boron and/or organoaluminum (e.g., alkyl aluminum) compounds often can be used as co-catalysts in a catalyst system. Representative compounds can include, but are not limited to, tri-n-butyl borane, tripropylborane, triethylborane, trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, including combinations thereof.

Co-catalysts that can be used in the catalyst systems of this invention are not limited to the co-catalysts described above. Other suitable co-catalysts are well known to those of skill in the art including, for example, those disclosed in U.S. Pat. Nos. 3,242,099, 4,794,096, 4,808,561, 5,576,259, 5,807,938, 5,919,983, 7,294,599 7,601,665, 7,884,163, 8,114,946, and 8,309,485, which are incorporated herein by reference in their entirety.

Solid Oxides

In some aspects, the catalyst system can contain a solid oxide. Generally, the solid oxide can comprise oxygen and one or more elements selected from Group 2, 3, 4, 5, 6, 7, 8, 9, 10, 11, 12, 13, 14, or 15 of the periodic table, or comprise oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example, the solid inorganic oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr.

Suitable examples of solid oxide materials or compounds that can be used as components of a catalyst system can include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof.

The solid oxide can encompass oxide materials such as alumina, "mixed oxide" compounds thereof such as silica-alumina, and combinations or mixtures of more than one solid oxide material. Mixed oxides such as silica-alumina can be single or multiple chemical phases with more than one metal combined with oxygen to form the solid oxide. Examples of mixed oxides that can be used herein include, but are not limited to, silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, and the like, or a combination thereof. Silica-coated aluminas are encompassed herein; such oxide materials are described in, for example, U.S. Pat. No. 7,884,163, the disclosure of which is incorporated herein by reference in its entirety.

The percentage of each oxide in a mixed oxide can vary depending upon the respective oxide materials. As an example, a silica-alumina typically has an alumina content from 5% by weight to 95% by weight. According to one aspect, the alumina content of the silica-alumina can be from 5% alumina by weight to 50% alumina by weight, or from 8% to 30% alumina by weight. In another aspect, high alumina content silica-alumina compounds can be employed, in which the alumina content of these silica-alumina materials typically ranges from 60% alumina by weight to 90% alumina by weight, or from 65% alumina by weight to 80% alumina by weight.

In one aspect, the solid oxide can comprise silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, or a combination thereof; alternatively, silica-alumina; alternatively, silica-coated alumina; alternatively, silica-titania; alternatively, silica-zirconia; alternatively, alumina-titania; alternatively, alumina-zirconia; alternatively, zinc-aluminate; alternatively, alumina-boria; alternatively, silica-boria; alternatively, aluminum phosphate; alternatively, aluminophosphate; alternatively, aluminophosphate-silica; or alternatively, titania-zirconia.

In another aspect, the solid oxide can comprise silica, alumina, titania, zirconia, magnesia, boria, zinc oxide, a mixed oxide thereof, or any mixture thereof. For instance, the solid oxide can comprise silica, alumina, titania, or a combination thereof; alternatively, silica; alternatively, alumina; alternatively, titania; alternatively, zirconia; alternatively, magnesia; alternatively, boria; or alternatively, zinc oxide.

In some aspects, the solid oxide can have a pore volume greater than 0.1 cc/g, or alternatively, greater than 0.5 cc/g. Often, the solid oxide can have a pore volume greater than 1.0 cc/g. Additionally, or alternatively, the solid oxide can have a surface area greater than 100 m$^2$/g; alternatively, greater than 250 m$^2$/g; or alternatively, greater than 350 m$^2$/g. For example, the solid oxide can have a surface area of from 100 to 1000 m$^2$/g, from 200 to 800 m$^2$/g, or from 250 to 600 m$^2$/g.

Activator-Supports

The present invention encompasses various catalyst systems which can contain an activator-support. In one aspect, the activator-support can comprise a solid oxide treated with an electron-withdrawing anion. Alternatively, in another aspect, the activator-support can comprise a solid oxide treated with an electron-withdrawing anion, the solid oxide containing a Lewis-acidic metal ion. Non-limiting examples of suitable activator-supports are disclosed in, for instance, U.S. Pat. Nos. 7,294,599, 7,601,665, 7,884,163, 8,309,485, 8,623,973, and 8,703,886, which are incorporated herein by reference in their entirety.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form an activator-support, either singly or in combination, can include, but are not limited to, silica-alumina, silica-titania, silica-zirconia, alumina-titania, alumina-zirconia, zinc-aluminate, alumina-bona, silica-boria, aluminophosphate-silica, titania-zirconia, and the like. The solid oxide used herein also can encompass oxide materials such as silica-coated alumina, as described in U.S. Pat. No. 7,884,163.

Accordingly, in one aspect, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another aspect, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. In another aspect, the solid oxide can comprise silica, alumina, titania, zirconia, magnesia, boria, zinc oxide, any mixed oxide thereof, or any combination thereof. In yet another aspect, the solid oxide can comprise silica-alumina, silica-coated alumina, silica-titania, silica-zirconia, alumina-boria, or any combination thereof. In still another aspect, the solid oxide can comprise alumina, silica-alumina, silica-coated alumina, or any mixture thereof alternatively, alumina; alternatively, silica-alumina; or alternatively, silica-coated alumina.

The silica-alumina or silica-coated alumina solid oxide materials which can be used can have a silica content from about 5% by weight to about 95% by weight. In one aspect, the silica content of these solid oxides can be from about 10% by weight to about 80% silica by weight, or from about 20% by weight to about 70% silica by weight. In another aspect, such materials can have silica contents ranging from about 15% to about 60% silica by weight, or from about 25% to about 50% silica by weight. The solid oxides contemplated herein can have any suitable surface area, pore volume, and particle size, as would be recognized by those of skill in the art.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, molybdate, and the like, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, and the like, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other aspects, the electron-withdrawing anion can comprise fluoride and/or sulfate.

The activator-support generally can contain from about 1 wt. % to about 25 wt. % of the electron-withdrawing anion, based on the weight of the activator-support. In particular aspects provided herein, the activator-support can contain from about 1 to about 20 wt. %, from about 2 wt. % to about 20 wt. %, from about 3 wt. % to about 20 wt. %, from about 2 wt. % to about 15 wt. %, from about 3 wt. % to about 15 wt. %, from about 3 wt. % to about 12 wt. %, or from about 4 wt. % to about 10 wt. %, of the electron-withdrawing anion, based on the total weight of the activator-support.

In an aspect, the activator-support can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, and the like, as well as any mixture or combination thereof. In another aspect, the activator-support employed in the catalyst systems described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, sulfated silica-coated alumina, and the like, as well as combinations thereof. In yet another aspect, the activator-support can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina. In some aspects, the activator-support can comprise a fluorided solid oxide, while in other aspects, the activator-support can comprise a sulfated solid oxide.

Various processes can be used to form activator-supports useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, and the like, or combinations thereof), and various calcining procedures and conditions are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485, which are incorporated herein by reference in their entirety. Other suitable processes and procedures for preparing activator-supports (e.g., fluorided solid oxides and sulfated solid oxides) are well known to those of skill in the art.

Olefin Monomers and Olefin Polymers

Olefin monomers contemplated herein typically include olefin compounds having from 2 to 30 carbon atoms per molecule and having at least one olefinic double bond. Homopolymerization processes using a single olefin, such as ethylene, propylene, butene, hexene, octene, and the like, are encompassed, as well as copolymerization, homopolymerization, terpolymerization, and similar polymerization reactions using an olefin monomer with at least one different olefinic compound. As previously disclosed, polymerization processes are meant to encompass oligomerization processes as well.

As an example, any resultant ethylene copolymers or terpolymers generally can contain a major amount of ethylene (>50 mole percent) and a minor amount of comonomer (<50 mole percent). Comonomers that can be copolymerized with ethylene often have from 3 to 20 carbon atoms in their molecular chain.

Acyclic, cyclic, polycyclic, terminal (a), internal, linear, branched, substituted, unsubstituted, functionalized, and non-functionalized olefins can be employed. For example, typical unsaturated compounds that can be polymerized to produce olefin polymers can include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes (e.g., 1-octene), the four normal nonenes, the five normal decenes, and the like, or mixtures of two or more of these compounds. Cyclic and bicyclic olefins, including but not limited to, cyclopentene, cyclohexene, norbornylene, norbornadiene, and the like, also can be polymerized as described herein. Styrene also can be employed as a monomer or as a comonomer. In an aspect, the olefin monomer can comprise a $C_2$-$C_{24}$ olefin; alternatively, a $C_2$-$C_{12}$ olefin; alternatively, a $C_6$-$C_{24}$ olefin; alternatively, a $C_2$-$C_{10}$ α-olefin; alternatively, propylene, 1-butene, 1-pentene, 1-hexene, 1-heptene, 1-octene, 1-decene, or styrene; alternatively, ethylene, propylene, 1-butene, 1-hexene, or 1-octene; alternatively, ethylene or propylene; alternatively, ethylene; or alternatively, propylene.

When a copolymer (or alternatively, a terpolymer) is desired, the olefin monomer can comprise, for example, ethylene or propylene, which is copolymerized with at least one comonomer. According to one aspect, the olefin monomer in the polymerization process can comprise ethylene. In this aspect, examples of suitable olefin comonomers can include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to another aspect, the olefin monomer can comprise ethylene and the olefin comonomer can comprise an α-olefin, while in yet another aspect, the comonomer can comprise propylene, 1-butene, 1-pentene, 1-hexene, 1-octene, 1-decene, styrene, or any combination thereof or alternatively, the olefin comonomer can comprise 1-butene, 1-hexene, 1-octene, or a combination thereof.

Generally, the amount of comonomer introduced into a polymerization reactor to produce the copolymer can be from about 0.01 weight percent (wt. %) to about 50 weight percent of the comonomer based on the total weight of the monomer and comonomer. According to another aspect, the amount of comonomer introduced into a polymerization reactor can be from about 0.01 weight percent to about 40 weight percent comonomer based on the total weight of the monomer and comonomer. In still another aspect, the amount of comonomer introduced into a polymerization reactor can be from about 0.1 weight percent to about 35 weight percent comonomer based on the total weight of the monomer and comonomer. Yet, in another aspect, the amount of comonomer introduced into a polymerization reactor can be from about 0.5 weight percent to about 20 weight percent comonomer based on the total weight of the monomer and comonomer.

According to one aspect, at least one monomer/reactant can be ethylene, so the polymerization reaction can be a homopolymerization involving only ethylene, or a copolymerization with a different acyclic, cyclic, terminal, internal, linear, branched, substituted, or unsubstituted olefin. In addition, the methods disclosed herein intend for olefin to also encompass diolefin compounds that include, but are not limited to, 1,3-butadiene, isoprene, 1,4-pentadiene, 1,5-hexadiene, and the like.

Olefin polymers encompassed herein can include any polymer (or oligomer) produced from any olefin monomer (and optional comonomer(s)) described herein. For example, the olefin polymer can comprise an ethylene homopolymer, a propylene homopolymer, an ethylene copolymer (e.g., ethylene/1-butene, ethylene/1-hexene, or ethylene/l-octene), a propylene random copolymer, a propylene block copolymer, and the like, including combinations thereof. Moreover, the olefin polymer (or oligomer) can comprise, in certain aspects, an olefin dimer, olefin trimer, or olefin tetramer, and including mixtures or combinations thereof. Thus, olefin polymer encompasses oligomerization products of $C_6$-$C_{24}$ olefins (or $C_6$-$C_{24}$ α-olefins, or 1-hexene, or 1-octene, or 1-decene, or 1-dodecene, or 1-tetradecene, or 1-hexadecene).

Catalyst Preparation

The disclosed methods for determining a first concentration of a first transition metal compound and a second concentration of a second transition metal compound in a solution containing the first transition metal compound and the second transition metal compound also can be utilized in a process for preparing a catalyst composition. One such process for preparing a catalyst composition can comprise (I) contacting a first transition metal compound, a second transition metal compound, a solid activator, and an optional co-catalyst (e.g., in a catalyst preparation vessel) to form the catalyst composition, (II) determining the first concentration of the first transition metal compound and the second concentration of the second transition metal compound in a solution containing the first transition metal compound and the second transition metal compound, the solution separated from (or obtained from) the catalyst composition, and (III) adjusting a relative amount of at least one component of the catalyst composition based on the first concentration and/or the second concentration in the solution (or based on the determined concentrations). Hence, an addition amount of at least one component of the catalyst composition (e.g., flow rate or feed rate into the catalyst preparation vessel) can be adjusted, manually and/or automatically, based on the determined concentration. Generally, the features of the processes for preparing a catalyst composition disclosed herein (e.g., the transition metal compounds, the solid activator, the co-catalyst (if present), the method of determining the first concentration and the second concentration, and the adjustment of the relative amount of at least one component, among others) are independently described herein, and can be combined in any combination to further describe the disclosed processes. Moreover, other steps can be conducted before, during, and/or after any of the steps listed in the disclosed processes, unless stated otherwise.

Referring first to step (I), in which the first transition metal compound, the second transition metal compound, the solid activator, and optionally, the co-catalyst can be contacted to form the catalyst composition. Thus, in one aspect, step (I) can comprise contacting the first transition metal compound, the second transition metal compound, and the solid activator, while in another aspect, step (I) can comprise contacting the first transition metal compound, the second transition metal compound, the solid activator, and the co-catalyst. The respective catalyst components can be contacted in any order or sequence. For instance, the solid activator and the co-catalyst can be contacted first (precontacted) prior to being contacted with the transition metal compounds. Likewise, a mixture of the first and second transition metal compounds (e.g., in a solvent) can be contacted with the solid activator and the co-catalyst, or the transition metal compounds can be contacted sequentially. The solid activator can be present as a slurry of the activator-support in a suitable diluent, and the co-catalyst can be in solution in a suitable solvent. The solvents or diluents for the transition metal compounds, solid activator, and co-catalyst can be any of the hydrocarbon solvents disclosed herein, either singly or in any combination. Thus, the solution containing the transition metal compounds can contain any of the aforementioned hydrocarbon solvents.

Referring now to FIG. 1, the first transition metal compound solution feed stream 102 and the second transition metal compound solution feed stream 104 can form a combined transition metal compound solution feed stream 105 to the catalyst preparation vessel 110. Alternatively, feed streams 102 and 104 can be independently fed directly to the catalyst preparation vessel 110. The separate feed streams for the activator and the co-catalyst to the catalyst preparation vessel are not shown.

Generally, the amounts of each component (and therefore, the relative amounts) used to form the catalyst composition are known. However, when a combined transition metal compound solution feed stream 105 is used, the relative amounts of the respective transition metal compounds may be unknown, or not known with sufficient precision. In such circumstances, as shown in FIG. 1, the sample stream 132 from the combined feed stream 105 can be submitted to the analytical system 140 for determination of the first concentration of the first transition metal compound and the second concentration of the second transition metal compound in the combined feed stream 105 prior to its entry into the catalyst preparation vessel 110.

As disclosed herein, the first transition metal compound and the second transition metal compound, independently, can comprise any suitable transition metal compound or any transition metal compound disclosed herein, whether a non-metallocene compound, a bridged metallocene compound, an unbridged metallocene compound, and so forth. Likewise, the co-catalyst (when present) can comprise any suitable co-catalyst or any co-catalyst disclosed herein. In particular aspects of this invention, the co-catalyst can comprise an organoaluminum compound, such as trimethylaluminum, triethylaluminum, triisobutylaluminum, and the like.

In aspects of this invention disclosed hereinabove relating to a process for operating a polymerization reactor system, the catalyst composition can be a liquid (or homogeneous) catalyst system. In regards to the process of preparing a catalyst composition, these processes are most applicable to heterogeneous or supported catalyst systems. Therefore, the activator can be any suitable solid activator, or any solid activator disclosed herein. In one aspect, the solid activator can comprise a solid aluminoxane, while in another aspect, the solid activator can comprise an activator supported on any suitable support, such as a solid oxide (e.g., supported MAO), and in yet another aspect, the solid activator can comprise an activator-support (e.g., a solid oxide treated with an electron-withdrawing anion). Combinations of more than one solid activator can be used, if desired.

Step (II) is directed to determining a first concentration of the first transition metal compound and a second concentration of the second transition metal compound in the solution comprising the first transition metal compound and the second transition metal compound. The solution containing the first transition metal compound and the second transition metal compound can be separated from (or obtained from) the catalyst composition. Step (II) can comprise the steps of (i) providing a first reference absorbance profile ($F_1$) of the first transition metal compound in a first reference solution at a first known concentration, and a second reference absorbance profile ($F_2$) of the second transition metal compound in a second reference solution at a second known concentration, (ii) submitting a sample of the solution to a sample chamber, (iii) irradiating the sample in the chamber with a light beam at a wavelength in the UV-visible spectrum, (iv) generating a sample absorbance profile of the sample, and calculating a curve having the formula $\beta_1 F_1 + \beta_2 F_2$ to fit the sample absorbance profile to a least-squares regression fit value ($R^2$) of at least 0.9, wherein $\beta_1$ is a first weighting coefficient, $F_1$ is the first reference absorbance profile of the first transition metal compound in the first reference solution at the first known concentration, $\beta_2$ is a second weighting coefficient, and $F_2$ is the second reference absorbance profile of the second transition metal compound in the second reference solution at the second known concentration, and (v) multiplying the first known concentration with $\beta_1$ to determine the first concentration of the first transition metal compound in the solution, and multiplying the second known concentration with $\beta_2$ to determine the second concentration of the second transition metal compound in the solution. Accordingly, the specific features relating to step (II) can be the same as those disclosed and described herein as it pertains to methods for determining the first concentration of the first transition metal compound and the second concentration of the second transition metal compound in the solution comprising the first transition metal compound and the second transition metal compound.

In step (II), the solution containing the first transition metal compound and the second transition metal compound can be separated from the catalyst composition using any suitable technique for separating liquids from solids. In one aspect, for instance, the catalyst composition can be sieved, filtered, and/or centrifuged, to separate the solution (or liquid portion) containing the first transition metal compound and the second transition metal compound from the solids portion of the catalyst composition. In another aspect, a settling tube, such as described in U.S. Pat. No. 9,708,426 (incorporated herein by reference in its entirety), can be used to separate the liquid and solid fractions of the catalyst composition. In yet another aspect, a modified flow cell can be used. For the modified flow cell, the standard flow cell used for UV-Vis analysis can be fitted with an extended lower portion, which can be of the same or different diameter, and can be constructed of the same or different material, as that of the standard flow cell. The extended lower portion can be configured to act like a settling tube, such that the higher density solid components settle to bottom of the modified flow cell, and the liquid (i.e., the solution containing the transition metal compounds) occupies the upper portion of the modified flow cell. The liquid (solution) portion in the modified flow cell then can be irradiated (in step (iii)) with a light beam at wavelengths in the UV-visible spectrum.

Referring now to step (III), a relative amount of at least one component of the catalyst composition can be adjusted based on the first concentration (of the first transition metal compound in the solution) and/or the second concentration (of the second transition metal compound in the solution). Thus, an addition amount of at least one component of the catalyst composition—the first transition metal compound, the second transition metal compound, the solid activator, and/or the co-catalyst, if present—can be adjusted based on the first concentration and/or the second concentration. Accordingly, based on the first concentration and/or the second concentration, the amount of the first transition metal compound in the catalyst composition can be increased or decreased (e.g., the addition amount or feed rate into the catalyst preparation vessel can be increased or decreased). Additionally or alternatively, the amount of the second transition metal compound in the catalyst composition can be increased or decreased (e.g., the addition amount or feed rate into the catalyst preparation vessel can be increased or decreased). Additionally or alternatively, the amount of the solid activator in the catalyst composition can be increased or decreased (e.g., the addition amount or feed rate into the catalyst preparation vessel can be increased or decreased). Additionally or alternatively, the amount of the co-catalyst in the catalyst composition can be increased or decreased (e.g., the addition amount or feed rate into the catalyst preparation vessel can be increased or decreased).

Consistent with aspects disclosed herein, in step (III), the relative amount of at least one component of the catalyst composition can be adjusted based on the first concentration of the first transition metal compound and/or the second concentration of the second transition metal compound in the solution. The adjustment to the relative amount of the particular catalyst component can be readily ascertained by one of skill in the art depending upon, for instance, the historic and the prevailing conditions in the catalyst preparation vessel and the overall composition (e.g., the desired composition) of the catalyst composition. An illustrative technique is provided in the Examples that follow.

In another aspect of this invention, a catalyst preparation system is provided, and in this aspect, the catalyst preparation system can comprise (a) a catalyst preparation vessel configured to contact a first transition metal compound, a second transition metal compound, and a solid activator (and a co-catalyst, if used) to form a catalyst composition, (b) an activator feed stream configured to introduce the solid activator into the catalyst preparation vessel, (c) a first transition metal compound feed stream configured to introduce the first transition metal compound into the catalyst preparation vessel, (d) a second transition metal compound feed stream configured to introduce the second transition metal compound into the catalyst preparation vessel, (e) a catalyst system feed stream configured to withdraw the catalyst composition from the catalyst preparation vessel (e.g., and to introduce the catalyst composition to a reactor), and (f) an analytical system configured to determine a first concentration of the first transition metal compound and a second concentration of the second transition metal compound in a solution comprising the first transition metal compound and the second transition metal compound, the solution separated from (or obtained from) the catalyst composition (e.g., the catalyst system feed stream).

Generally, the features of any of the catalyst preparation systems disclosed herein (e.g., the catalyst preparation vessel, the activator feed stream, the first transition metal compound feed stream, the second transition metal compound feed stream, the catalyst system feed stream, the analytical system, among others) are independently described herein, and these features can be combined in any combination to further describe the disclosed catalyst preparation systems. Moreover, other devices or catalyst preparation system components can be present in the disclosed catalyst preparation systems, unless stated otherwise. For instance, the catalyst preparation system can further include a co-catalyst feed stream configured to introduce any suitable co-catalyst into the catalyst preparation vessel.

The analytical system can include any analytical system or device that is capable of determining the first concentration of the first transition metal compound and the second concentration of the second transition metal compound in a solution that contains the first transition metal compound and the second transition metal compound. For instance, the analytical system can include an ultraviolet-visible (UV-Vis) spectrometer (e.g., alone or in combination with another analytical device/method, such as a fluorescence spectroscopy method; a UV-Vis-NIR system; and so forth).

In one aspect of this invention, the analytical system can include an ultraviolet-visible spectrometer with an integrated computer system, as described herein; the UV-Vis spectrometer has a "built-in" computer system. In another aspect of this invention, the analytical system can include an ultraviolet-visible spectrometer and an external computer system, as described herein; the UV-Vis can perform the absorbance measurement and generate the absorbance data and profile, but an external computer system can take the output from the UV-Vis and determine the respective concentrations of the first and second transition metal compounds.

Generally, the analytical system can further comprise a liquid-solid separating device configured to separate the solution (comprising the first transition metal compound and the second transition metal compound) from a solid portion of the catalyst composition or catalyst system feed stream, before analysis by the analytical instrument, such as a UV-Vis spectrometer. While not being limited thereto, the liquid-solid separating device can comprise a sieving device (e.g., a strainer), a filter assembly, a centrifugation device, a settling tube, and the like, or a combination thereof, to separate or segregate the solution (or liquid portion) containing the first transition metal compound and the second transition metal compound from the solids portion of the catalyst composition. Additionally or alternatively, the liquid-solid separating device can comprise a modified flow cell, as described herein; a standard flow cell used for UV-Vis analysis can be fitted with an extended lower portion configured to act like a settling tube, such that the higher density solid components settle to bottom of the modified flow cell, and the liquid (i.e., the solution containing the transition metal compounds) occupies the upper portion of the modified flow cell.

For the catalyst preparation system, any of the features or options for the catalyst preparation vessel, absorbance profiles (e.g., reference absorbance profiles and sample absorbance profile), and the curve having the formula $\beta_1 F_1 + \beta_2 F_2$, among others, can be the same as those disclosed herein for the polymerization reactor system, or for the processes of operating the polymerization reactor system.

In one aspect of the catalyst preparation system, the first transition metal compound feed stream and the second transition metal compound feed stream can feed directly into the catalyst preparation vessel, while in another aspect, the first transition metal compound and the second transition metal compound can be combined together and fed to the catalyst preparation vessel. Optionally, the activator and the co-catalyst feed streams can be combined together (pre-contacted), and then the pre-contacted mixture can be fed into the catalyst preparation vessel.

The catalyst preparation system can further comprise (g) a controller that is configured to control a flow rate of the activator feed stream, a flow rate of the first transition metal compound feed stream, and/or a flow rate of the second transition metal compound feed stream into the catalyst preparation vessel based on, or according to, the first concentration and/or the second concentration determined by the analytical system. If a co-catalyst is fed to the catalyst preparation vessel, the controller can be further configured to control a flow rate of the co-catalyst feed stream.

For the catalyst preparation system, any of the features or options for the controller can be the same as those disclosed herein for the polymerization reactor system, or for the processes of operating the polymerization reactor system. As an example, if "free" transition metal compounds are determined to be in the solution analyzed by the analytical system, the flow rate of the activator feed stream to the catalyst preparation vessel can be increased such that, after the increase in addition rate of the solid activator, all of the transition metal compounds can be absorbed by or impregnated on the solid activator.

In the disclosed catalyst preparation systems, the controller can adjust a relative amount of at least one component of the catalyst composition based on the first concentration (of the first transition metal compound in the solution) and/or the second concentration (of the second transition metal compound in the solution). Accordingly, based on the respective concentrations of the first and second transition metal compounds in the solution, the flow rate of the activator feed stream into the catalyst preparation vessel can be increased or decreased; additionally or alternatively, the flow rate of the first transition metal compound feed stream can be increased or decreased; additionally or alternatively, the flow rate of the second transition metal compound feed stream can be increased or decreased; and additionally or alternatively, the flow rate of the co-catalyst feed stream can be increased or decreased.

Figure 20:
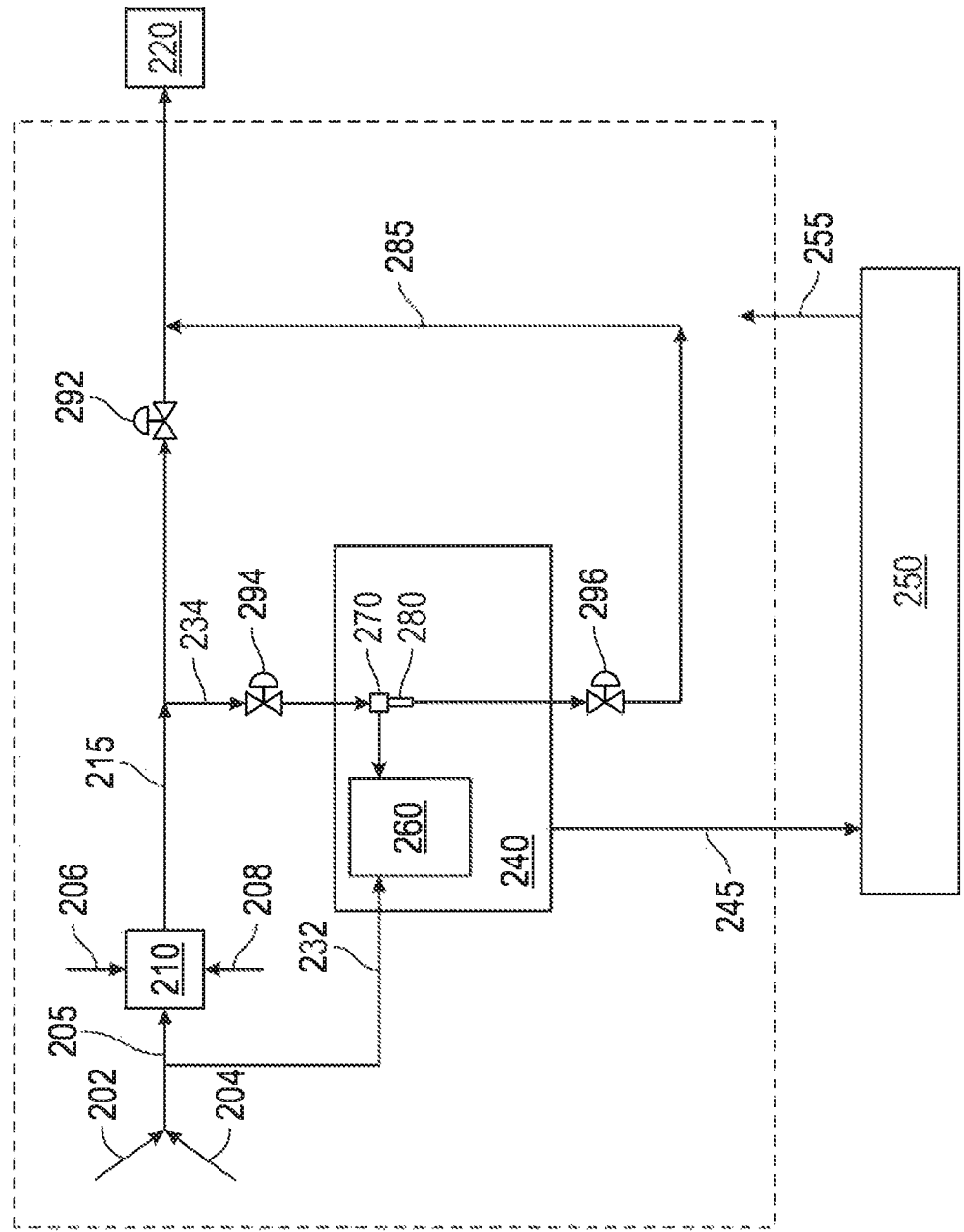
FIG. 20 illustrates a schematic block diagram of a catalyst preparation system consistent with aspects of this invention.

A representative catalyst preparation system 200 consistent with aspects of this invention is illustrated in FIG. 20. The catalyst preparation system 200 includes a catalyst preparation vessel 210, an analytical system 240, and a controller 250. A reactor 220 also is shown in FIG. 20. The catalyst preparation system 200 includes a first transition metal compound solution feed stream 202 and a second transition metal compound solution feed stream 204 (which form a combined transition metal compound solution feed stream 205 to the catalyst preparation vessel 210), and an activator feed stream 206 and a co-catalyst feed stream 208 to the catalyst preparation vessel 210. While not shown, feed streams 202 and 204 can be independently fed directly to the catalyst preparation vessel 210. As shown in FIG. 20, a sample stream 232 from the combined feed stream 205 can be submitted to the analytical system 240 and a UV-Vis spectrometer 260 for determination of the respective concentrations of the first and second transition metal compounds in the combined feed stream 205 prior to its entry into the catalyst preparation vessel 210.

A catalyst system feed stream 215 can flow through valve 292 from the catalyst preparation vessel 210 and enter the reactor 220. The catalyst system feed stream 215 can be a supported (or heterogeneous) catalyst system containing the first transition metal compound and the second transition metal compound. A sample stream 234 from the catalyst system feed stream 215 can flow through valve 294 and enter the analytical system 240 for determination of the respective concentrations of the first and second transition metal compounds in the solution portion of stream 234. The sample stream can enter flow cell 270 with settling tube 280 (the tube is shown with a smaller diameter than the flow cell, but its diameter can be the same or larger than that of the flow cell). The flow cell 270 and settling tube 280 (e.g., a modified flow cell) can be configured to separate or segregate the solid components of the sample stream 234 of the catalyst system from the liquid components, so that the UV-Vis spectrometer 260 can analyze the liquid portion in the flow cell 270. After analysis, the analyzed catalyst sample stream 285 can flow through valve 296, and be recycled with catalyst system feed stream 215.

Information or data 245 on the respective concentrations of the first and second transition metal compounds from the analytical system 240 can be provided to controller 250, which can then control or adjust 255 a flow rate of the activator feed stream 206, and/or a flow rate of the co-catalyst feed stream 208, and/or a flow rate of the combined feed stream 205 to catalyst preparation vessel 210. Additionally or alternatively, a flow rate of the first transition metal compound solution feed stream 202 and/or the second transition metal compound solution feed stream 204 can be controlled or adjusted 255. Thus, the controller 250 controls or adjusts 255 a flow rate of the activator feed stream 206, a flow rate of the co-catalyst feed stream 208, a flow rate of the first transition metal compound feed stream 202, and/or a flow rate of the second transition metal compound feed stream 204 into the catalyst preparation vessel 210 based on, or according to, the concentrations determined by the analytical system 240.

The following is an illustrative and non-limiting example of the operation of the catalyst preparation system in FIG. 20. A first metallocene compound, a second metallocene compound, an activator-support, and an organoaluminum co-catalyst can be fed continuously to the catalyst preparation vessel. The first and second metallocene compound feed streams are combined prior to entry into the catalyst preparation vessel, and the respective first and second metallocene concentrations can be known or can be measured continuously, or as-needed, using an analytical system containing a UV-Vis spectrometer, via the techniques disclosed herein.

The active catalyst composition formed in the catalyst preparation vessel can be fed continuously to a polymerization reactor. The path the catalyst composition takes from the catalyst preparation vessel to the reactor can be switched between two possible pathways. In Path 1, the catalyst composition flows through valve 292 directly to the reactor, without interruption or measurement, and this is the path that is followed the majority of the time. When it is desirable to analyze the catalyst composition, however, Path 2 is taken: the catalyst composition flows to an analytical system before eventually making its way to the reactor.

For Path 2, valve 292 is closed, and valve 294 and valve 296 are opened for a desired period of time, which may be as little as 1-5 seconds or as much as 1-5 minutes, although not limited thereto. This causes the catalyst composition to follow sample stream 234, and allows the flow cell 270 and settling tube 280 to be purged with a fresh sample of the catalyst composition from the catalyst preparation vessel 210. Once the desired time period is over, valve 294 and valve 296 are closed, valve 292 is opened, and the catalyst composition again flows through valve 292 to the reactor.

While valve 294 and valve 296 are closed, the catalyst composition slurry present between these two valves has an opportunity to settle, and the supernatant solution containing "free" first metallocene and second metallocene compounds can be analyzed by the UV-Vis spectrometer 260 through flow cell 270. By measuring the respective amounts of "free" metallocenes, the amount of the respective metallocene compounds absorbed/impregnated on the activator-support can be determined (via comparison with the combined first and second metallocene compound feed streams entering the catalyst preparation vessel).

Also beneficially, these measurements can be performed in real time, and with minimal intervention and minimal waste. The controller 250 can be further configured to control the valve opening/closing functions, and their periodicity and duration. Additionally, the catalyst preparation system can include more than one analytical device; for instance, one UV-Vis instrument can be used to measure incoming transition metal concentrations into the catalyst preparation vessel, and a second UV-Vis instrument can be used to measure "free" transition metal concentrations in the solution portion of the supported catalyst composition.

Expanding to Three or More Transition Metal Compounds

Disclosed herein are methods for determining the respective concentrations of two different transition metal compounds in a solution comprising the two different transition metal compounds, as well as related polymerization reactor systems and processes for operating polymerization reactor systems, and related catalyst preparations systems and processes for preparing catalyst compositions. However, the methods, processes, and systems are not limited to solutions containing only two transition metal compounds. The methods, processes, and systems disclosed herein also are applicable to solutions containing three or more different transition metal compounds, e.g., three different transition metal compounds, four different transition metal compounds, and so forth. As one of skill in the art would readily recognize, when three or more transition metal compounds are present in the solution—for example, from three to five different compounds—the accuracy of determining the respective concentration of each transition metal compound in the solution can depend greatly on the degree of overlap of the respective absorbance profiles (for each transition metal compound) at key absorbance wavelengths. For instance, in a solution containing compound 1 having a peak absorbance at 350 nm, compound 2 having a peak absorbance at 425 nm, compound 3 having a peak absorbance at 500 nm, and compound 4 having a peak absorbance at 575 nm, it may be easy to determine the respective concentrations of each compound with high accuracy.

Encompassed herein is a method for determining a first concentration of a first transition metal compound, a second concentration of a second transition metal compound, and a third concentration of a third transition metal compound, in a solution comprising the first transition metal compound, the second transition metal compound, and the third transition metal compound. This method can comprise (or consist essentially of, or consist of) (i) providing a first reference absorbance profile ($F_1$) of the first transition metal compound in a first reference solution at a first known concentration, a second reference absorbance profile ($F_2$) of the second transition metal compound in a second reference solution at a second known concentration, and a third reference absorbance profile ($F_3$) of the third transition metal compound in a third reference solution at a third known concentration, (ii) submitting a sample of the solution to a sample chamber, (iii) irradiating the sample in the chamber with a light beam at a wavelength (e.g., a range of wavelengths) in the UV-visible spectrum, (iv) generating (e.g., collecting or outputting) a sample absorbance profile of the sample, and calculating a curve having the formula $\beta_1 F_1 + \beta_2 F_2 + \beta_3 F_3$ to fit the sample absorbance profile to a least-squares regression fit value ($R^2$) of at least 0.9 (and often at least 0.99, or more), wherein $\beta_1$ is a first weighting coefficient, $F_1$ is the first reference absorbance profile of the first transition metal compound in the first reference solution at the first known concentration, $\beta_2$ is a second weighting coefficient, $F_2$ is the second reference absorbance profile of the second transition metal compound in the second reference solution at the second known concentration, $\beta_3$ is a third weighting coefficient, and $F_3$ is the third reference absorbance profile of the third transition metal compound in the third reference solution at the third known concentration, and (v) multiplying the first known concentration with $\beta_1$ to determine the first concentration of the first transition metal compound in the solution, multiplying the second known concentration with $\beta_2$ to determine the second concentration of the second transition metal compound in the solution, and multiplying the third known concentration with $\beta_3$ to determine the third concentration of the third transition metal compound in the solution.

In like manner, the method can be expanded to determine the respective concentrations of four different transition metal compounds, or five different transition metal compounds, etc., in a solution containing the four transition metal compounds, five transition metal compounds, etc.

Any of the features and aspects disclosed herein for analytical methods, polymerization reactor systems, processes for operating polymerization reactor systems, catalyst preparation systems, and processes for preparing catalyst compositions, that pertain to solutions containing two transition metal compounds are equally applicable to solutions containing three or more transition metal compounds, and these features and aspects can be used without limitation and in any combination to describe analytical methods, polymerization reactor systems, processes for operating polymerization reactor systems, catalyst preparation systems, and processes for preparing catalyst compositions, relating to solutions containing three or more transition metal compounds.

Flow Cell Apparatus and Related Methods

As it may pertain to the methods for determining the respective concentrations of transition metal compounds in a solution separated (or prepared) from a sample mixture from a reactor or from a heterogeneous or supported catalyst system, a method of measuring a property of a liquid in a vessel containing a liquid-solid mixture is disclosed. The method of measuring a property (e.g., a transition metal concentration) of a liquid (a solution) in a vessel (e.g., a reactor or a catalyst preparation vessel) containing a liquid-solid mixture can comprise (i) withdrawing a sample of the liquid-solid mixture from the vessel, (ii) flowing the sample of the liquid-solid mixture through a flow cell apparatus, (iii) periodically stopping the flow of the sample of the liquid-solid mixture in the flow cell apparatus for a time period sufficient for the solid to settle to a bottom portion (a first portion) of the flow cell apparatus and for the liquid to occupy an upper portion (a second portion) of the flow cell apparatus, (iv) irradiating the liquid in the upper portion of the flow cell apparatus with a light beam at a wavelength in the UV-visible spectrum to measure the property of the liquid, and (v) restoring flow through the flow cell apparatus. Optionally, the sample can be returned to the vessel. Thus, in the process for preparing a catalyst composition, the solution can be separated from the catalyst composition and the respective concentrations can be determined via a method comprising the steps of: submitting a flow of the catalyst composition to a sample chamber comprising a flow cell apparatus, periodically stopping the flow of the catalyst composition in the flow cell apparatus for a time period sufficient for a solid fraction to settle to a bottom portion (a first portion) of the flow cell apparatus and for a sample of the solution (liquid) to occupy an upper portion (a second portion) of the flow cell apparatus, and irradiating the sample in the upper portion of the flow cell apparatus with a light beam at a wavelength in the UV-visible spectrum. Subsequently, the flow can restored through the flow cell apparatus, and optionally, the flow of the catalyst composition can be returned to a catalyst preparation vessel, or introduced into a reactor.

Referring now to liquid-solid mixtures, a flow cell apparatus consistent with aspects of this invention can be configured to segregate the solid to a bottom portion of the flow cell apparatus and for the liquid to occupy an upper portion of the flow cell apparatus, and the upper portion of the flow cell apparatus can be configured for the liquid to be irradiated with a light beam at a wavelength in the UV-visible spectrum (e.g., the upper portion the flow cell apparatus can be configured for the liquid to be analyzed by a UV-Vis spectrometer). Thus, in a catalyst preparation system, the analytical system can comprise a flow cell apparatus configured to segregate (or separate) a solid fraction of the catalyst composition to a bottom portion of the flow cell apparatus and for a solution (liquid fraction) to occupy an upper portion of the flow cell apparatus, and the upper portion of the flow cell apparatus can be configured for the solution to be irradiated with a light beam at a wavelength in the UV-visible spectrum (e.g., the upper portion the flow cell apparatus can be configured for the solution to be analyzed by a UV-Vis spectrometer). Aspects of settling in liquid-solid systems that can be applied to the methods and systems provided herein are disclosed in U.S. Pat. No. 9,708,426, which is incorporated herein by reference in its entirety.

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

The chemical structures for the first, second, and third transition metal compounds used in the examples are provided below as MET-1, MET-2, and MET-3, respectively.

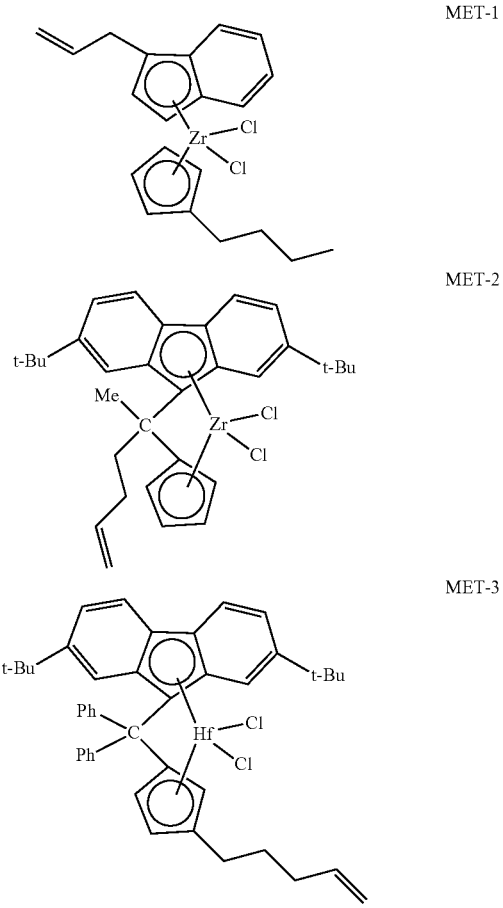

Solutions Containing One Transition Metal Compound

Separate stock solutions of MET-1 and MET-2 were prepared and used to further prepare the transition metal compound solutions of varying concentrations used in the examples. To prepare the stock solutions, the respective transition metal compound was weighed into a metal weigh pan using an analytical balance contained in a glovebox. The glovebox atmosphere was maintained at less than 0.1 ppm oxygen and less than 0.1 ppm water. The solvent (either 1-hexene or toluene) previously dried over molecular sieves was measured to a known volume using a volumetric flask. The entirety of the measured solvent was used to rinse the respective transition metal compound from the metal weigh pan into a glass vial (approximately 20-30 mL in volume) quantitatively. A small stir bar was added to the vial, and the vial was capped with a septum and metal seal. The contents of the vial were magnetically stirred at about 1000 rpm in the glovebox and monitored for dissolution. Dissolution was complete in approximately 30 min, depending on the transition metal compound, the solvent, and the concentration. In this manner, four stock solutions were prepared (MET-1 in 1-hexene, MET-1 in toluene, MET-2 in 1-hexene, and MET-2 in toluene). The transition metal compound concentration in each stock solution was 0.1 wt. %.

Then, for each stock solution, an aliquot of the stock solution was removed by syringe and added to a separate vial. An equal volume of the same solvent was added to the aliquot and the vial was loaded with a stir bar and capped as before for the stock solution. The mixture was allowed to stir, resulting in a solution possessing half the original concentration of the stock solution. This procedure was successively repeated to produce a series of solutions with transition metal concentrations decreasing by half each repetition.

The homogeneity of each sample was verified by visual inspection in the glovebox. Quartz cuvettes previously dried in an oven at 110° C. for several hours were loaded with their respective lids into the glovebox. One cuvette was loaded with approximately 3-3.5 mL pure solvent (either 1-hexene or toluene, and the same solvent used in the respective stock solutions and dilutions) and capped as a reference cell. The remaining cuvettes were each loaded with approximately 3-3.5 mL of a metallocene solution and securely capped to prevent accidental exposure to the atmosphere. The cuvettes were removed from the glovebox and analyzed using a Shimadzu UV-2550 UV-Vis spectrometer. The samples were typically analyzed in the wavelength range of 300-800 nm in 0.5 nm increments.

Figure 2:
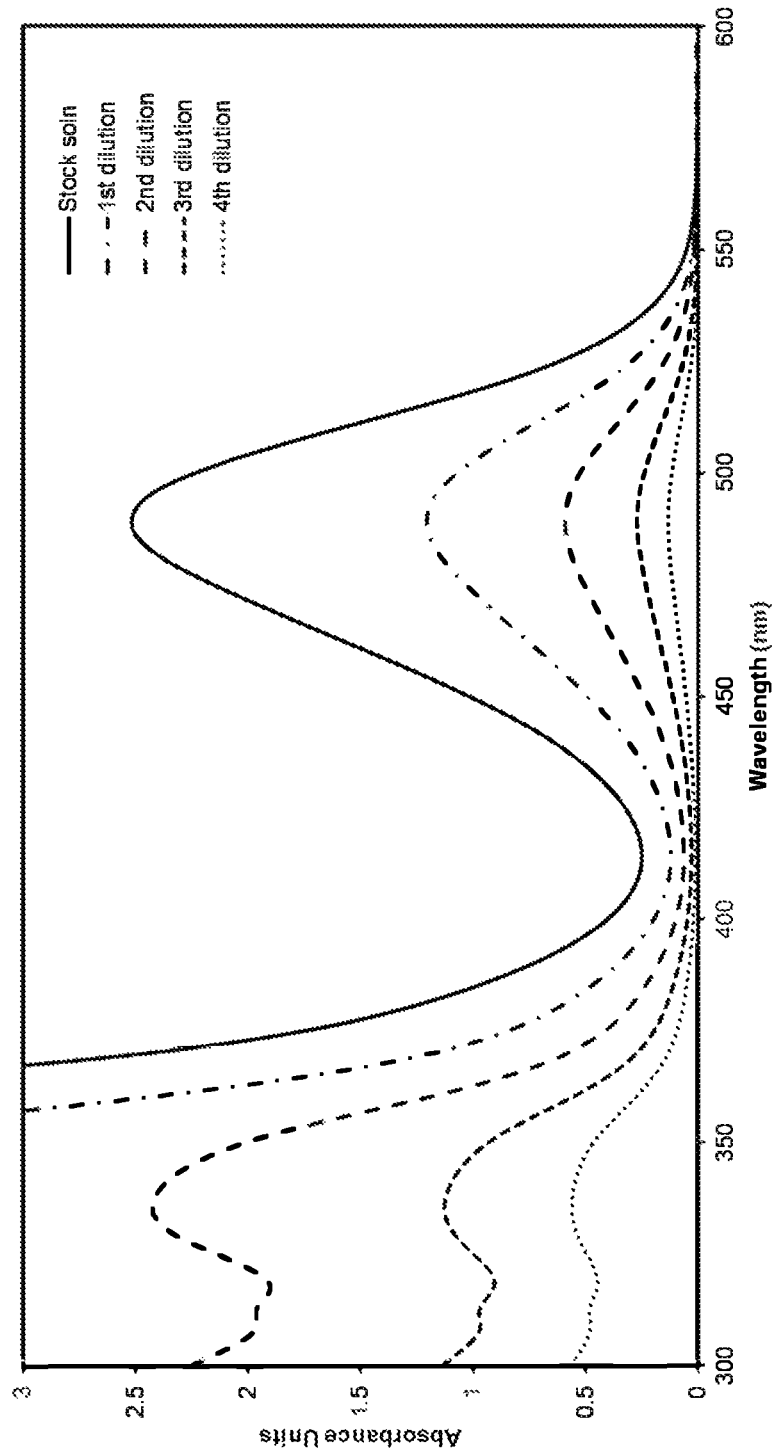
FIG. 2 presents plots of the UV-Vis absorbance profiles as a function of wavelength for various concentrations of transition metal compound MET-2 in toluene.
Figure 3:
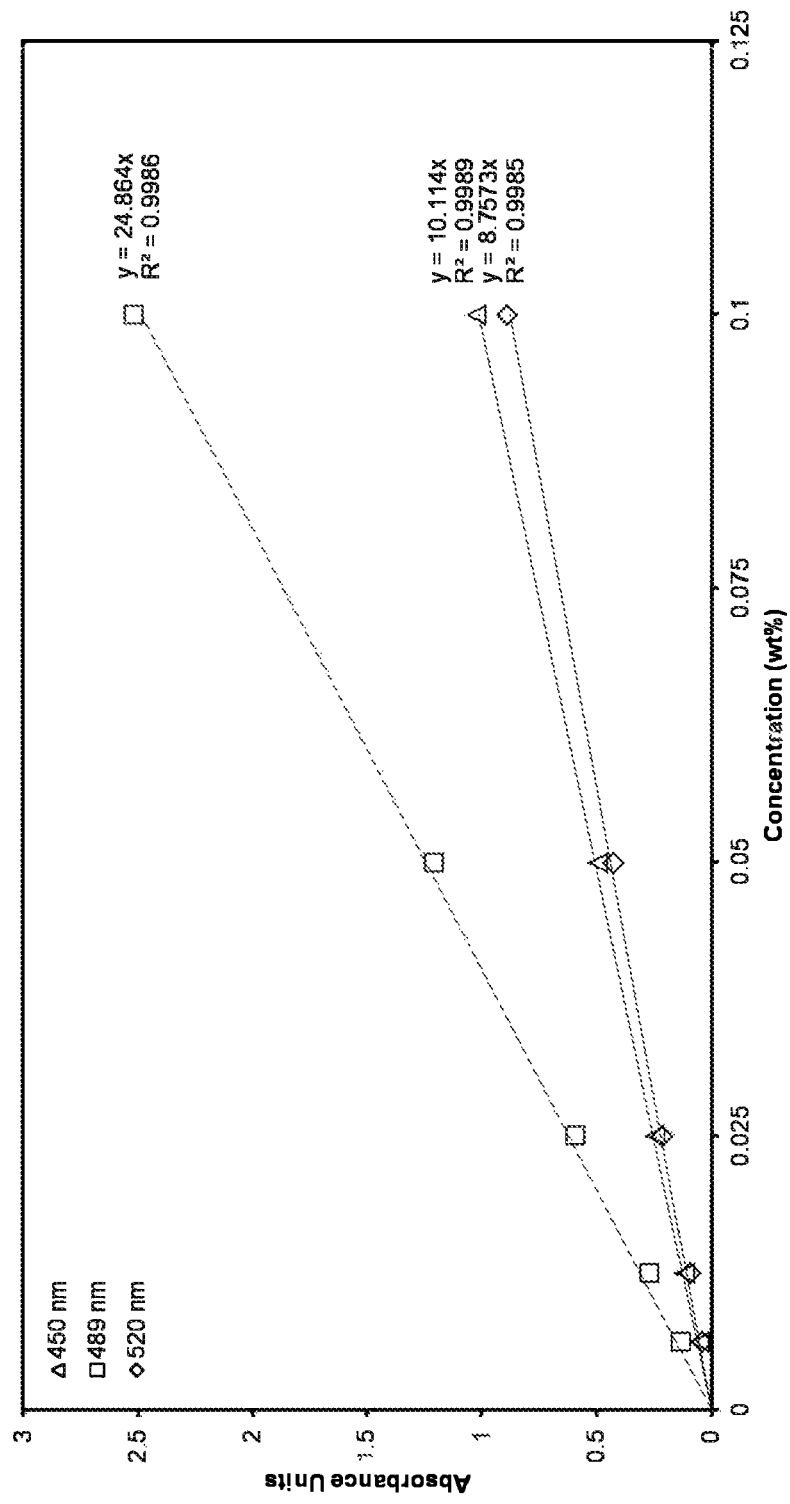
FIG. 3 presents linear calibration curves correlating absorbance to the concentration of transition metal compound MET-2 in toluene at various wavelengths.
Figure 4:
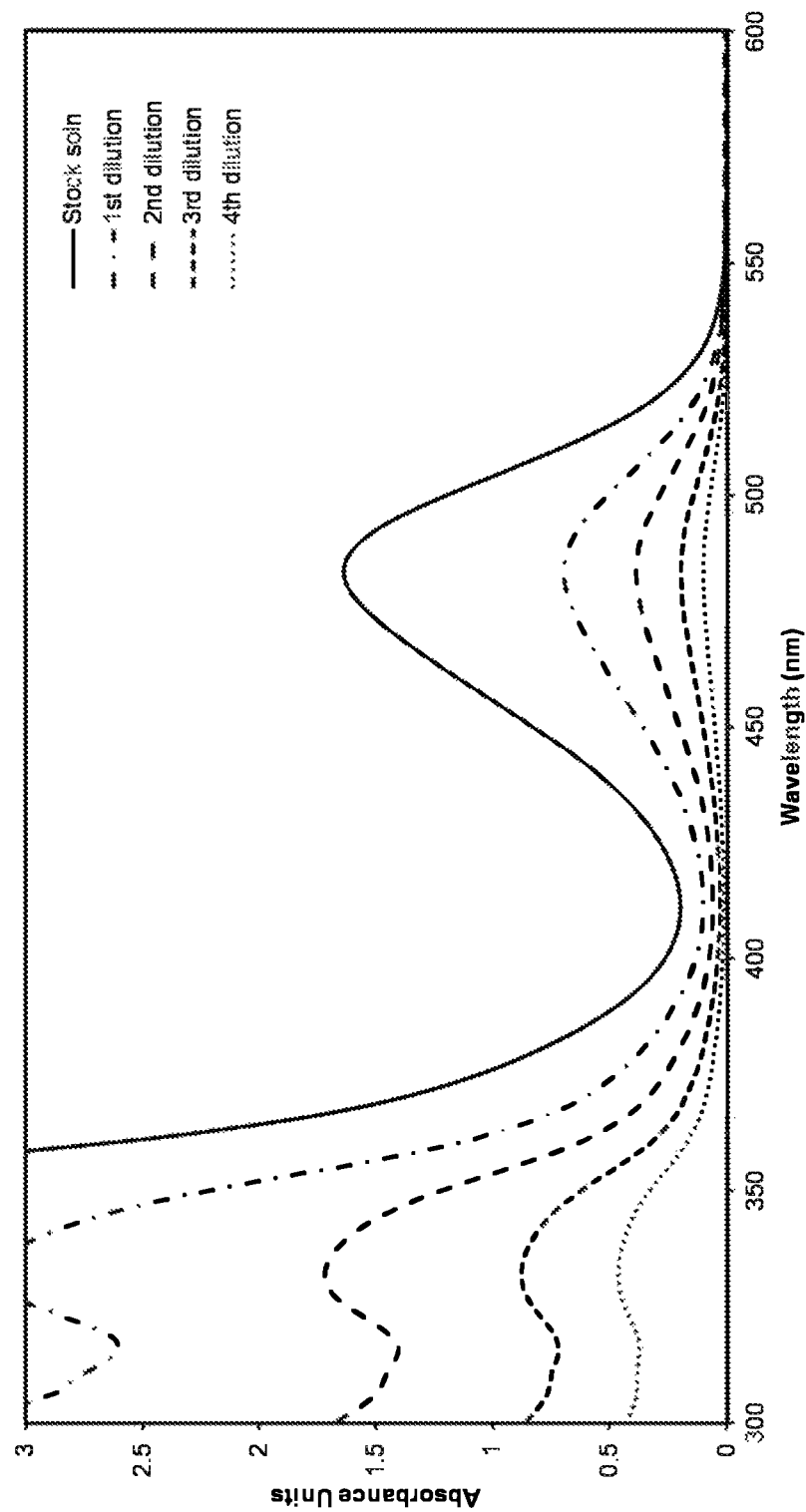
FIG. 4 presents plots of the UV-Vis absorbance profiles as a function of wavelength for various concentrations of transition metal compound MET-2 in 1-hexene.
Figure 5:
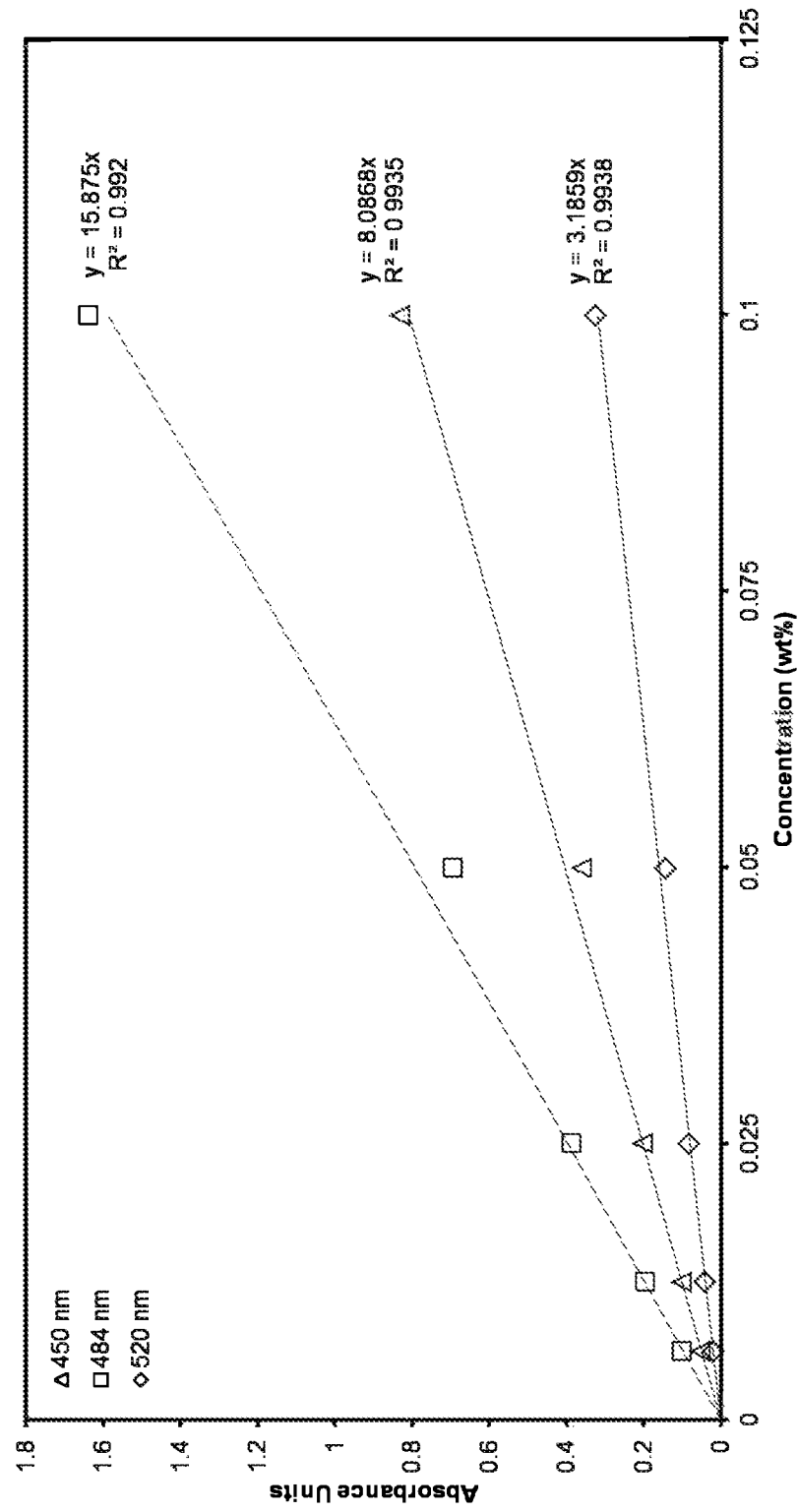
FIG. 5 presents linear calibration curves correlating absorbance to the concentration of transition metal compound MET-2 in 1-hexene at various wavelengths.
Figure 6:
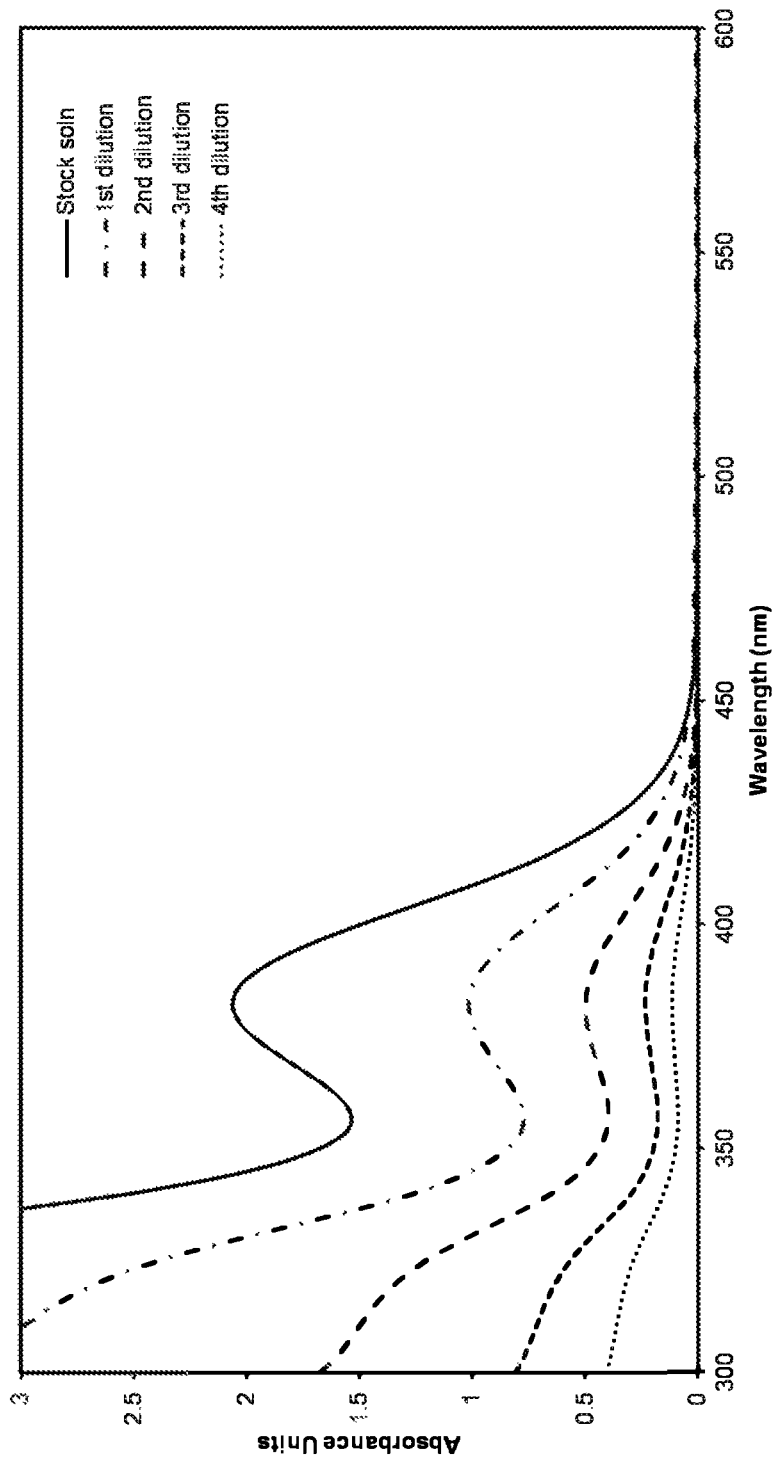
FIG. 6 presents plots of the UV-Vis absorbance profiles as a function of wavelength for various concentrations of transition metal compound MET-1 in toluene.
Figure 7:
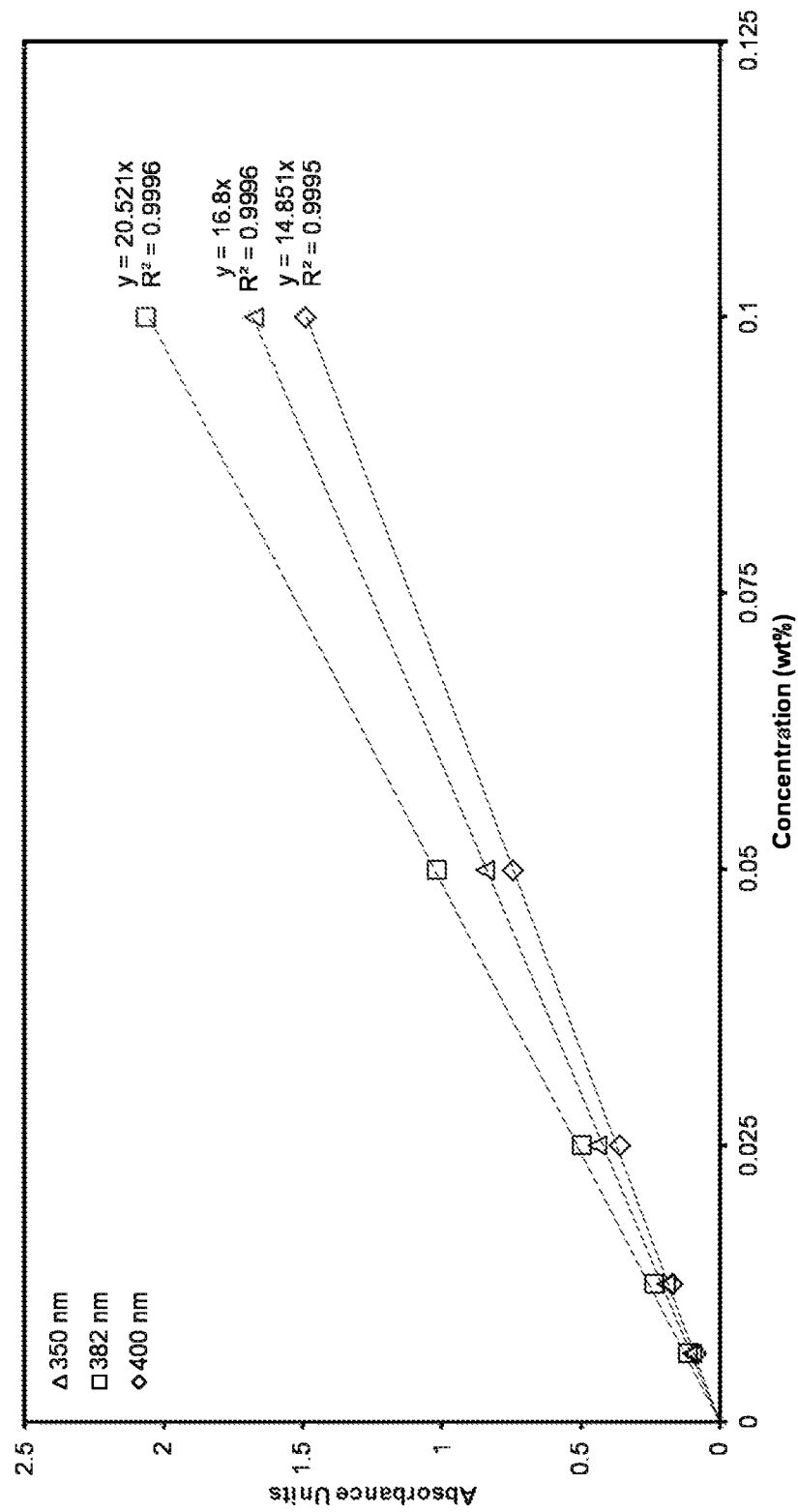
FIG. 7 presents linear calibration curves correlating absorbance to the concentration of transition metal compound MET-1 in toluene at various wavelengths.
Figure 8:
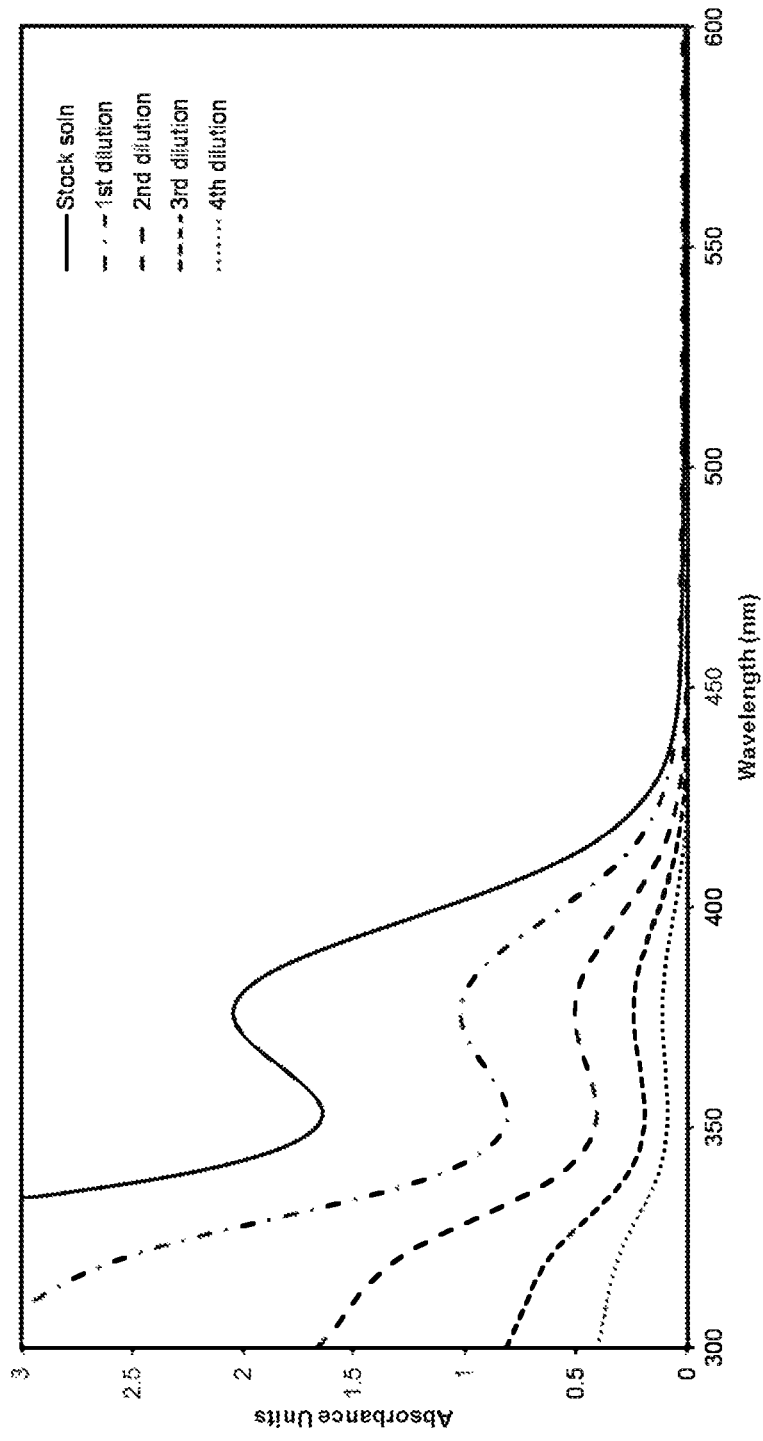
FIG. 8 presents plots of the UV-Vis absorbance profiles as a function of wavelength for various concentrations of transition metal compound MET-1 in 1-hexene.
Figure 9:
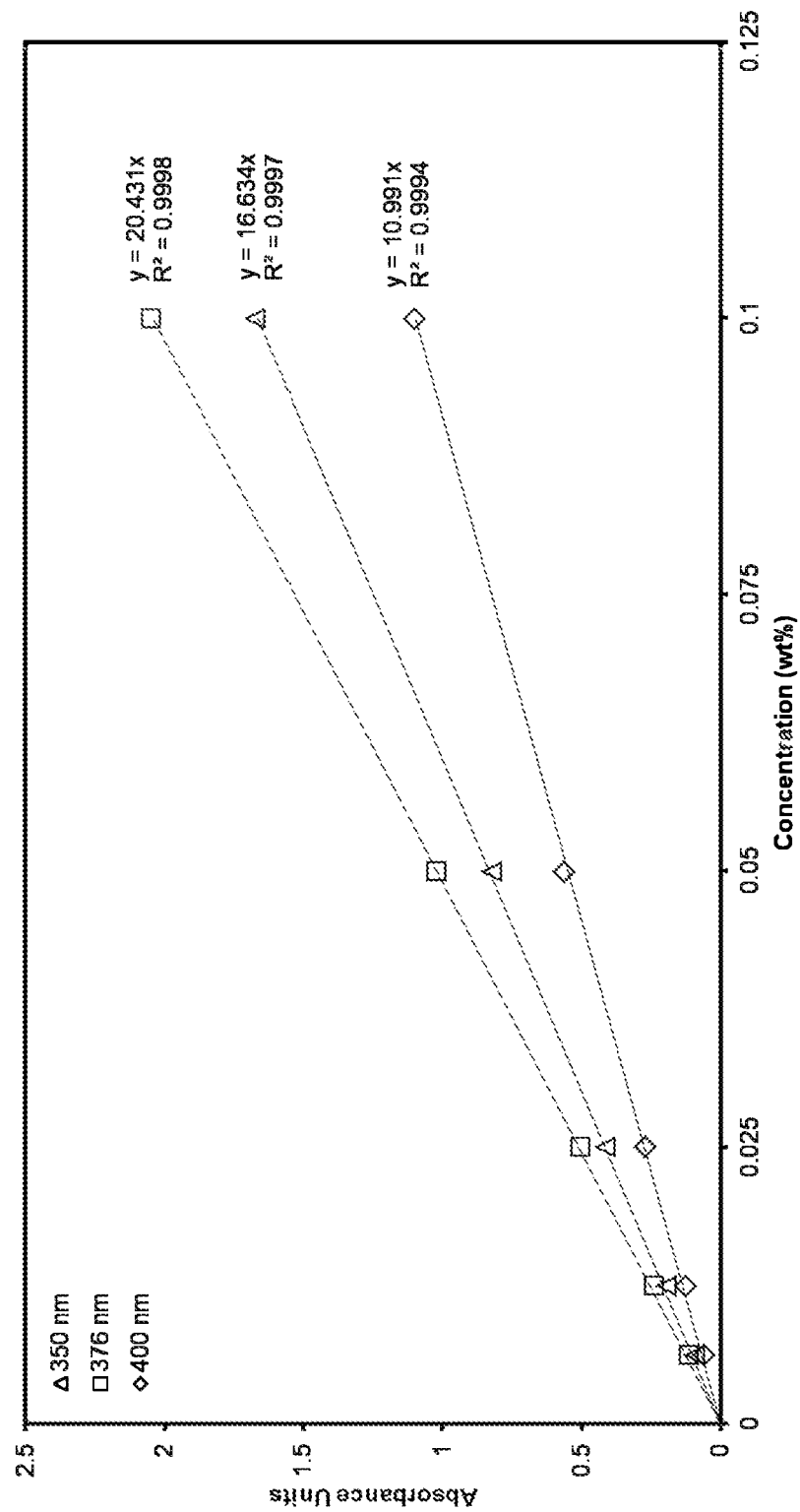
FIG. 9 presents linear calibration curves correlating absorbance to the concentration of transition metal compound MET-1 in 1-hexene at various wavelengths.

The raw data from each analysis consisted of a file containing columnar data of wavelength (nm) and absorbance (A.U.). Data from all the analyzed samples were copied from the raw data files into a single spreadsheet. Absorbance versus wavelength profiles for the wavelength range of 300-600 nm for each combination of (1) transition metal compound and (2) solvent were plotted in a single chart. Representative charts are shown in FIG. 2 (MET-2 in toluene), FIG. 4 (MET-2 in 1-hexene), FIG. 6 (MET-1 in toluene), and FIG. 8 (MET-1 in 1-hexene). Each transition metal compound in each solvent exhibited a characteristic peak whose absorbance maximum varied depending on concentration. Representative wavelengths were selected within this absorbance peak (e.g., one at the maximum and two additional, one on either side of the maximum). For each of the representative wavelengths, absorbance was plotted versus concentration of the transition metal concentration. Least-squares regression of the absorbance versus concentration data resulted in a calibration curve for the given combination of transition metal compound and solvent at that representative wavelength. Illustrative calibration curves are shown in FIG. 3 (MET-2 in toluene), FIG. 5 (MET-2 in 1-hexene), FIG. 7 (MET-1 in toluene), and FIG. 9 (MET-1 in 1-hexene).

As can be seen from FIGS. 2-9, each UV-Vis absorbance profile depends upon the transition metal compound, the solvent, and the concentration of the transition metal compound in the solvent. Additionally, the linear calibration curves were extremely accurate in correlating the measured absorbance to the concentration of the respective transition metal compound in the solvent at the selected wavelengths: statistical $R^2$ values were greater than 0.99 in all cases.

Solutions Containing Two Transition Metal Compounds

In Example 1, a stock solution of MET-1 in 1-hexene:toluene (9:1, weight basis) was prepared at a concentration of 0.313 wt. %. Absorbance spectra for MET-1 (1 mm path length) at a concentration of 0.313 wt. % was obtained in the same manner as described above, using only solvent (1-hexene/toluene) in the reference cell. This reference absorbance profile for MET-1 is plotted in FIG. 10. Similarly, a stock solution of MET-2 in 1-hexene:toluene (9:1, weight basis) was prepared at a concentration of 0.35 wt. %. Absorbance spectra for MET-2 (1 mm path length) at a concentration of 0.35 wt. % was obtained in the same manner as described above, using only solvent (1-hexene/toluene) in the reference cell. This reference absorbance profile for MET-2 also is plotted in FIG. 10.

From the respective stock solutions, a control solution containing both MET-1 and MET-2 at known concentrations was prepared: MET-1 (at 0.026 wt. %) and MET-2 (at 0.35 wt. %). Absorbance spectra for this solution of MET-1 and MET-2 in 1-hexene:toluene (9:1, weight basis) at a 1 mm path length was obtained in the same manner as described above, using only 1-hexene/toluene in the reference cell. This control absorbance profile for the solution containing both MET-1 and MET-2 is plotted in FIG. 10.

Figure 10:
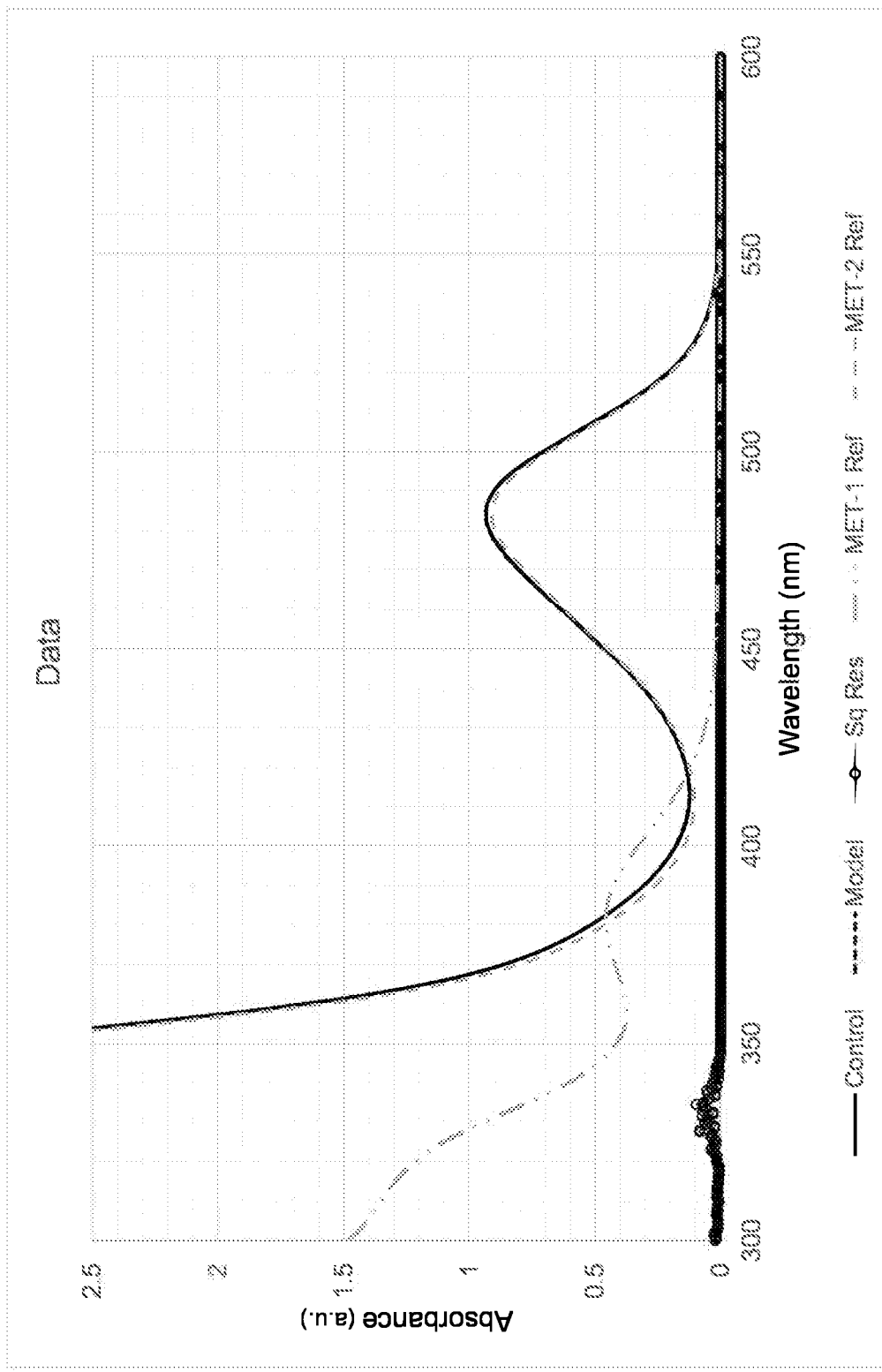
FIG. 10 presents plots of the UV-Vis absorbance profiles as a function of wavelength for MET-1, MET-2, and a mixture of MET-1 and MET-2, in 1-hexene/toluene, and a fitted model curve, for Example 1.

Using a multiple regression feature in Microsoft Excel, a curve having the formula "$\beta_1 F_1 + \beta_2 F_2$" was fit to the control absorbance profile over the 300-600 nm range. In this formula, $\beta_1$ is the weighting coefficient for MET-1, $F_1$ is the reference absorbance profile for MET-1 (at 0.313 wt. %), $\beta_2$ is the weighting coefficient for MET-2, and $F_2$ is the reference absorbance profile for MET-2 (at 0.35 wt. %). The model curve for the formula $\beta_1 F_1 + \beta_2 F_2$ is plotted in FIG. 10, where the $R^2$ value is 0.99997. In FIG. 10, the control absorbance profile curve and the model/fitted curve completely overlap, and cannot be distinguished visually. For the model curve having formula "$\beta_1 F_1 + \beta_2 F_2$" in FIG. 10, $\beta_1$ is equal 0.092 for MET-1 and $\beta_2$ is equal to 1.025 for MET-2. The Sq Res line shows the deviation between the model/fitted curve and the absorbance profile curve, and by 350 nm, it effectively overlaps the baseline, indicating the excellent fit of the model/fitted curve.

Multiplying the 0.313 wt. % concentration in the MET-1 reference profile with $\beta_1$ (0.092) results in a predicted concentration of MET-1 in the control solution of approximately 0.029 wt. % (actual is 0.026 wt. %). Likewise, multiplying the 0.35 wt. % concentration in the MET-2 reference profile with $\beta_2$ (1.025) results in a predicted concentration of MET-2 in the control solution of approximately 0.359 wt. % (actual is 0.35 wt. %). Thus, this method for simultaneously determining the concentrations of MET-1 and MET-2 results in very accurate predictions of the respective concentrations.

Figure 11:
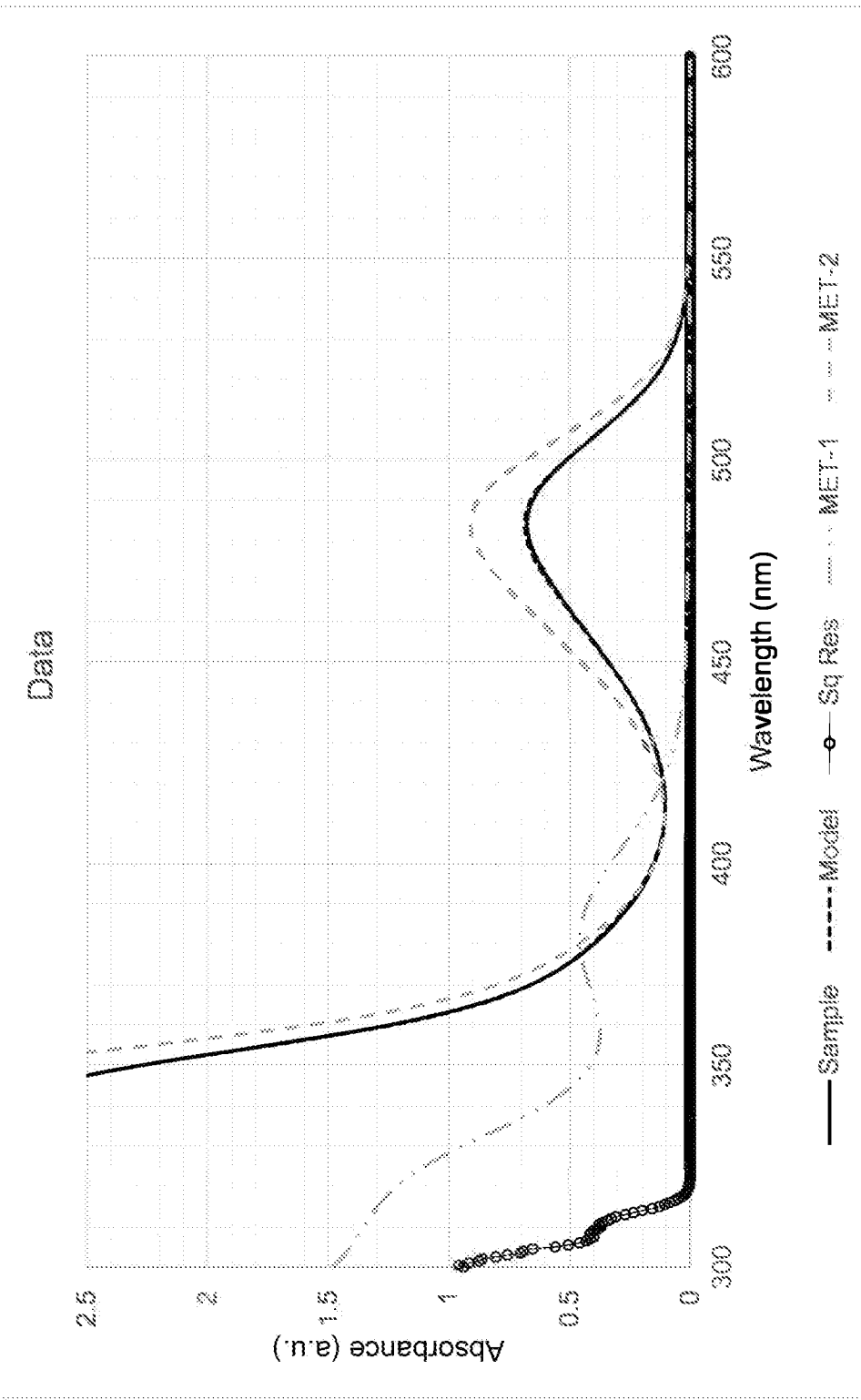
FIG. 11 presents plots of the UV-Vis absorbance profiles as a function of wavelength for MET-1, MET-2, and a mixture of MET-1 and MET-2, in 1-hexene/toluene, and a fitted model curve, for Example 2.

In Example 2, the same reference absorbance profiles for MET-1 and MET-2 as described in Example 1 were used, and these reference profiles are plotted in FIG. 11. A sample solution in which the exact MET-1 and MET-2 concentrations were not known was evaluated in Example 2. The only known information on the sample solution was that it contained the same solvent mixture (1-hexene:toluene at a 9:1 weight ratio) and it had a "target" MET-2 concentration of 0.25 wt. %, although the exact concentration was not known.

Absorbance spectra for the sample solution of MET-1 and MET-2 in 1-hexene:toluene (9:1, weight basis) at a 1 mm path length was obtained in the same manner as described above, using only 1-hexene/toluene in the reference cell. The sample absorbance profile for the sample solution containing both MET-1 and MET-2 is plotted in FIG. 11.

Using multiple regression, a curve having the formula "$\beta_1 F_1 + \beta_2 F_2$" was fit to the sample absorbance profile over the 300-600 nm range. In this formula, $\beta_1$ is the weighting coefficient for MET-1, $F_1$ is the reference absorbance profile for MET-1 (at 0.313 wt. %), $\beta_2$ is the weighting coefficient for MET-2, and $F_2$ is the reference absorbance profile for MET-2 (at 0.35 wt. %). The model curve for the formula $\beta_1F_1+\beta_2F_2$ is plotted in FIG. 11, where the $R^2$ value is 0.99991. In FIG. 11, the sample absorbance profile curve and the model/fitted curve completely overlap, and cannot be distinguished visually. For the model curve having formula "$\beta_1F_1+\beta_2F_2$" in FIG. 11, $\beta_1$ is equal 0.131 for MET-1 and $\beta_2$ is equal to 0.752 for MET-2.

Multiplying the 0.313 wt. % concentration in the MET-1 reference profile with $\beta_1$ (0.131) results in a predicted concentration of MET-1 in the sample solution of approximately 0.041 wt. %. Likewise, multiplying the 0.35 wt. % concentration in the MET-2 reference profile with $\beta_2$ (0.752) results in a predicted concentration of MET-2 in the sample solution of approximately 0.263 wt. %. Thus, this method for determining the concentrations of MET-1 and MET-2 can be used to determine "unknown" concentrations of MET-1 and MET-2, even when one is present in a large excess (there was over 6 times as much MET-2 in the sample solution of Example 2, as compared to MET-1), and when the UV-Vis absorbance bands significantly overlap (the characteristic peak of MET-1 at 380 nm is difficult to distinguish due to the overlapping absorbance from MET-2 in that range).

Figure 12:
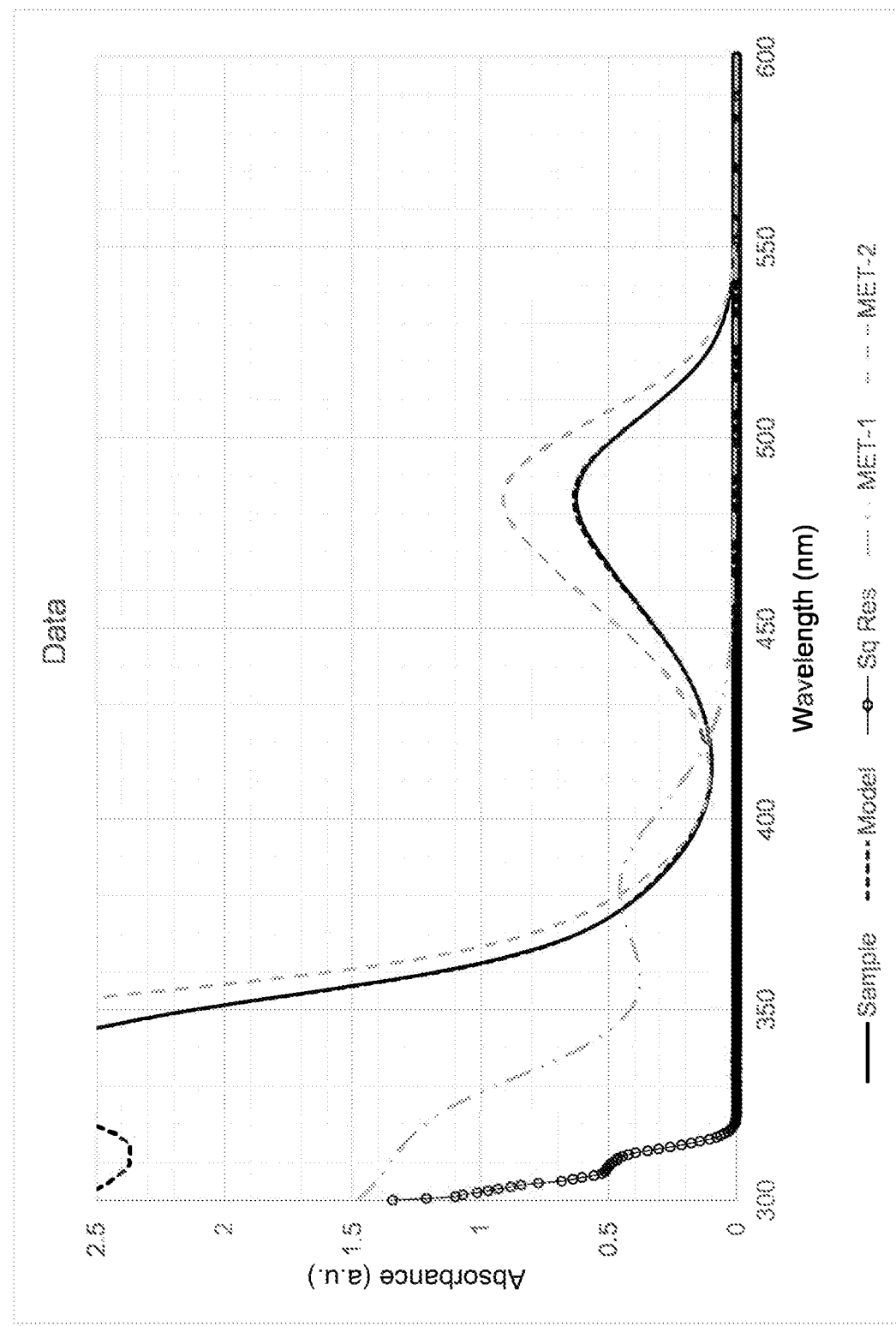
FIG. 12 presents plots of the UV-Vis absorbance profiles as a function of wavelength for MET-1, MET-2, and a mixture of MET-1 and MET-2, in 1-hexene/toluene, and a fitted model curve, for Example 3.

In Example 3, the same reference absorbance profiles for MET-1 and MET-2 as described in Example 1 were used, and these reference profiles are plotted in FIG. 12. A sample solution in which the exact MET-1 and MET-2 concentrations were not known was evaluated in Example 3. The only known information on the sample solution was that it contained the same solvent mixture (1-hexene:toluene at a 9:1 weight ratio) and it had a "target" MET-2 concentration of 0.25 wt. %, although the exact concentration was not known.

Absorbance spectra for the sample solution of MET-1 and MET-2 in 1-hexene:toluene (9:1, weight basis) at a 1 mm path length was obtained in the same manner as described above, using only 1-hexene/toluene in the reference cell. The sample absorbance profile for the sample solution containing both MET-1 and MET-2 is plotted in FIG. 12.

Using multiple regression, a curve having the formula "$\beta_1F_1+\beta_2F_2$" was fit to the sample absorbance profile over the 300-600 nm range. In this formula, $\beta_1$ is the weighting coefficient for MET-1, $F_1$ is the reference absorbance profile for MET-1 (at 0.313 wt. %), $\beta_2$ is the weighting coefficient for MET-2, and $F_2$ is the reference absorbance profile for MET-2 (at 0.35 wt. %). The model curve for the formula $\beta_1F_1+\beta_2F_2$ is plotted in FIG. 12, where the $R^2$ value is 0.99988. In FIG. 12, the sample absorbance profile curve and the model/fitted curve completely overlap, and cannot be distinguished visually. For the model curve having formula "$\beta_1F_1+\beta_2F_2$" in FIG. 12, $\beta_1$ is equal 0.130 for MET-1 and $\beta_2$ is equal to 0.697 for MET-2.

Multiplying the 0.313 wt. % concentration in the MET-1 reference profile with $\beta_1$ (0.130) results in a predicted concentration of MET-1 in the sample solution of approximately 0.041 wt. %. Likewise, multiplying the 0.35 wt. % concentration in the MET-2 reference profile with $\beta_2$ (0.697) results in a predicted concentration of MET-2 in the sample solution of approximately 0.244 wt. %. Thus, this method for determining the concentrations of MET-1 and MET-2 can be used to determine "unknown" concentrations of MET-1 and MET-2, even when one is present in a large excess, and when the UV-Vis absorbance bands significantly overlap.

Figure 13:
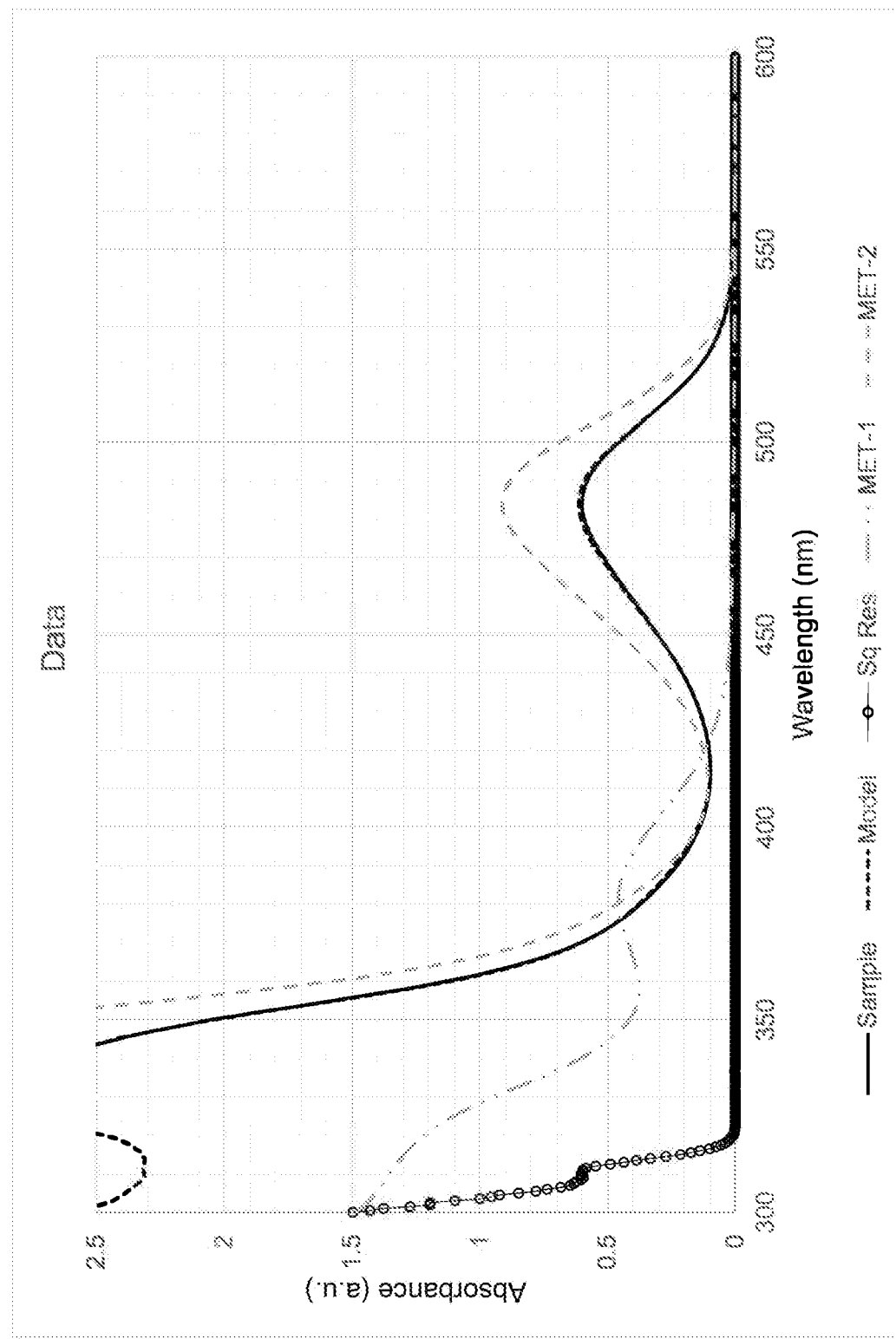
FIG. 13 presents plots of the UV-Vis absorbance profiles as a function of wavelength for MET-1, MET-2, and a mixture of MET-1 and MET-2, in 1-hexene/toluene, and a fitted model curve, for Example 4.

In Example 4, the same reference absorbance profiles for MET-1 and MET-2 as described in Example 1 were used, and these reference profiles are plotted in FIG. 13. A sample solution in which the exact MET-1 and MET-2 concentrations were not known was evaluated in Example 4. The only known information on the sample solution was that it contained the same solvent mixture (1-hexene:toluene at a 9:1 weight ratio) and it had a "target" MET-2 concentration of 0.25 wt. %, although the exact concentration was not known.

Absorbance spectra for the sample solution of MET-1 and MET-2 in 1-hexene:toluene (9:1, weight basis) at a 1 mm path length was obtained in the same manner as described above, using only 1-hexene/toluene in the reference cell. The sample absorbance profile for the sample solution containing both MET-1 and MET-2 is plotted in FIG. 13.

Using multiple regression, a curve having the formula "$\beta_1F_1+\beta_2F_2$" was fit to the sample absorbance profile over the 300-600 nm range. In this formula, $\beta_1$ is the weighting coefficient for MET-1, $F_1$ is the reference absorbance profile for MET-1 (at 0.313 wt. %), $\beta_2$ is the weighting coefficient for MET-2, and $F_2$ is the reference absorbance profile for MET-2 (at 0.35 wt. %). The model curve for the formula $\beta_1F_1+\beta_2F_2$ is plotted in FIG. 13, where the $R^2$ value is 0.99983. In FIG. 13, the sample absorbance profile curve and the model/fitted curve completely overlap, and cannot be distinguished visually. For the model curve having formula "$\beta_1F_1+\beta_2F_2$" in FIG. 13, $\beta_1$ is equal 0.149 for MET-1 and $\beta_2$ is equal to 0.671 for MET-2.

Multiplying the 0.313 wt. % concentration in the MET-1 reference profile with $\beta_1$ (0.149) results in a predicted concentration of MET-1 in the sample solution of approximately 0.047 wt. %. Likewise, multiplying the 0.35 wt. % concentration in the MET-2 reference profile with $\beta_2$ (0.671) results in a predicted concentration of MET-2 in the sample solution of approximately 0.235 wt. %. Thus, this method for determining the concentrations of MET-1 and MET-2 can be used to determine "unknown" concentrations of MET-1 and MET-2, even when one is present in a large excess, and when the UV-Vis absorbance bands significantly overlap.

Solutions Containing Three Transition Metal Compounds

The methods, processes, and systems disclosed herein also can be applied to a solution containing three or more transition metal compounds.

In Example 5, a stock solution of MET-1 in 1-hexene:toluene (9:1, weight basis) was prepared at a concentration of 0.098 wt. %. Absorbance spectra for MET-1 (1 mm path length) at a concentration of 0.098 wt. % was obtained in the same manner as described above, using only solvent (1-hexene/toluene) in the reference cell. This reference absorbance profile for MET-1 is plotted in FIG. 14. Similarly, a stock solution of MET-2 in 1-hexene:toluene (9:1, weight basis) was prepared at a concentration of 0.202 wt. %. Absorbance spectra for MET-2 (1 mm path length) at a concentration of 0.202 wt. % was obtained in the same manner as described above, using only solvent (1-hexene/toluene) in the reference cell. This reference absorbance profile for MET-2 also is plotted in FIG. 14. Likewise, a stock solution of MET-3 in 1-hexene:toluene (9:1, weight basis) was prepared at a concentration of 0.190 wt. %. Absorbance spectra for MET-3 (1 mm path length) at a concentration of 0.190 wt. % was obtained in the same manner as described above, using only solvent (1-hexene/toluene) in the reference cell. This reference absorbance profile for MET-3 also is plotted in FIG. 14.

From the respective stock solutions, a sample solution containing MET-1, MET-2, and MET-3 at known concentrations was prepared: MET-1 (at 0.419 wt. %), MET-2 (at 0.247 wt. %), and MET-3 (at 0.161 wt. %). Absorbance spectra for this solution of MET-1, MET-2, and MET-3 in 1-hexene:toluene (9:1, weight basis) at a 1 mm path length was obtained in the same manner as described above, using only 1-hexene/toluene in the reference cell. This sample absorbance profile for the solution containing MET-1, MET-2, and MET-3 is plotted in FIG. 14.

Figure 14:
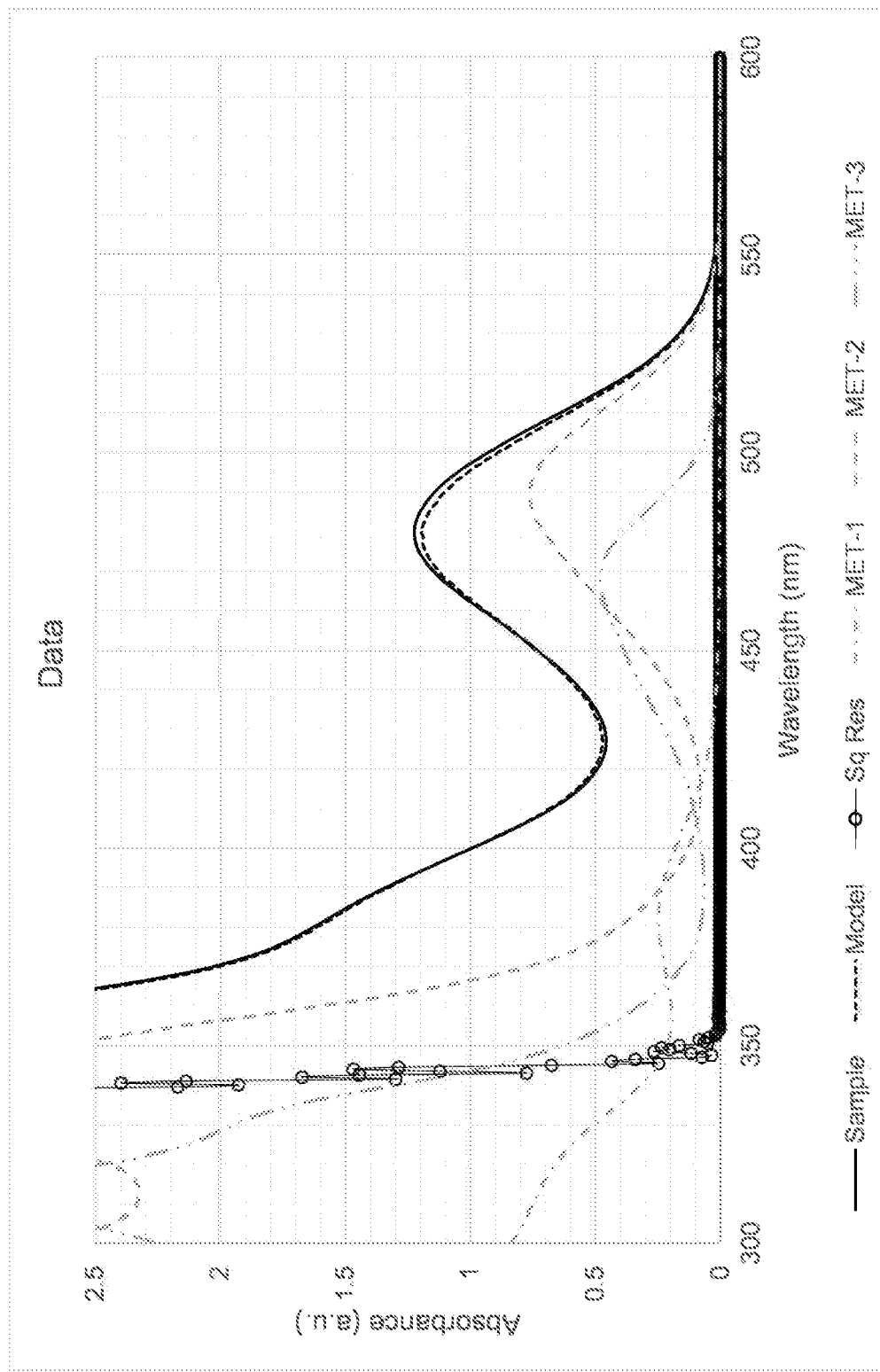
FIG. 14 presents plots of the UV-Vis absorbance profiles as a function of wavelength for MET-1, MET-2, MET-3, and a mixture of MET-1, MET-2, and MET-3 in 1-hexene/toluene, and a fitted model curve, for Example 5.

Using a multiple regression feature in Microsoft Excel, a curve having the formula "$\beta_1 F_1 + \beta_2 F_2 + \beta_3 F_3$" was fit to the sample absorbance profile over the 350-600 nm range. In this formula, $\beta_1$ is the weighting coefficient for MET-1, $F_1$ is the reference absorbance profile for MET-1 (at 0.098 wt. %), $\beta_2$ is the weighting coefficient for MET-2, $F_2$ is the reference absorbance profile for MET-2 (at 0.202 wt. %), $\beta_3$ is the weighting coefficient for MET-3, and $F_3$ is the reference absorbance profile for MET-3 (at 0.190 wt. %). The model curve for the formula $\beta_1 F_1 + \beta_2 F_2 + \beta_3 F_3$ is plotted in FIG. 14, where the $R^2$ value is 0.99887. In FIG. 14, the sample absorbance profile curve and the model/fitted curve almost completely overlap, and are difficult to be distinguished visually. For the model curve having formula "$\beta_1 F_1 + \beta_2 F_2 + \beta_3 F_3$" in FIG. 14, $\beta_1$ is equal to 4.295 for MET-1, $\beta_2$ is equal to 1.193 for MET-2, and $\beta_3$ is equal to 0.867 for MET-3. The Sq Res line shows the deviation between the model/fitted curve and the sample absorbance profile curve, and by ~360 nm, it effectively overlaps the baseline, indicating the excellent fit of the model/fitted curve.

Multiplying the 0.098 wt. % concentration in the MET-1 reference profile with $\beta_1$ (4.295) results in a predicted concentration of MET-1 in the sample solution of approximately 0.421 wt. % (actual is 0.419 wt. %). Likewise, multiplying the 0.202 wt. % concentration in the MET-2 reference profile with $\beta_2$ (1.193) results in a predicted concentration of MET-2 in the sample solution of approximately 0.241 wt. % (actual is 0.247 wt. %). Similarly, multiplying the 0.190 wt. % concentration in the MET-3 reference profile with $\beta_3$ (0.867) results in a predicted concentration of MET-3 in the sample solution of approximately 0.165 wt. % (actual is 0.161 wt. %). Thus, this method for simultaneously determining the concentrations of MET-1, MET-2, and MET-3 results in very accurate predictions of the respective concentrations.

Figure 15:
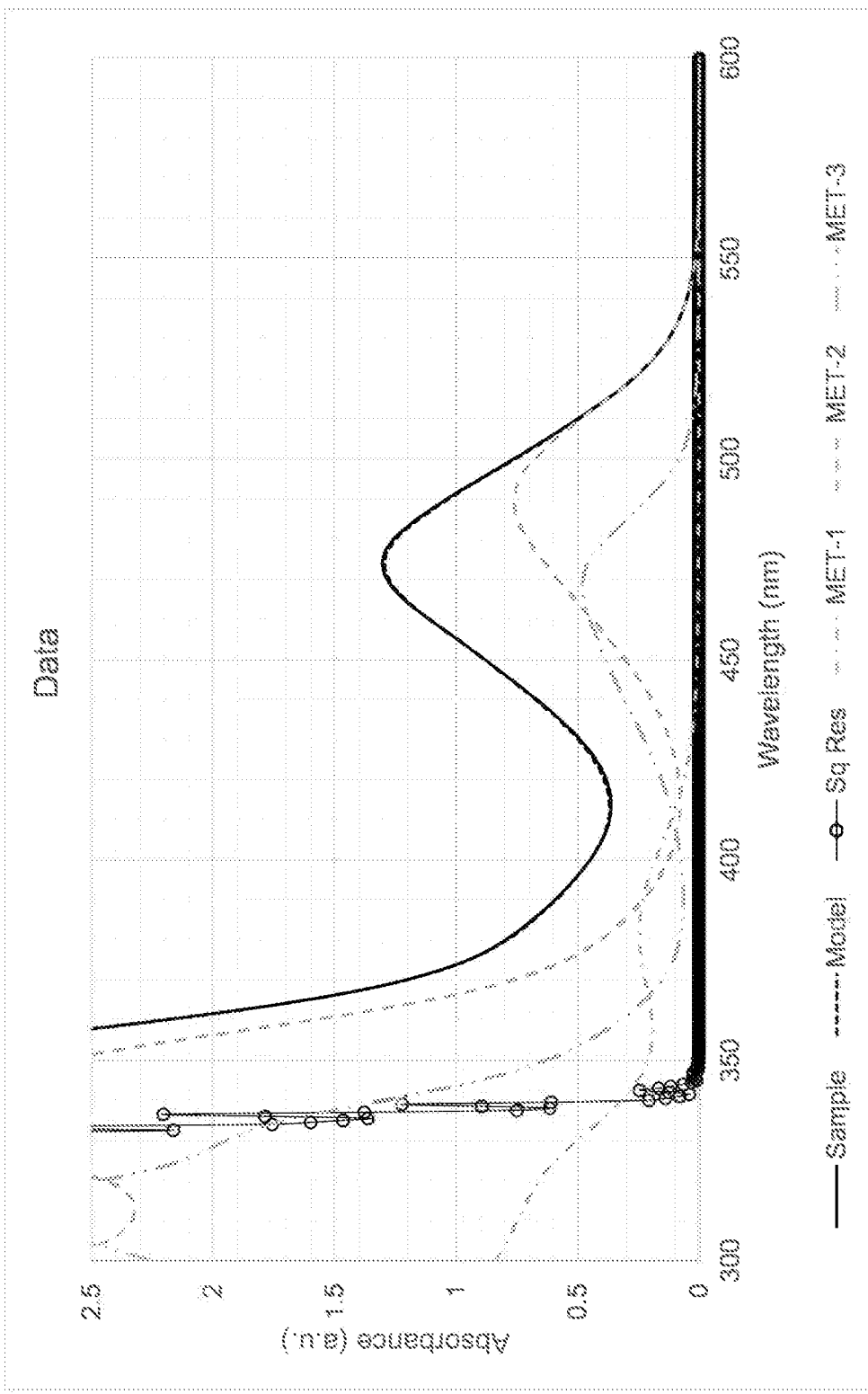
FIG. 15 presents plots of the UV-Vis absorbance profiles as a function of wavelength for MET-1, MET-2, MET-3, and a mixture of MET-1, MET-2, and MET-3 in 1-hexene/toluene, and a fitted model curve, for Example 6.

In Example 6, the same reference absorbance profiles for MET-1, MET-2, and MET-3 as described in Example 5 were used, and these reference profiles are plotted in FIG. 15. A sample solution containing MET-1, MET-2, and MET-3 at known concentrations was prepared: MET-1 (at 0.132 wt. %), MET-2 (at 0.184 wt. %), and MET-3 (at 0.265 wt. %). Absorbance spectra for this solution of MET-1, MET-2, and MET-3 in 1-hexene:toluene (9:1, weight basis) at a 1 mm path length was obtained in the same manner as described above, using only 1-hexene/toluene in the reference cell. This sample absorbance profile for the solution containing MET-1, MET-2, and MET-3 is plotted in FIG. 15.

Using multiple regression, a curve having the formula "$\beta_1 F_1 + \beta_2 F_2 + \beta_3 F_3$" was fit to the sample absorbance profile over the 350-600 nm range. In this formula, $\beta_1$ is the weighting coefficient for MET-1, $F_1$ is the reference absorbance profile for MET-1 (at 0.098 wt. %), $\beta_2$ is the weighting coefficient for MET-2, $F_2$ is the reference absorbance profile for MET-2 (at 0.202 wt. %), $\beta_3$ is the weighting coefficient for MET-3, and $F_3$ is the reference absorbance profile for MET-3 (at 0.190 wt. %). The model curve for the formula $\beta_1 F_1 + \beta_2 F_2 + \beta_3 F_3$ is plotted in FIG. 15, where the $R^2$ value is 0.99995. In FIG. 15, the sample absorbance profile curve and the model/fitted curve completely overlap, and cannot be distinguished visually. For the model curve having formula "$\beta_1 F_1 + \beta_2 F_2 + \beta_3 F_3$" in FIG. 15, $\beta_1$ is equal to 1.190 for MET-1, $\beta_2$ is equal to 0.924 for MET-2, and $\beta_3$ is equal to 1.539 for MET-3. The Sq Res line shows the deviation between the model/fitted curve and the sample absorbance profile curve, and by ~360 nm, it effectively overlaps the baseline, indicating the excellent fit of the model/fitted curve.

Multiplying the 0.098 wt. % concentration in the MET-1 reference profile with $\beta_1$ (1.190) results in a predicted concentration of MET-1 in the sample solution of approximately 0.117 wt. % (actual is 0.132 wt. %). Likewise, multiplying the 0.202 wt. % concentration in the MET-2 reference profile with $\beta_2$ (0.924) results in a predicted concentration of MET-2 in the sample solution of approximately 0.187 wt. % (actual is 0.184 wt. %). Similarly, multiplying the 0.190 wt. % concentration in the MET-3 reference profile with $\beta_3$ (1.539) results in a predicted concentration of MET-3 in the sample solution of approximately 0.292 wt. % (actual is 0.265 wt. %). Thus, this method for simultaneously determining the concentrations of MET-1, MET-2, and MET-3 results in very accurate predictions of the respective concentrations.

Figure 16:
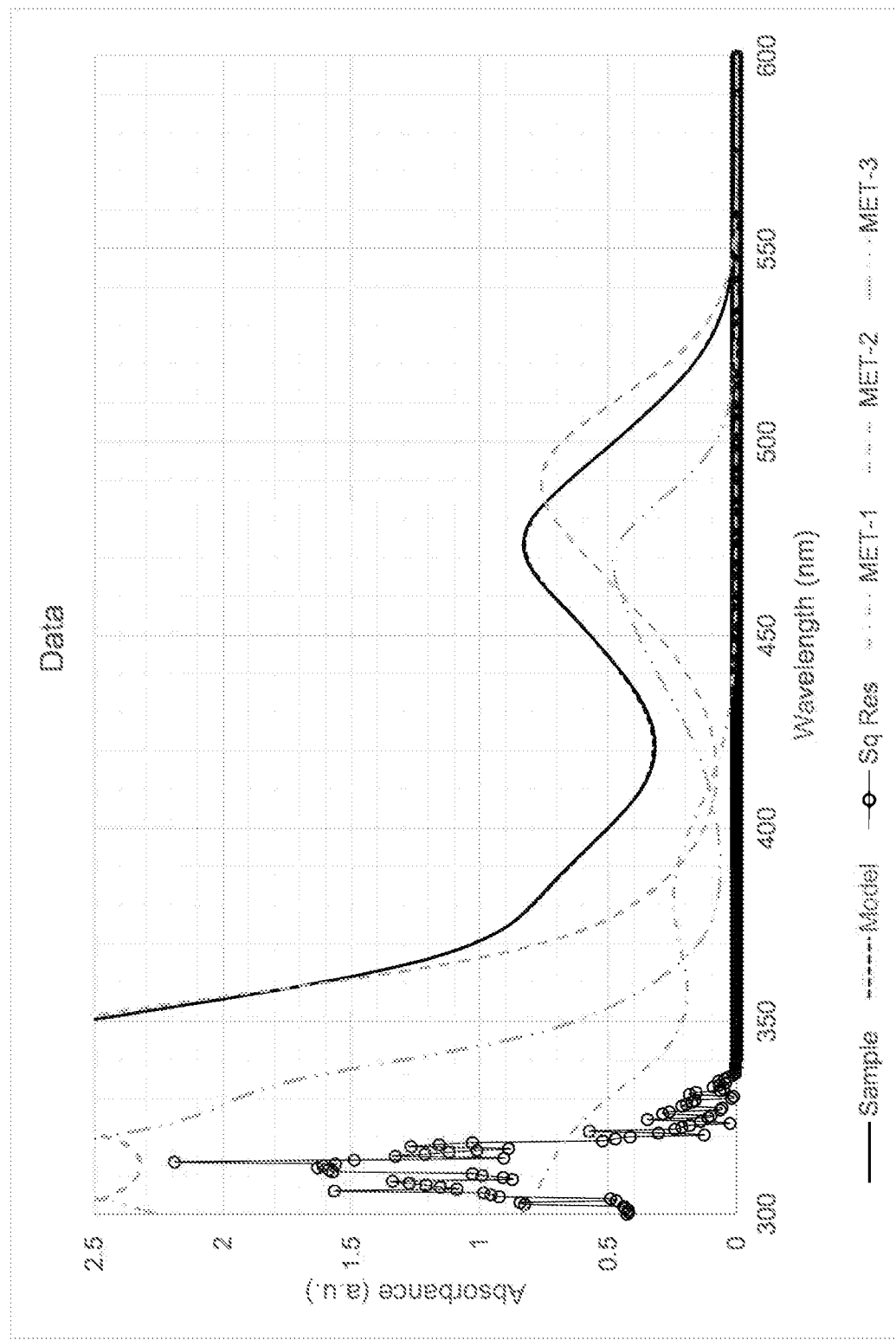
FIG. 16 presents plots of the UV-Vis absorbance profiles as a function of wavelength for MET-1, MET-2, MET-3, and a mixture of MET-1, MET-2, and MET-3 in 1-hexene/toluene, and a fitted model curve, for Example 7.

In Example 7, the same reference absorbance profiles for MET-1, MET-2, and MET-3 as described in Example 5 were used, and these reference profiles are plotted in FIG. 16. A sample solution containing MET-1, MET-2, and MET-3 at known concentrations was prepared: MET-1 (at 0.196 wt. %), MET-2 (at 0.121 wt. %), and MET-3 (at 0.184 wt. %). Absorbance spectra for this solution of MET-1, MET-2, and MET-3 in 1-hexene:toluene (9:1, weight basis) at a 1 mm path length was obtained in the same manner as described above, using only 1-hexene/toluene in the reference cell. This sample absorbance profile for the solution containing MET-1, MET-2, and MET-3 is plotted in FIG. 16.

Using multiple regression, a curve having the formula "$\beta_1 F_1 + \beta_2 F_2 + \beta_3 F_3$" was fit to the sample absorbance profile over the 300-600 nm range. In this formula, $\beta_1$ is the weighting coefficient for MET-1, $F_1$ is the reference absorbance profile for MET-1 (at 0.098 wt. %), $\beta_2$ is the weighting coefficient for MET-2, $F_2$ is the reference absorbance profile for MET-2 (at 0.202 wt. %), $\beta_3$ is the weighting coefficient for MET-3, and $F_3$ is the reference absorbance profile for MET-3 (at 0.190 wt. %). The model curve for the formula $\beta_1 F_1 + \beta_2 F_2 + \beta_3 F_3$ is plotted in FIG. 16, where the $R^2$ value is 0.99998. In FIG. 16, the sample absorbance profile curve and the model/fitted curve completely overlap, and cannot be distinguished visually. For the model curve having formula "$\beta_1 F_1 + \beta_2 F_2 + \beta_3 F_3$" in FIG. 16, $\beta_1$ is equal to 1.959 for MET-1, $\beta_2$ is equal to 0.578 for MET-2, and $\beta_3$ is equal to 0.988 for MET-3. The Sq Res line shows the deviation between the model/fitted curve and the sample absorbance profile curve, and by 350 nm, it effectively overlaps the baseline, indicating the excellent fit of the model/fitted curve.

Multiplying the 0.098 wt. % concentration in the MET-1 reference profile with $\beta_1$ (1.959) results in a predicted concentration of MET-1 in the sample solution of approximately 0.192 wt. % (actual is 0.196 wt. %). Likewise, multiplying the 0.202 wt. % concentration in the MET-2 reference profile with $\beta_2$ (0.578) results in a predicted concentration of MET-2 in the sample solution of approximately 0.117 wt. % (actual is 0.121 wt. %). Similarly, multiplying the 0.190 wt. % concentration in the MET-3 reference profile with $\beta_3$ (0.988) results in a predicted concentration of MET-3 in the sample solution of approximately 0.188 wt. % (actual is 0.184 wt. %). Thus, this method for simultaneously determining the concentrations of MET-1, MET-2, and MET-3 results in very accurate predictions of the respective concentrations.

Figure 17:
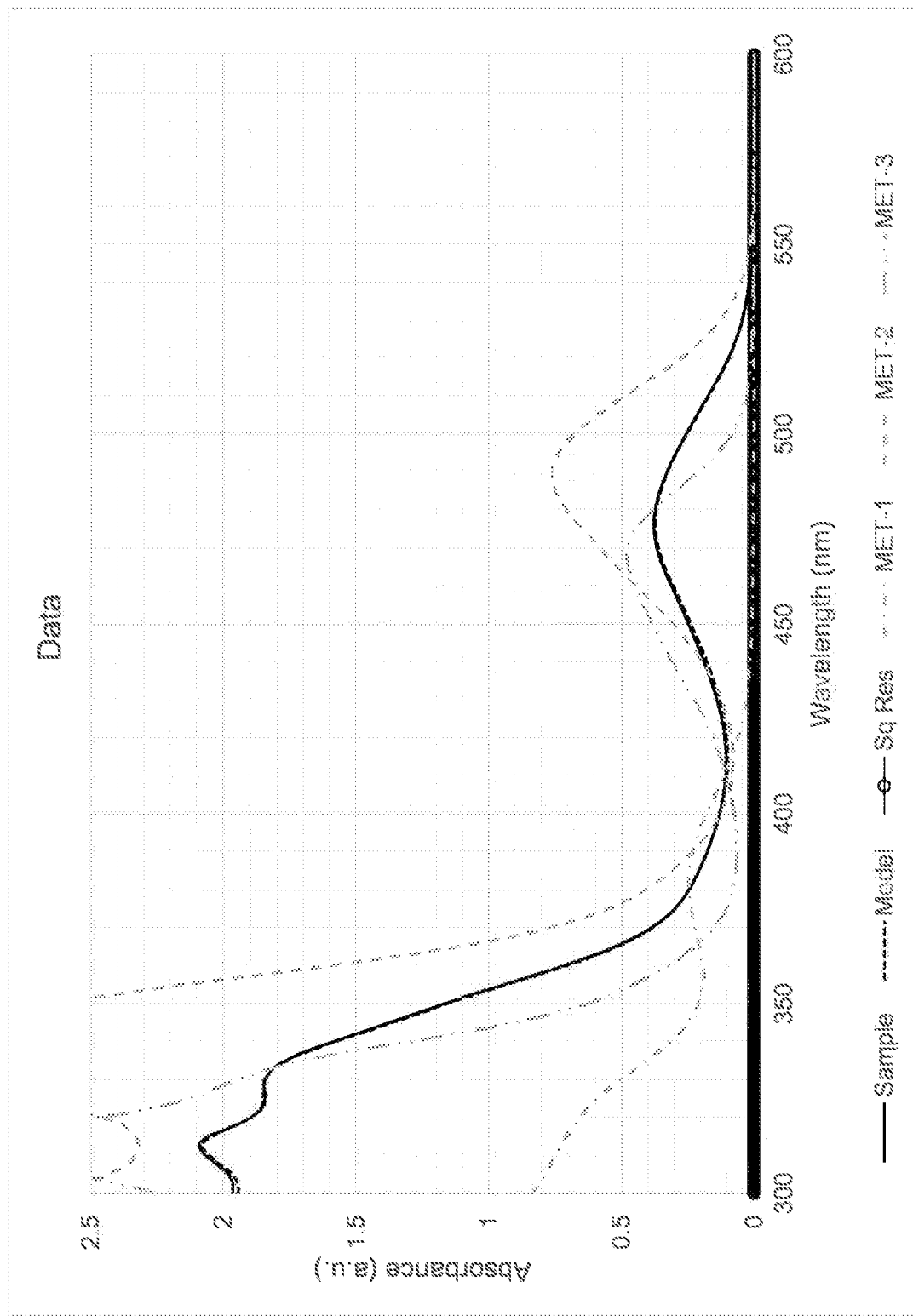
FIG. 17 presents plots of the UV-Vis absorbance profiles as a function of wavelength for MET-1, MET-2, MET-3, and a mixture of MET-1, MET-2, and MET-3 in 1-hexene/toluene, and a fitted model curve, for Example 8.

In Example 8, the same reference absorbance profiles for MET-1, MET-2, and MET-3 as described in Example 5 were used, and these reference profiles are plotted in FIG. 17. A sample solution containing MET-1, MET-2, and MET-3 at known concentrations was prepared: MET-1 (at 0.033 wt. %), MET-2 (at 0.067 wt. %), and MET-3 (at 0.063 wt. %). Absorbance spectra for this solution of MET-1, MET-2, and MET-3 in 1-hexene:toluene (9:1, weight basis) at a 1 mm path length was obtained in the same manner as described above, using only 1-hexene/toluene in the reference cell. This sample absorbance profile for the solution containing MET-1, MET-2, and MET-3 is plotted in FIG. 17.

Using multiple regression, a curve having the formula "$\beta_1 F_1 + \beta_2 F_2 + \beta_3 F_3$" was fit to the sample absorbance profile over the 300-600 nm range. In this formula, $\beta_1$ is the weighting coefficient for MET-1, $F_1$ is the reference absorbance profile for MET-1 (at 0.098 wt. %), $\beta_2$ is the weighting coefficient for MET-2, $F_2$ is the reference absorbance profile for MET-2 (at 0.202 wt. %), $\beta_3$ is the weighting coefficient for MET-3, and $F_3$ is the reference absorbance profile for MET-3 (at 0.190 wt. %). The model curve for the formula $\beta_1 F_1 + \beta_2 F_2 + \beta_3 F_3$ is plotted in FIG. 17, where the $R^2$ value is 0.99975. In FIG. 17, the sample absorbance profile curve and the model/fitted curve completely overlap, and cannot be distinguished visually. For the model curve having formula "$\beta_1 F_1 + \beta_2 F_2 + \beta_3 F_3$" in FIG. 17, $\beta_1$ is equal to 0.341 for MET-1, $\beta_2$ is equal to 0.330 for MET-2, and $\beta_3$ is equal to 0.350 for MET-3. The Sq Res line shows the deviation between the model/fitted curve and the sample absorbance profile curve, and by ~310 nm, it effectively overlaps the baseline, indicating the excellent fit of the model/fitted curve.

Multiplying the 0.098 wt. % concentration in the MET-1 reference profile with $\beta_1$ (0.341) results in a predicted concentration of MET-1 in the sample solution of approximately 0.033 wt. % (actual is 0.033 wt. %). Likewise, multiplying the 0.202 wt. % concentration in the MET-2 reference profile with $\beta_2$ (0.330) results in a predicted concentration of MET-2 in the sample solution of approximately 0.067 wt. % (actual is 0.067 wt. %). Similarly, multiplying the 0.190 wt. % concentration in the MET-3 reference profile with $\beta_3$ (0.350) results in a predicted concentration of MET-3 in the sample solution of approximately 0.067 wt. % (actual is 0.063 wt. %). Thus, this method for simultaneously determining the concentrations of MET-1, MET-2, and MET-3 results in very accurate predictions of the respective concentrations.

Catalyst Preparation with Two Transition Metal Compounds

Figure 18:
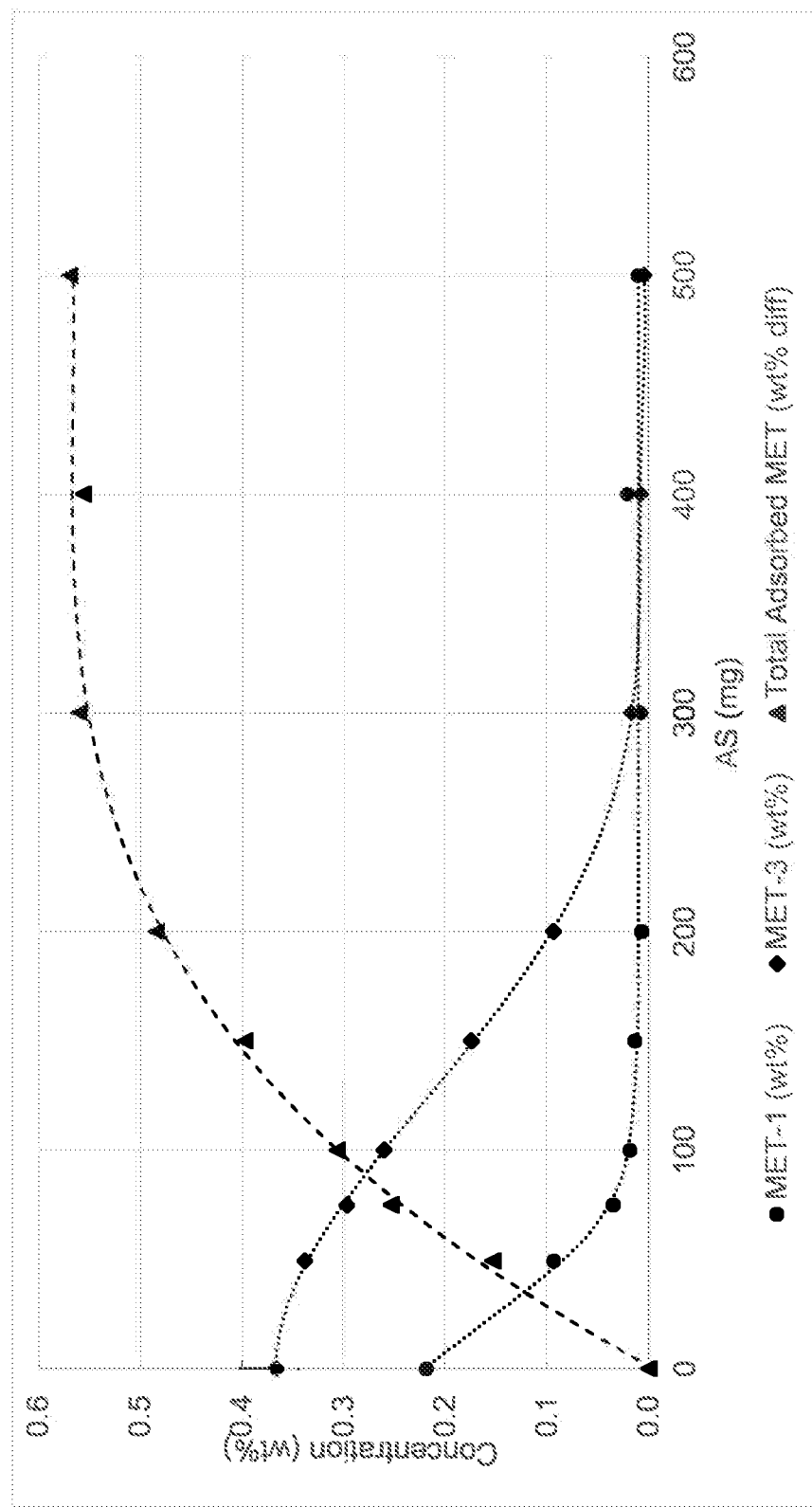
FIG. 18 presents a plot of the MET-1 and MET-3 solution concentrations, and the total absorbed metallocene, as a function of the amount of activator-support.

Stock solutions of MET-1 in toluene and MET-3 in toluene were prepared, and then mixed for 1 hr at room temperature with different amounts of a sulfated alumina activator-support (AS) to produce a supported catalyst system containing approximately 0.22 wt. % MET-1 and 0.37 wt. % MET 3. No co-catalyst was added, so that the interactions between the transition metal compounds and the activator-support could be investigated. FIG. 18 shows the respective transition metal compound concentrations that are present with no activator-support present (zero mg). As increasing amounts of the activator-support are added (from 50 mg to 500 mg), the respective amounts of "free" MET-1 and MET-3 present in solution (e.g., not impregnated in, on, or associated with the activator-support) decreased. The respective concentrations of MET-1 and MET-3 were determined by separating the solution (and "free" MET-1 and MET-3) from the solid catalyst components via filtration, and then the solution concentrations were determined as described herein and demonstrated in FIGS. 10-17.

As shown in FIG. 18, when 300 mg (or more) of activator-support (AS) were present, there was no "free" MET-1 and MET-3 in solution—all of the MET-1 and MET-3 were absorbed or impregnated on the solid activator-support. Also of significant interest, FIG. 18 demonstrates that MET-1 was absorbed more quickly by the activator-support (preferentially absorbed). There was virtually no "free" MET-1 in solution at activator-support quantities of 150 mg or more.

Figure 19:
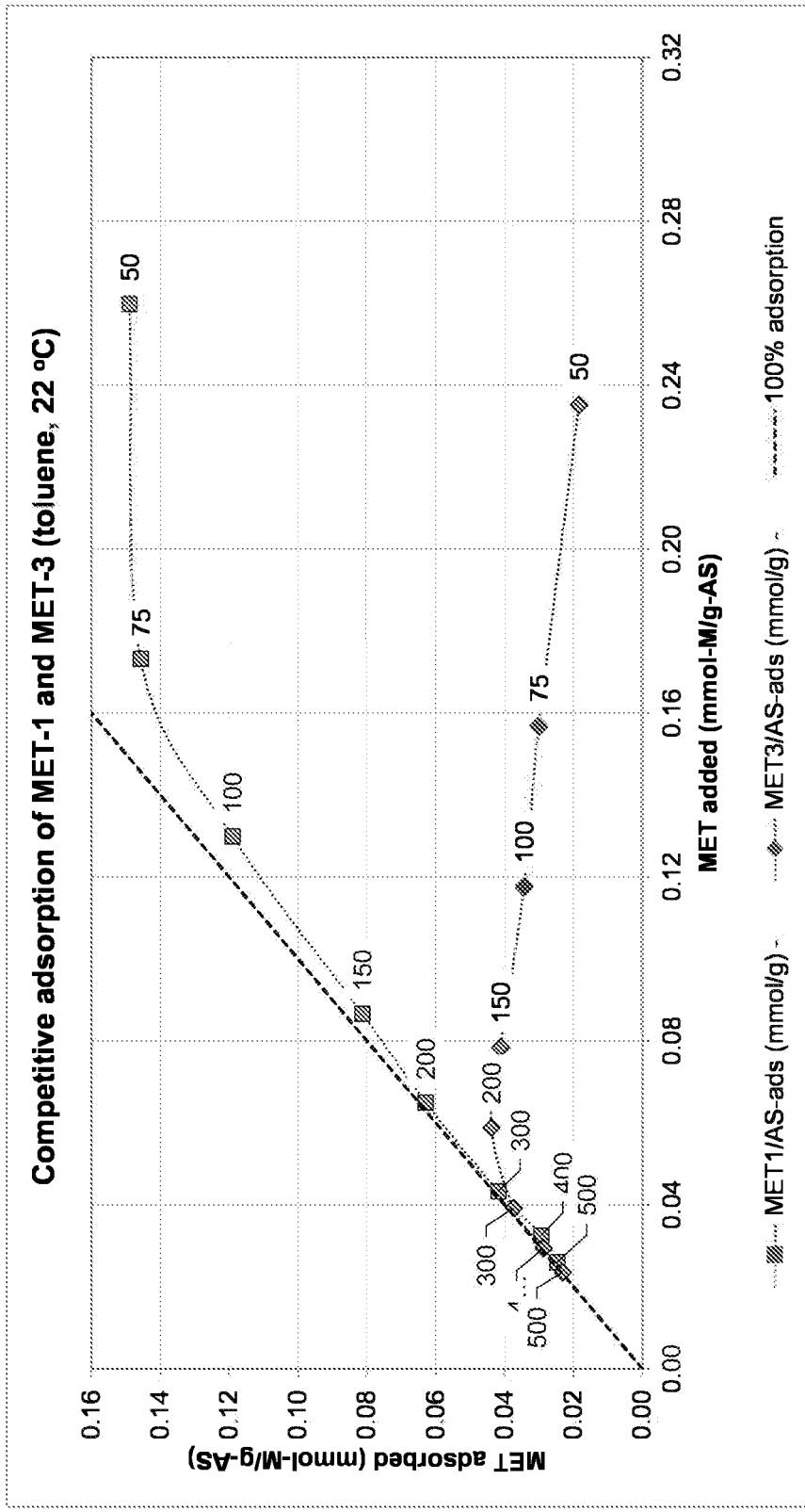
FIG. 19 presents a plot of the amount of MET-1 and MET-3 absorbed versus the total amount of MET-1 and total amount MET-3, at different amounts of activator-support.

FIG. 19 illustrates the data of FIG. 18 in another way. The dashed line (100% adsorption) starting at the origin reflects conditions where the amount of activator-support (AS) present is such that all of the MET-1 and MET-3 present is absorbed or impregnated on the activator—support—no "free" MET-1 and MET-3. This occurs at activator-support loadings in the 300-500 mg range. The faster relative absorption of MET-1 (as compared to MET-3) is demonstrated by the MET-1 line (as a function of activator-support) approaching the dashed line at much lower activator-support loadings. For instance, when 100 mg of activator-support were present, the MET-1 line is very close to the dashed line (~0.12 MET-1 was absorbed of the ~0.13 MET-1 added), whereas the MET-3 line is not close to the dashed line. At 100 mg of activator-support, only ~0.035 MET-3 was absorbed of the ~0.12 MET-3 added. Thus, to produce a catalyst composition with an equal amount of absorbed MET-1 and MET-3 at a fixed quantity of 100 mg of activator-support, the amount of MET-1 added can decreased, the amount of MET-3 added can be increased, or both.

The amount of "free" transition metal compounds in solution, as compared to that absorbed or impregnated onto the solid activator, is extremely important for catalyst preparation. From the data in FIGS. 18-19, for example, approximately 300 mg of the solid activator were sufficient to eliminate any "free" transition metal compound—all was absorbed or impregnated. Thus, if the typical loading of the solid activator was 500 mg or 600 mg, or more, during the catalyst preparation step, this data demonstrates that the amount of solid activator can be reduced significantly, thus resulting in reduced waste, and improved cost and efficiency.

As another example, if the MET-1 and MET-3 catalyst system was used to produce a polymer that required improvement in a property that is positively impacted by the addition of more MET-1, the data in FIGS. 18-19 demonstrate that this can be easily accomplished without the addition of more of the catalyst composition. Rather, given the rapid and preferential absorption of MET-1, the amount of MET-1 fed to the catalyst preparation vessel can be increased, resulting in an increased relative amount versus the amount of MET-3 present in the overall catalyst composition.

As one of skill in the art would readily recognize, numerous other possibilities of changing and optimizing the catalyst system can be ascertained from the UV-Vis data similar to that shown representatively in FIGS. 18-19, and adjusting a relative amount of at least one component of the catalyst composition based on the respective concentrations of the first and second transition metal compounds in the solution, determined by the UV-Vis methodology disclosed herein. Thus, depending upon the determined concentrations, the amount of the first transition metal compound in the catalyst composition can be increased or decreased, and/or the amount of the second transition metal compound in the catalyst composition can be increased or decreased, and/or the amount of the solid activator in the catalyst composition can be increased or decreased, and/or the amount of the co-catalyst in the catalyst composition can be increased or decreased, to optimize the catalyst composition with better certainty and predictability of the outcome.

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of" unless specifically stated otherwise):

Aspect 1. A method for determining a first concentration of a first transition metal compound and a second concentration of a second transition metal compound in a solution comprising the first transition metal compound and the second transition metal compound, the method comprising:

(i) providing a first reference absorbance profile ($F_1$) of the first transition metal compound in a first reference solution at a first known concentration, and a second reference absorbance profile ($F_2$) of the second transition metal compound in a second reference solution at a second known concentration;

(ii) submitting a sample of the solution to a sample chamber;

(iii) irradiating the sample in the chamber with a light beam at a wavelength in the UV-visible spectrum;

(iv) generating a sample absorbance profile of the sample, and calculating a curve having the formula $\beta_1 F_1 + \beta_2 F_2$ to fit the sample absorbance profile to a least-squares regression fit value ($R^2$) of at least 0.9; wherein:

$\beta_1$ is a first weighting coefficient;

$F_1$ is the first reference absorbance profile of the first transition metal compound in the first reference solution at the first known concentration;

$\beta_2$ is a second weighting coefficient; and $F_2$ is the second reference absorbance profile of the second transition metal compound in the second reference solution at the second known concentration; and (v) multiplying the first known concentration with $\beta_1$ to determine the first concentration of the first transition metal compound in the solution, and multiplying the second known concentration with $\beta_2$ to determine the second concentration of the second transition metal compound in the solution.

Aspect 2. The method defined in aspect 1, wherein the solution comprising the first transition metal compound and the second transition metal compound is a feed stream to a catalyst preparation vessel.

Aspect 3. The method defined in aspect 1, wherein the solution comprising the first transition metal compound and the second transition metal compound is a liquid (or homogeneous) catalyst system comprising the first transition metal compound, the second transition metal compound, and other catalyst components.

Aspect 4. The method defined in aspect 1, wherein the solution comprising the first transition metal compound and the second transition metal compound is a solution of a heterogeneous catalyst system (e.g., a solution prepared from a sample mixture of the catalyst system, such as from a catalyst preparation vessel), or a solution from a polymerization reactor (e.g., a solution prepared from a sample mixture from a polymerization reactor).

Aspect 5. A process for preparing a catalyst composition, the process comprising:

(I) contacting a first transition metal compound, a second transition metal compound, a solid activator, and an optional co-catalyst (e.g., in a catalyst preparation vessel) to form the catalyst composition;

(II) determining a first concentration of the first transition metal compound and a second concentration of the second transition metal compound in a solution containing the first transition metal compound and the second transition metal compound, wherein the solution is separated from (or obtained from) the catalyst composition, and the first concentration and the second concentration are determined by the method defined in aspect 1; and (III) adjusting a relative amount of at least one component of the catalyst composition based on the first concentration and/or the second concentration (or based on the determined concentrations).

Aspect 6. The process defined in aspect 5, wherein the first transition metal compound, the second transition metal compound, the solid activator, and the co-catalyst are contacted in step (I).

Aspect 7. The process defined in aspect 6, wherein a solution containing both the first and second transition metal compounds is contacted with the co-catalyst and a slurry of the solid activator in step (I).

Aspect 8. The process defined in any one of aspects 5-7, wherein the solution is separated from (or obtained from) the catalyst composition using any suitable technique or any technique disclosed herein, e.g., sieving (e.g., straining), filtering, centrifuging, settling, etc., or any combination thereof.

Aspect 9. The process defined in any one of aspects 5-8, wherein the relative amount of the first transition metal compound, the second transition metal compound, the solid activator, the co-catalyst (if used), or any combination thereof, is adjusted in step (III).

Aspect 10. A process for operating a polymerization reactor system, the process comprising:

(I) contacting a catalyst system comprising a first transition metal compound, a second transition metal compound, an activator, and an optional co-catalyst, with an olefin monomer and an optional olefin comonomer in a reactor within the polymerization reactor system under polymerization reaction conditions to produce an olefin polymer;

(II) determining a first concentration of the first transition metal compound and a second concentration of the second transition metal compound in a solution comprising the first transition metal compound and the second transition metal compound, the first concentration and the second concentration determined by the method defined in aspect 1; and (III) adjusting a first flow rate of the first transition metal compound and/or a second flow rate of second transition metal compound into the reactor when the first concentration and/or the second concentration has reached a predetermined level (or adjusting the first flow rate of the first transition metal compound based on the first determined concentration and/or adjusting the second flow rate of the second transition metal compound based on the second determined concentration).

Aspect 11. The process defined in aspect 10, wherein the solution comprising the first transition metal compound and the second transition metal compound is a feed stream to a catalyst preparation vessel, and the first flow rate and/or the second flow rate is/are controlled by adjusting a flow rate of a feed stream to the catalyst preparation vessel, and/or by adjusting a relative flow rate (ratio of first:second transition metal compound) to the catalyst preparation vessel, and/or by adjusting a flow rate of the catalyst system exiting the catalyst preparation vessel and entering the reactor.

Aspect 12. The process defined in aspect 10, wherein the catalyst system is a liquid (or homogeneous) catalyst system, and the solution comprising the first transition metal compound and the second transition metal compound is a sample of the liquid catalyst system, and wherein the first flow rate and/or the second flow rate is/are controlled by adjusting a relative flow rate (ratio of first:second transition metal compound) to the reactor, and/or by adjusting a flow rate of the liquid catalyst system entering the reactor.

Aspect 13. The process defined in aspect 10, wherein the polymerization reactor system comprises a polymerization reactor containing a mixture, and the solution comprising the first transition metal compound and the second transition metal compound is a solution prepared from a sample of the mixture from the polymerization reactor (e.g., a solution polymerization reactor, a slurry polymerization reactor), and wherein the first flow rate and/or the second flow rate is/are controlled by adjusting a relative flow rate (ratio of first:second transition metal compound) to the reactor, and/or by adjusting a flow rate of the catalyst system entering the polymerization reactor.

Aspect 14. The method or process defined in any one of the preceding aspects, wherein the sample chamber comprises a flow cell.

Aspect 15. The method or process defined in any one of aspects 1-14, wherein the wavelength is a single wavelength.

Aspect 16. The method or process defined in any one of aspects 1-14, wherein the wavelength is a range of wavelengths (e.g., a 200 nm or a 300 nm wavelength range).

Aspect 17. The method or process defined in any one of aspects 1-14 or 16, wherein the wavelength comprises wavelengths in the visible spectrum (from 380 nm to 780 nm).

Aspect 18. The method or process defined in any one of aspects 1-14 or 16, wherein the wavelength comprises wavelengths in the 200 nm to 750 nm range.

Aspect 19. The method or process defined in any one of aspects 1-14 or 16, wherein the wavelength comprises wavelengths in the 300 nm to 600 nm range.

Aspect 20. The method or process defined in any one of aspects 1-19, wherein the sample (or first reference, or second reference) absorbance profile comprises an absorbance peak at a single wavelength.

Aspect 21. The method or process defined in any one of aspects 1-19, wherein the sample (or first reference, or second reference) absorbance profile comprises an absorbance curve (e.g., peaks and/or areas under curves) over a range of wavelengths from 200 nm to 750 nm, or from 300 nm to 600 nm.

Aspect 22. The method or process defined in any one of aspects 1-19 or 21, wherein the sample (or first reference, or second reference) absorbance profile comprises an absorbance curve over a subset of wavelengths spanning less than 350 nm, less than 300 nm, less than 250 nm, less than 200 nm, or less than 150 nm.

Aspect 23. The method or process defined in any one of aspects 1-22, wherein the curve having the formula $\beta_1 F_1 + \beta_2 F_2$ is determined over a range of wavelengths, e.g., from 200 nm to 750 nm, from 300 nm to 600 nm, from 350 nm to 600 nm, or from 350 nm to 550 nm, to fit the sample absorbance profile.

Aspect 24. The method or process defined in any one of aspects 1-23, wherein the curve having the formula $\beta_1 F_1 + \beta_2 F_2$ is determined over a subset of wavelengths, e.g., spanning less than 350 nm, less than 300 nm, less than 250 nm, less than 200 nm, or less than 100 nm, in the 200 nm to 750 nm, or the 300 nm to 600 nm wavelength range, to fit the sample absorbance profile.

Aspect 25. The method or process defined in any one of the preceding aspects, wherein the least-squares regression fit value ($R^2$) is at least 0.98, at least 0.99, at least 0.999, or at least 0.9995.

Aspect 26. The method or process defined in any one of aspects 1-25, wherein the solution (comprising the first transition metal compound and the second transition metal compound), the first reference solution, and the second reference solution comprise the same solvent (e.g., the same hydrocarbon solvent).

Aspect 27. The method or process defined in any one of aspects 1-25, wherein at least two of the solution (comprising the first transition metal compound and the second transition metal compound), the first reference solution, and the second reference solution comprise a different solvent (e.g., a different hydrocarbon solvent).

Aspect 28. A catalyst preparation system comprising:
(a) a catalyst preparation vessel configured to contact a first transition metal compound, a second transition metal compound, and a solid activator, and an optional co-catalyst to form a catalyst composition;
(b) an activator feed stream configured to introduce the solid activator into the catalyst preparation vessel;
(c) a first transition metal compound feed stream configured to introduce the first transition metal compound into the catalyst preparation vessel;
(d) a second transition metal compound feed stream configured to introduce the second transition metal compound into the catalyst preparation vessel;
(e) a catalyst system feed stream configured to withdraw the catalyst composition from the catalyst preparation vessel (e.g., and to introduce the catalyst composition to a reactor, if desired); and
(f) an analytical system configured to determine a first concentration of the first transition metal compound and a second concentration of the second transition metal compound in a solution comprising the first transition metal compound and the second transition metal compound, wherein the solution is separated from (or obtained from) the catalyst composition (e.g., from the catalyst system feed stream).

Aspect 29. The system defined in aspect 28, wherein the catalyst preparation system further comprises a co-catalyst feed stream configured to introduce the co-catalyst into the catalyst preparation vessel.

Aspect 30. The system defined in aspect 28 or 29, wherein the catalyst preparation system further comprises (g) a controller configured to control a flow rate of the activator feed stream, a flow rate of the first transition metal compound feed stream, and/or a flow rate of the second transition metal compound feed stream (and/or a flow rate of the co-catalyst, if used) into the catalyst preparation vessel based on, or according to, the first concentration and/or the second concentration determined by the analytical system.

Aspect 31. The system defined in any one of aspects 28-30, wherein the first transition metal compound feed stream and the second transition metal compound feed stream feed directly into the catalyst preparation vessel.

Aspect 32. The system defined in any one of aspects 28-30, wherein the first transition metal compound feed stream and the second transition metal compound feed stream are combined prior to the catalyst preparation vessel.

Aspect 33. The system defined in any one of aspects 28-32, wherein the analytical system further comprises a liquid-solid separating device configured to separate the solution (comprising the first transition metal compound and the second transition metal compound) from the catalyst composition (e.g., from the catalyst system feed stream).

Aspect 34. A polymerization reactor system comprising:

(A) a reactor configured to contact a catalyst system with an olefin monomer and an optional olefin comonomer under polymerization reaction conditions to produce an olefin polymer;

(B) a catalyst preparation vessel configured to contact a first transition metal compound, a second transition metal compound, an activator, and an optional co-catalyst to form the catalyst system; and (C) an analytical system configured to determine a first concentration of the first transition metal compound and a second concentration of the second transition metal compound in a solution comprising the first transition metal compound and the second transition metal compound present within the polymerization reactor system.

Aspect 35. The system defined in any one of aspects 28-34, wherein the analytical system comprises an ultraviolet-visible spectrometer with an integrated computer system (a) for measuring a sample absorbance profile of the solution;

(b) for calculating a curve having the formula $\beta_1 F_1 + \beta_2 F_2$ to fit the sample absorbance profile to a least-squares regression fit value ($R^2$) of at least 0.9, wherein:

$\beta_1$ is a first weighting coefficient;

$F_1$ is a first reference absorbance profile of the first transition metal compound in a first reference solution at a first known concentration;

$\beta_2$ is a second weighting coefficient; and $F_2$ is a second reference absorbance profile of the second transition metal compound in a second reference solution at a second known concentration; and (c) for multiplying the first known concentration with $\beta_1$ to determine the first concentration of the first transition metal compound in the solution, and multiplying the second known concentration with $\beta_2$ to determine the second concentration of the second transition metal compound in the solution.

Aspect 36. The system defined in any one of aspects 28-34, wherein the analytical system comprises an ultraviolet-visible spectrometer and an external computer system, the ultraviolet-visible spectrometer configured to (a) measure a sample absorbance profile of the solution, and the external computer system configured to (b) calculate a curve having the formula $\beta_1 F_1 + \beta_2 F_2$ to fit the sample absorbance profile to a least-squares regression fit value ($R^2$) of at least 0.9, wherein:

$\beta_1$ is a first weighting coefficient;

$F_1$ is a first reference absorbance profile of the first transition metal compound in a first reference solution at a first known concentration;

$\beta_2$ is a second weighting coefficient; and $F_2$ is a second reference absorbance profile of the second transition metal compound in a second reference solution at a second known concentration; and (c) multiply the first known concentration with $\beta_1$ to determine the first concentration of the first transition metal compound in the solution, and multiplying the second known concentration with $\beta_2$ to determine the second concentration of the second transition metal compound in the solution.

Aspect 37. The system defined in any one of aspects 35-36, wherein the analytical system further comprises a filter assembly configured to filter a sample of the solution before analysis by the ultraviolet-visible spectrometer.

Aspect 38. The system defined in any one of aspects 35-37, wherein the sample (or first reference, or second reference) absorbance profile comprises an absorbance peak at a single wavelength.

Aspect 39. The system defined in any one of aspects 35-37, wherein the sample (or first reference, or second reference) absorbance profile comprises an absorbance curve (e.g., peaks and/or areas under curves) over a range of wavelengths from 200 nm to 750 nm, or from 300 nm to 600 nm.

Aspect 40. The system defined in any one of aspects 35-37 or 39, wherein the sample (or first reference, or second reference) absorbance profile comprises an absorbance curve over a subset of wavelengths spanning less than 350 nm, less than 300 nm, less than 250 nm, less than 200 nm, or less than 150 nm.

Aspect 41. The system defined in any one of aspects 35-40, wherein the solution (comprising the first transition metal compound and the second transition metal compound), the first reference solution, and the second reference solution comprise the same solvent (e.g., the same hydrocarbon solvent).

Aspect 42. The system defined in any one of aspects 35-40, wherein at least two of the solution (comprising the first transition metal compound and the second transition metal compound), the first reference solution, and the second reference solution comprise a different solvent (e.g., a different hydrocarbon solvent).

Aspect 43. The system defined in any one of aspects 34-42, wherein the reactor system further comprises (D) a controller configured to control a first flow rate of the first transition metal compound and/or a second flow rate of second transition metal compound into the reactor based on (or according to) the first concentration and/or the second concentration determined by the analytical system.

Aspect 44. The system defined in aspect 43, wherein the controller comprises a processing unit.

Aspect 45. The system defined in any one of aspects 43-44, wherein the solution comprising the first transition metal compound and the second transition metal compound is a feed stream to a catalyst preparation vessel, and the controller controls the first flow rate and/or the second flow rate into the reactor by adjusting a flow rate of the feed stream to the catalyst preparation vessel, and/or by adjusting a relative flow rate (ratio of first:second transition metal compound) to the catalyst preparation vessel, and/or by adjusting a flow rate of the catalyst system exiting the catalyst preparation vessel and entering the reactor.

Aspect 46. The system defined in any one of aspects 43-44, wherein the catalyst system is a liquid (or homogeneous) catalyst system, and the solution comprising the first transition metal compound and the second transition metal compound is a sample of the liquid catalyst system, and wherein the controller controls the first flow rate and/or the second flow rate into the reactor by adjusting a relative flow rate (ratio of first:second transition metal compound) to the reactor, and/or by adjusting a flow rate of the liquid catalyst system entering the reactor.

Aspect 47. The system defined in any one of aspects 43-44, wherein the polymerization reactor system comprises a polymerization reactor containing a mixture, and the solution comprising the first transition metal compound and the second transition metal compound is a solution prepared from a sample of the mixture from the polymerization reactor (e.g., a solution polymerization reactor, a slurry polymerization reactor), and wherein the controller controls the first flow rate and/or the second flow rate by adjusting a relative flow rate (ratio of first:second transition metal compound) to the reactor, and/or by adjusting a flow rate of the catalyst system entering the polymerization reactor.

Aspect 48. The process or system defined in any one of aspects 10-27 or 34-47, wherein the reactor system comprises one reactor.

Aspect 49. The process or system defined in any one of aspects 10-27 or 34-47, wherein the reactor system comprises two or more reactors.

Aspect 50. The process or system defined in any one of aspects 10-27 or 34-49, wherein the reactor system comprises a solution reactor, gas-phase reactor, slurry reactor, or a combination thereof.

Aspect 51. The process or system defined in any one of aspects 10-27 or 34-50, wherein the reactor system comprises a loop slurry reactor.

Aspect 52. The process or system defined in any one of aspects 10-27 or 34-51, wherein the polymerization reaction conditions comprise a polymerization reaction temperature in a range from about 60° C. to about 185° C., from about 60° C. to about 115° C., or from about 130° C. to about 180° C., and any suitable reaction pressure, e.g., from about 200 to about 1000 psig.

Aspect 53. The process or system defined in any one of aspects 5-52, wherein the catalyst system comprises a solid oxide.

Aspect 54. The process or system defined in any one of aspects 5-53, wherein the activator comprises an activator-support (e.g., fluorided silica-coated alumina or sulfated alumina).

Aspect 55. The process or system defined in any one of aspects 5-53, wherein the activator comprises an aluminoxane.

Aspect 56. The process or system defined in any one of aspects 5-53, wherein the catalyst system comprises a co-catalyst.

Aspect 57. The process or system defined in any one of aspects 5-53, wherein the catalyst system comprises an organoaluminum co-catalyst.

Aspect 58. The process or system defined in any one of aspects 10-27 or 34-57, wherein the olefin monomer comprises a $C_2$-$C_{24}$ olefin.

Aspect 59. The process or system defined in any one of aspects 10-27 or 34-57, wherein the olefin monomer comprises propylene.

Aspect 60. The process or system defined in any one of aspects 10-27 or 34-57, wherein the olefin monomer comprises ethylene.

Aspect 61. The process or system defined in any one of aspects 10-27 or 34-57, wherein the catalyst system is contacted with ethylene and an olefin comonomer comprising 1-butene, 1-hexene, 1-octene, or a mixture thereof.

Aspect 62. The process or system defined in any one of aspects 10-27 or 34-57, wherein the olefin polymer comprises an ethylene homopolymer, an ethylene copolymer, a propylene homopolymer, or a propylene-based copolymer.

Aspect 63. The process or system defined in any one of aspects 10-27 or 34-57, wherein the olefin polymer comprises an ethylene/1-butene copolymer, an ethylene/1-hexene copolymer, or an ethylene/1-octene copolymer.

Aspect 64. The method, process, or system defined in any one of aspects 1-63, wherein the first transition metal compound and the second transition metal compound, independently, comprise any suitable non-metallocene compound.

Aspect 65. The method, process, or system defined in any one of aspects 1-63, wherein the first transition metal compound and the second transition metal compound, independently, comprise any suitable metallocene compound.

Aspect 66. The method, process, or system defined in any one of aspects 1-63, wherein the first transition metal compound and the second transition metal compound, independently, comprise chromium, vanadium, titanium, zirconium, hafnium, or a combination thereof.

Aspect 67. The method, process, or system defined in any one of aspects 1-63, wherein at least one of the first transition metal compound and the second transition metal compound is a bridged metallocene compound.

Aspect 68. The method, process, or system defined in any one of aspects 1-63, wherein at least one of the first transition metal compound and the second transition metal compound is an unbridged metallocene compound.

Aspect 69. The method, process, or system defined in any one of aspects 1-68, wherein the solution comprises the first transition metal compound, the second transition metal compound, and a hydrocarbon solvent.

Aspect 70. The method, process, or system defined in any one of aspects 1-68, wherein the solution comprises the first transition metal compound, the second transition metal compound, and a hydrocarbon solvent comprising 1-hexene, isobutane, toluene, or cyclohexene, as well as mixtures or combinations thereof.

Aspect 71. The method, process, or system defined in any one of aspects 1-70, wherein a weight ratio of the first transition metal compound to the second transition metal compound in the solution is in a range from about 50:1 to about 1:50, from about 10:1 to about 1:10, from about 2:1 to about 1:2, from about 1:20 to about 1:1, etc.

Aspect 72. A method for determining a first concentration of a first transition metal compound, a second concentration of a second transition metal compound, and a third concentration of a third transition metal compound in a solution comprising the first transition metal compound, the second transition metal compound, and the third transition metal compound, the method comprising:

(i) providing a first reference absorbance profile ($F_1$) of the first transition metal compound in a first reference solution at a first known concentration, a second reference absorbance profile ($F_2$) of the second transition metal compound in a second reference solution at a second known concentration, and a third reference absorbance profile ($F_3$) of the third transition metal compound in a third reference solution at a third known concentration;

(ii) submitting a sample of the solution to a sample chamber;

(iii) irradiating the sample in the chamber with a light beam at a wavelength in the UV-visible spectrum;

(iv) generating a sample absorbance profile of the sample, and calculating a curve having the formula $\beta_1 F_1 + \beta_2 F_2 + \beta_3 F_3$ to fit the sample absorbance profile to a least-squares regression fit value ($R^2$) of at least 0.9; wherein:

$\beta_1$ is a first weighting coefficient;

$F_1$ is the first reference absorbance profile of the first transition metal compound in the first reference solution at the first known concentration;

$\beta_2$ is a second weighting coefficient;

$F_2$ is the second reference absorbance profile of the second transition metal compound in the second reference solution at the second known concentration;

$\beta_3$ is a third weighting coefficient; and $F_3$ is the third reference absorbance profile of the third transition metal compound in the third reference solution at the third known concentration; and (v) multiplying the first known concentration with $\beta_1$ to determine the first concentration of the first transition metal compound in the solution, multiplying the second known concentration with $\beta_2$ to determine the second concentration of the second transition metal compound in the solution, and multiplying the third known concentration with $\beta_3$ to determine the third concentration of the third transition metal compound in the solution.

Aspect 73. A process for operating a polymerization reactor system, the process comprising:

(I) contacting a catalyst system comprising a first transition metal compound, a second transition metal compound, a third transition metal compound, an activator, and an optional co-catalyst, with an olefin monomer and an optional olefin comonomer in a reactor within the polymerization reactor system under polymerization reaction conditions to produce an olefin polymer;

(II) determining a first concentration of the first transition metal compound, a second concentration of the second transition metal compound, and a third concentration of the third transition metal compound in a solution comprising the first transition metal compound, the second transition metal compound, and the third transition metal compound, the first concentration, the second concentration, and the third concentration determined by the method defined in aspect 72; and (III) adjusting a first flow rate of the first transition metal compound, a second flow rate of second transition metal compound, and/or a third flow rate of the third transition metal compound into the reactor when the first concentration, the second concentration, and/or the third concentration has reached a predetermined level (or adjusting the first flow rate of the first transition metal compound based on the first determined concentration, adjusting the second flow rate of the second transition metal compound based on the second determined concentration, and/or adjusting the third flow rate of the third transition metal compound based on the third determined concentration).

Aspect 74. A process for preparing a catalyst composition, the process comprising:

(I) contacting a first transition metal compound, a second transition metal compound, a third transition metal compound, a solid activator, and an optional co-catalyst (e.g., in a catalyst preparation vessel) to form the catalyst composition;

(II) determining a first concentration of the first transition metal compound, a second concentration of the second transition metal compound, and a third concentration of the third transition metal compound in a solution comprising the first transition metal compound, the second transition metal compound, and the third transition metal compound, wherein the solution is separated from (or obtained from) the catalyst composition, and the first concentration, the second concentration, and the third concentration are determined by the method defined in aspect 72; and (III) adjusting a relative amount of at least one component of the catalyst composition based on the first concentration, the second concentration, and/or the third concentration (or based on the determined concentrations).

Aspect 75. A method for measuring a property of a liquid in a vessel containing a liquid-solid mixture, the method comprising:

(i) withdrawing a sample of the liquid-solid mixture from the vessel;

(ii) flowing the sample of the liquid-solid mixture through a flow cell apparatus;

(iii) periodically stopping the flow of the sample of the liquid-solid mixture in the flow cell apparatus for a time period sufficient for the solid to settle to a bottom portion of the flow cell apparatus and for the liquid to occupy an upper portion of the flow cell apparatus;

(iv) irradiating the liquid in the upper portion of the flow cell apparatus with a light beam at a wavelength in the UV-visible spectrum to measure the property of the liquid; and (v) restoring flow through the flow cell apparatus.

Aspect 76. A flow cell apparatus for a mixture of a liquid and a solid, wherein:

the flow cell apparatus is configured to segregate the solid to a bottom portion of the flow cell apparatus and for the liquid to occupy an upper portion of the flow cell apparatus; and the upper portion of the flow cell apparatus is configured for the liquid to be irradiated with a light beam at a wavelength in the UV-visible spectrum.

Aspect 77. An analytical system for measuring a property of a liquid in a mixture of the liquid and a solid, the system comprising: the flow cell apparatus defined is aspect 76; and a UV-Vis spectrometer configured to irradiate the liquid in the upper portion of the flow cell apparatus to measure the property of the liquid.

We claim:

1. A flow cell apparatus for a mixture of a liquid and a solid, wherein:
   the flow cell apparatus is configured to segregate the solid to a bottom portion of the flow cell apparatus and for the liquid to occupy an upper portion of the flow cell apparatus; and
   the upper portion of the flow cell apparatus is configured for the liquid to be irradiated with a light beam at a wavelength in the UV-visible spectrum.

2. The apparatus of claim 1, wherein the bottom portion of the flow cell apparatus is configured to collect the solid that settles to the bottom of the flow cell apparatus due to a higher density than that of the liquid.

3. The apparatus of claim 1, wherein the bottom portion of the flow cell apparatus has the same diameter as the upper portion of the flow cell apparatus.

4. The apparatus of claim 1, wherein the bottom portion of the flow cell apparatus has a smaller diameter than that of the upper portion of the flow cell apparatus.

5. The apparatus of claim 1, wherein the mixture comprises a heterogeneous catalyst system mixture.

6. The apparatus of claim 1, wherein the liquid is a solution containing a first transition metal compound and/or a second transition metal compound.

7. The apparatus of claim 6, wherein at least one of the first transition metal compound and the second transition metal compound is a metallocene compound.

8. The apparatus of claim 1, wherein the solid comprises a solid catalyst composition.

9. An analytical system for measuring a property of a liquid in a mixture of the liquid and a solid, the system comprising:

(1) the flow cell apparatus of claim 1; and
(2) a UV-Vis spectrometer configured to irradiate the liquid in the upper portion of the flow cell apparatus to measure the property of the liquid;

wherein the bottom portion of the flow cell apparatus has a smaller diameter than that of the upper portion of the flow cell apparatus.

10. The system of claim 9, wherein the mixture comprises a heterogeneous catalyst system mixture.

11. The system of claim 9, wherein the liquid is a solution containing a first transition metal compound and/or a second transition metal compound.

12. The system of claim 11, wherein at least one of the first transition metal compound and the second transition metal compound is a metallocene compound.

13. The system of claim 11, wherein the property of the liquid is a first concentration of the first transition metal compound, a second concentration of the second transition metal compound, or both.

14. The system of claim 9, wherein the solid comprises a solid catalyst composition.

15. The apparatus of claim 8, wherein the solid catalyst composition comprises a solid activator.

16. The apparatus of claim 15, wherein the solid activator comprises an aluminoxane.

17. The apparatus of claim 15, wherein the solid activator comprises an activator-support.

18. The system of claim 14, wherein the solid catalyst composition comprises a solid activator.

19. The system of claim 18, wherein the solid activator comprises an aluminoxane.

20. The system of claim 18, wherein the solid activator comprises an activator-support.

* * * * *